(12) United States Patent
Schofield et al.

(10) Patent No.: US 10,457,728 B2
(45) Date of Patent: *Oct. 29, 2019

(54) COMPOUNDS AND METHODS FOR TREATING PAIN

(71) Applicant: MedImmune Limited, Cambridge (GB)

(72) Inventors: Darren Schofield, Melbourn (GB); Matthew Alexander Sleeman, Cambridgeshire (GB); Iain Patrick Chessell, Essex (GB); Jonathan Hatcher, Essex (GB); David Lowe, Royston (GB)

(73) Assignee: MedImmune Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/849,771

(22) Filed: Dec. 21, 2017

(65) Prior Publication Data

US 2018/0222971 A1   Aug. 9, 2018

Related U.S. Application Data

(63) Continuation of application No. 14/612,137, filed on Feb. 2, 2015, now Pat. No. 9,884,911.

(60) Provisional application No. 61/934,828, filed on Feb. 2, 2014.

(51) Int. Cl.
| | |
|---|---|
| *C07K 16/22* | (2006.01) |
| *C07K 14/715* | (2006.01) |
| *C07K 14/48* | (2006.01) |
| *A61K 39/00* | (2006.01) |

(52) U.S. Cl.
CPC ............. *C07K 16/22* (2013.01); *C07K 14/48* (2013.01); *C07K 14/7151* (2013.01); *A61K 2039/505* (2013.01); *C07K 2317/21* (2013.01); *C07K 2317/56* (2013.01); *C07K 2317/622* (2013.01); *C07K 2317/73* (2013.01); *C07K 2317/76* (2013.01); *C07K 2317/94* (2013.01); *C07K 2319/00* (2013.01); *C07K 2319/30* (2013.01); *C07K 2319/32* (2013.01)

(58) Field of Classification Search
CPC .......... A61K 2039/505; C07K 2317/76; C07K 2317/21; C07K 2317/94; C07K 16/22; C07K 2317/56; C07K 2317/73; C07K 2317/622; C07K 2319/00; C07K 2319/30; C07K 2317/651; C07K 14/48; C07K 14/7151; C07K 2319/32
See application file for complete search history.

(56) References Cited

U.S. PATENT DOCUMENTS

| | | |
|---|---|---|
| 7,001,882 B1 | 2/2006 | Schlehuber |
| 7,915,225 B2 | 3/2011 | Finck |
| 8,063,182 B1 | 11/2011 | Brockhaus et al. |
| 8,119,605 B2 | 2/2012 | Finck |
| 8,163,522 B1 | 4/2012 | Brockhaus et al. |
| 8,722,631 B2 | 5/2014 | Finck |
| 9,884,911 B2 | 2/2018 | Schofield et al. |
| 2006/0024766 A1 | 2/2006 | Atwell et al. |
| 2008/0107658 A1 | 5/2008 | Franks et al. |
| 2009/0311253 A1 | 12/2009 | Ghayur et al. |
| 2011/0250130 A1 | 10/2011 | Benatuil et al. |
| 2014/0065142 A1 | 3/2014 | Roschke et al. |
| 2014/0219913 A1 | 8/2014 | Ghayur et al. |
| 2014/0271457 A1 | 9/2014 | Ghayur et al. |
| 2015/0315283 A1 | 11/2015 | Ghayur et al. |

FOREIGN PATENT DOCUMENTS

| | | |
|---|---|---|
| WO | WO2002/096458 | 12/2002 |
| WO | WO2004/032870 | 4/2004 |
| WO | WO2006/077441 | 7/2006 |
| WO | WO2007/146968 | 12/2007 |
| WO | WO2010/006060 | 1/2010 |
| WO | WO2011/047262 | 4/2011 |
| WO | WO-2011/068993 A1 | 6/2011 |
| WO | WO-2012/162561 A2 | 11/2012 |
| WO | WO2013/070565 | 5/2013 |

OTHER PUBLICATIONS

Aloe et al., "Nerve growth factor and autoimmune rheumatic diseases," Clin. Exp. Rheumatol., 15:433-438 (1997).
Amann et al., "Inhibition of carrageenan-induced edema by indomethacin or sodium salicylate does not prevent the increase of nerve growth factor in the rat hind paw," Neurosci. Lett., 278:173-176 (2000).
Bennett et al., "Endogenous nerve growth factor regulates the sensitivity of nociceptors in the adult rat," Eur J Neurosci, 10:1282-1291 (1998).
Bennett, "Neurotrophic factors: important regulators of nociceptive function," Neuroscientist, 7:13-17 (2001).

(Continued)

*Primary Examiner* — Gregory S Emch
(74) *Attorney, Agent, or Firm* — White & Case LLP

(57) ABSTRACT

This disclosure provides compositions and methods for controlling pain. In particular the disclosure provides a method for controlling pain comprising co-administration of an NGF antagonist and a TNFα antagonist. The NGF antagonist and the TNFα antagonist can be separate molecules or part of a multifunctional polypeptide, e.g., a multispecific binding molecule that comprises an NGF antagonist domain and a TNFα antagonist domain. This disclosure also provides multifunctional polypeptides, e.g., multispecific binding molecules, comprising an NGF antagonist domain, and a TNFα antagonist domain. The method provides improved pain control. Administration of an NGF antagonist and a TNFα antagonist as provided herein can control pain in the subject more effectively than an equivalent amount of the NGF antagonist or the TNFα antagonist administered alone.

19 Claims, 20 Drawing Sheets

Specification includes a Sequence Listing.

(56) References Cited

OTHER PUBLICATIONS

Bergmann et al., "Nerve growth factor evokes hyperalgesia in mice lacking the low-affinity neurotrophin receptor p75," Neurosci. Lett., 255:87-90 (1998).
Cho et al., "Expression of mRNAs for preprotachykinin and nerve growth factor receptors in the dorsal root-ganglion following peripheral inflammation," Brain Res., 716:197-201 (1996).
Cohen et al., "A multicenter, randomized, controlled study evaluating preventive etanercept on postoperative pain after inguinal hernia repair," Anesth Analg., 116:455-462 (2013).
De Castro et al., "Corneal innervation and sensitivity to noxious stimuli in trkA knockout mice," Eur. J. Neurosci., 10:146-152 (1998).
Dimasi et al., "The design and characterization of oligospecific antibodies for simultaneous targeting of multiple disease mediators," J Mol Biol. 393:672-692 (2009).
Fjell et al., "Sodium channel experssion in NGF-overexpressing transgenic mice," J. Neurosci. Res., 57:39-47 (1999).
Genevay et al., "Efficacy of etanercept in the treatment of acute, severe sciatica: a pilot study," Ann Rheum Dis., 63:1120-1123 (2004).
Gill et al., "Biopharmaceutical drug discovery using novel protein scaffolds," Curr. Opin. Biotechnol., 17:653-658 (2006).
Heumann et al., "Changes of nerve growth factor synthesis in nonneuronal cells in response to sciatic nerve transection," J. Cell Biol., 104:1623-1631 (1987).
Hosse et al., "A new generation of protein display scaffolds for molecular recognition," Protein Science, 15:14-27 (2006).
Huang et al., "Neurotrophins: roles in neuronal development and function," Ann. Rev. Neurosci., 24:677-736 (2001).
Indo, "Genetics of congenital insensitivity to pain with anhidrosis (CIPA) or hereditary sensory and autonomic neuropathy type IV. Clinical, biological and molecular aspects of mutations in TRKA(NTRK1) gene encoding the receptor tyrosine kinase for nerve growth factor," Clin. Auton. Res., 12 (Supp 1):120-132 (2002).
International Search Report and Written Opinion in PCT/EP2015/052098, dated Apr. 23, 2015.
Jung et al., "Selection for improved protein stability by phage display," J Mol Biol. Nov. 19, 1999;294(1):163-80.
Kim et al., "Comparative analyses of complex formation and binding sites between human tumor necrosis factor-alpha and its three antagonists elucidate their different neutralizing mechanisms," J. Mol. Biol., 374: 1374-1388 (2007).
Kivitz et al., "Efficacy and safety of tanezumab versus naproxen in the treatment of chronic low back pain," Pain, 154:1009-1021 (2013).
Leung et al., "TNF-alpha and neuropathic pain—a review," J. Neuroinflammation, 7:27 (11 pages) (2010).
Lowe et al., "Increased nerve growth factor levels in the urinary bladder of women with idiopathic sensory urgency and interstitial cystitis," Br. J. Urol., 79:572-577 (1997).
Ma et al., "The progressive tactile hyperalgesia induced by peripheral inflammation is nerve growth factor dependent," Neuroreport., 8:807-810 (1997).
Mamet et al., "How nerve growth factor drives physiological and inflammatory expressions of acid-sensing ion channel 3 in sensory neurons," J. Biol. Chem., 278:48907-48913 (1999).

McArthur et al., "A phase II trial of nerve growth factor for sensory neuropathy associated with HIV infection. AIDS Clinical Trials Group Team 291," Neurology, 54: 1080-1088 (2000).
Mendell et al., "Diversity of neurotrophin action in the postnatal spinal cord," Brain Res. Rev. 40:230-239 (2002).
Milligan et al., "Spinal glia arid proinflammatory cytokines mediate mirror-image neuropathic pain in rats," J Neurosci, 23:1026-1040 (2003).
Nygren, "Alternative binding proteins: affibody binding proteins developed from a small three-helix bundle scaffold," FEBS J., 275:2668-2676 (2008).
Petty et al., "The effect of systemically administered recombinant human nerve growth factor in healthy human subjects," Ann. Neural., 36:244-246 (1994).
Pozza et al., "A histochemical study of the rheumatoid synovium: focus on nitric oxide, nerve growth factor high affinity receptor, and innervation," J. Rheumatol., 27:1121-1127 (2000).
Priestley et al., "Regulation of nociceptive neurons by nerve growth factor and glial cell line derived neurotrophic factor," Can. J. Physiol. Pharmacol. 80:495-505 (2002).
Qiao et al., "Cystitis-induced upregulation of tyrosine kinase (TrkA, TrkB) receptor expression and phosphorylation in rat micturition pathways," J. Comp. Neural., 454:200-211 (2002).
Ramer et al., "Causes and consequences of sympathetic basket formation in dorsal root ganglia," Pain, Supp. 6:S111-120 (1998).
Reiter et al. Engineering antibody Fv fragments for cancer detection and therapy: disulfide-stabilized Fv fragments. Nat Biotechnol. Oct. 1996;14(10):1239-45.
Roberge et al., "Construction and optimization of a CC49-based scFv-beta-lactamase fusion protein for ADEPT," Protein Eng Des Sel. Apr. 2006;19(4):141-5.
Sah et al., "Neurotrophic Factors As Novel Therapeutics for Neuropathic Pain," Nat. Rev. Drug Disc., 2:460-472 (2003).
Sanga et al., "Efficacy, safety, and tolerability of fulranumab, an anti-nerve growth factor antibody, in the treatment of patients with moderate to severe osteoarthritis pain," Pain, 154:1910-1919 (2013).
Skerra, "Alternative binding proteins: anticalins—harnessing the structural plasticity of the lipocalin ligand pocket to engineer novel binding activities," FEBS J., 275:2677-2683 (2008).
Skerra, "Alternative non-antibody scaffolds for molecular recognition," Curr. Opin. Biotechnol., 18:295-304 (2007).
Sommer et al., "Etanercept reduces hyperalgesia in experimental painful neuropathy," J. Peripher. Nerv. Syst., 6:67-72 (2001).
Spierings et al. "A phase 111 placebo- and oxycodone-controlled study of tanezumab in adults with osteoarthritis pain of the hip or knee," Pain, 154:1603-1612 (2013).
Tischenko VM, Abramov VM, Zav'yalov VP (1998) Investigation of the cooperative structure of Fc fragments from myeloma immunoglobulin G. Biochemistry 37: 5576-5581.
Wallis, "Tumour necrosis factor antagonists: structure, function, and tuberculosis risks," Lancet Infect. Dis., 8:601-611 (2008).
Wen et al., "Nerve conduction blockade in the sciatic nerve prevents but does not reverse the activation of p38 mitogen-activated protein kinase in spinal microglia in the rat spared nerve injury model," Anesthesiology, 107:312-321 (2007).
Zhang et al., "NGF-mediated sensitization of the excitability of rat sensory neurons is prevented by a blocking antibody to the p75 neurotrophin receptor," Neurosci. Lett., 366:187-192 (2004).
Zhuang et al., "ERK is sequentially activated in neurons, microglia, and astrocytes by spinal nerve ligation and contributes to mechanical allodynia in this neuropathic pain model," Pain, 114:149-159 (2005).

TNFR2 (75kd)

Human IgG1 Fc anti-NGF (scFv)

SEQUENCE LISTING

<160> NUMBER OF SEQ ID NOS: 99

<210> SEQ ID NO 1
<211> LENGTH: 241
<212> TYPE: PRT
<213> ORGANISM: Homo sapiens

<400> SEQUENCE: 1

Met Ser Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
            20                  25                  30

Pro Gln Ala His Trp Thr Lys Leu Gln His Ser Leu Asp Thr Ala Leu
        35                  40                  45

Arg Arg Ala Arg Ser Ala Pro Ala Ala Ala Ile Ala Ala Arg Val Ala
    50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser Ser His Pro Ile Phe
        115                 120                 125

His Arg Gly Glu Phe Ser Val Cys Asp Ser Val Ser Val Trp Val Gly
    130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr Thr His Thr Phe Val
        195                 200                 205

Lys Ala Leu Thr Met Asp Gly Lys Gln Ala Ala Trp Arg Phe Ile Arg
    210                 215                 220

Ile Asp Thr Ala Cys Val Cys Val Leu Ser Arg Lys Ala Val Arg Arg
225                 230                 235                 240

Ala

<210> SEQ ID NO 2
<211> LENGTH: 233
<212> TYPE: PRT
<213> ORGANISM: Homo sapiens

<400> SEQUENCE: 2

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Ala Asn Pro
            85                  90                  95

Gln Ala Glu Gly Gln Leu Gln Trp Leu Asn Arg Arg Ala Asn Ala Leu
        100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
                180                 185                 190

Pro Ile Tyr Leu Gly Gly Val Phe Gln Leu Glu Lys Gly Asp Arg Leu
                195                 200                 205

Ser Ala Glu Ile Asn Arg Pro Asp Tyr Leu Asp Phe Ala Glu Ser Gly
        210                 215                 220

Gln Val Tyr Phe Gly Ile Ile Ala Leu
225                 230

<210> SEQ ID NO 3
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Arg Ile Tyr Asp Leu Asn Pro Ser Leu Thr Ala Tyr
                100                 105                 110

Tyr Asp Met Asp Val Trp Gly Gln Gly Thr Met Val Thr Val Ser Ser
        115                 120                 125

<210> SEQ ID NO 4
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

```
Thr Tyr Gly Ile Ser
1               5

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Ile Ile Pro Ile Phe Asp Thr Gly Asn Ser Ala Gln Ser Phe Gln
1               5                   10                  15

Gly

<210> SEQ ID NO 6
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ser Ser Arg Ile Tyr Asp Leu Asn Pro Ser Leu Thr Ala Tyr Tyr Asp
1               5                   10                  15

Met Asp Val

<210> SEQ ID NO 7
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 8
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 8

Ser Gly Ser Ser Ser Asn Ile Gly Asn Asn Tyr Val Ser
1               5                   10

<210> SEQ ID NO 9
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Asp Asn Asn Lys Arg Pro Ser
1               5

<210> SEQ ID NO 10
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Thr Trp Asp Ser Ser Leu Ser Ala Trp Val
1               5                   10

<210> SEQ ID NO 11
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ser Ser Arg Ile Tyr Asp Phe Asn Ser Ala Leu Ile Ser Tyr Tyr Asp
1               5                   10                  15

Met Asp Val

<210> SEQ ID NO 12
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ser Ser Arg Ile Tyr Asp Met Ile Ser Ser Leu Gln Pro Tyr Tyr Asp
1               5                   10                  15

Met Asp Val

<210> SEQ ID NO 13
<211> LENGTH: 467
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 13

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro

```
                      405                 410                 415
Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys
465

<210> SEQ ID NO 14
<211> LENGTH: 731
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285
```

```
Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly Lys Gly Gly Gly Gly Ser Gly Gly Gly Gly Ser Gln Val Gln
465                 470                 475                 480

Leu Val Gln Ser Gly Ala Glu Val Lys Lys Pro Gly Ser Ser Val Lys
                485                 490                 495

Val Ser Cys Lys Ala Ser Gly Gly Thr Phe Ser Thr Tyr Gly Ile Ser
                500                 505                 510

Trp Val Arg Gln Ala Pro Gly Gln Gly Leu Glu Trp Met Gly Gly Ile
            515                 520                 525

Ile Pro Ile Phe Asp Thr Gly Asn Ser Ala Gln Ser Phe Gln Gly Arg
530                 535                 540

Val Thr Ile Thr Ala Asp Glu Ser Thr Ser Thr Ala Tyr Met Glu Leu
545                 550                 555                 560

Ser Ser Leu Arg Ser Glu Asp Thr Ala Val Tyr Tyr Cys Ala Arg Ser
                565                 570                 575

Ser Arg Ile Tyr Asp Leu Asn Pro Ser Leu Thr Ala Tyr Tyr Asp Met
            580                 585                 590

Asp Val Trp Gly Gln Gly Thr Met Val Thr Val Ser Ser Gly Gly Gly
            595                 600                 605

Gly Ser Gly Gly Gly Gly Ser Gly Gly Gly Gly Ser Ala Gln Ser Val
            610                 615                 620

Leu Thr Gln Pro Pro Ser Val Ser Ala Ala Pro Gly Gln Lys Val Thr
625                 630                 635                 640

Ile Ser Cys Ser Gly Ser Ser Ser Asn Ile Gly Asn Asn Tyr Val Ser
                645                 650                 655

Trp Tyr Gln Gln Leu Pro Gly Thr Ala Pro Lys Leu Leu Ile Tyr Asp
                660                 665                 670

Asn Asn Lys Arg Pro Ser Gly Ile Pro Asp Arg Phe Ser Gly Ser Lys
            675                 680                 685

Ser Gly Thr Ser Ala Thr Leu Gly Ile Thr Gly Leu Gln Thr Gly Asp
            690                 695                 700
```

Glu Ala Asp Tyr Tyr Cys Gly Thr Trp Asp Ser Ser Leu Ser Ala Trp
705                 710                 715                 720

Val Phe Gly Gly Gly Thr Lys Leu Thr Val Leu
                725                 730

<210> SEQ ID NO 15
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Gly Gly Gly Gly Ser Gly Gly Gly Gly Ser Gly Gly Gly Gly Ser
1               5                   10                  15

<210> SEQ ID NO 16
<211> LENGTH: 2193
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16

| | | | | |
|---|---|---|---|---|
| ctgcccgccc | aggtggcctt | taccccttat | gcccccgagc | ccggcagcac | ctgtcggctg | 60 |
| agagagtact | acgaccagac | cgcccagatg | tgctgcagca | agtgtctcc | tggccagcat | 120 |
| gccaaggtgt | tctgcaccaa | gaccagcgac | accgtgtgcg | acagctgcga | ggacagcacc | 180 |
| tacacccagc | tgtggaactg | ggtgcccgag | tgcctgagct | gcggcagcag | atgcagcagc | 240 |
| gaccaggtgg | aaacccaggc | ctgcaccaga | gagcagaacc | ggatctgcac | ctgtagaccc | 300 |
| ggctggtact | gcgccctgag | caagcaggaa | ggctgcagac | tctgcgcccc | tctgcggaag | 360 |
| tgcagacccg | gctttggcgt | ggccagaccc | ggcaccgaga | caagcgacgt | ggtctgtaag | 420 |
| ccctgcgctc | ctggcacctt | cagcaacacc | accagcagca | ccgacatctg | cagaccccac | 480 |
| cagatctgca | acgtggtggc | catccccggc | aacgccagca | tggatgccgt | ctgcaccagc | 540 |
| actagcccca | ccagaagtat | ggcccctggc | gccgtgcatc | tgccccagcc | tgtgtccacc | 600 |
| agaagccagc | acacccagcc | cacccctgag | cctagcaccg | cccctccac | cagctttctg | 660 |
| ctgcctatgg | gcctagccc | tccagccgag | ggaagcacag | gcgacgagcc | caagagctgc | 720 |
| gacaagaccc | acacctgtcc | ccctgccct | gccctgaac | tgctgggcgg | acccagcgtg | 780 |
| ttcctgttcc | ccccaaagcc | caaggacacc | ctgatgatca | gccggacccc | cgaagtgacc | 840 |
| tgcgtggtgg | tggacgtgtc | ccacgaggac | cctgaagtga | agttcaattg | gtacgtggac | 900 |
| ggcgtggaag | tgcacaacgc | caagaccaag | cccagagagg | aacagtacaa | ctccacctac | 960 |
| cgggtggtgt | ccgtgctgac | cgtgctgcac | caggactggc | tgaacggcaa | agagtacaag | 1020 |
| tgcaaggtct | ccaacaaggc | cctgcctgcc | cccatcgaga | aaaccatcag | caaggccaag | 1080 |
| ggccagcccc | gcgagcctca | ggtgtacaca | ctgccccca | gccgggaaga | gatgaccaag | 1140 |
| aaccaggtgt | ccctgacctg | cctggtcaaa | ggcttctacc | ccagcgatat | cgccgtggaa | 1200 |
| tgggagagca | atggccagcc | cgagaacaac | tacaagacca | ccccccctgt | gctggacagc | 1260 |
| gacggctcat | tcttcctgta | cagcaagctg | accgtggaca | gagccggtg | gcagcagggc | 1320 |
| aacgtgttca | gctgcagcgt | gatgcacgag | gccctgcaca | accactacac | ccagaagtcc | 1380 |

-continued

```
ctgagcctga gccccggaaa gggcggtggc ggatccggag gtgggggatc tcaggtgcag    1440
ctggtgcagt ctggcgccga agtgaagaaa cccggctcta gcgtgaaggt gtcctgcaag    1500
gccagcggcg gcaccttctc cacctacggc atcagctggg tccgccaggc ccctggacag    1560
ggcctggaat ggatgggcgg catcatcccc atcttcgaca ccggcaacag cgcccagagc    1620
ttccagggca gagtgaccat caccgccgac gagagcacct ccaccgccta catggaactg    1680
agcagcctgc ggagcgagga caccgccgtg tactactgcg ccagaagcag ccggatctac    1740
gacctgaacc ccagcctgac cgcctactac gacatggacg tgtggggcca gggcaccatg    1800
gtcacagtgt ctagcggagg cggcggatct ggcggcggag gaagtggcgg gggaggatct    1860
gcccagagcg tgctgaccca gcccccttct gtgtctgccg cccctggcca gaaagtgacc    1920
atctcctgca gcggcagcag cagcaacatc ggcaacaact acgtgtcctg gtatcagcag    1980
ctgcccggca ccgcccctaa gctgctgatc tacgacaaca caagcggcc cagcggcatc    2040 cccgaccggt ttagcggcag caagagcggg acttctgcta cactgggcat cacaggcctg    2100
cagaccggca cgaggccga ctactactgc ggcacctggg acagcagcct gagcgcttgg    2160
gtgttcggcg gaggcaccaa gctgacagtg ctg                                2193
```

<210> SEQ ID NO 17
<211> LENGTH: 735
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

```
Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205
```

-continued

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
    450                 455                 460

Pro Gly Lys Gly Gly Gly Gly Ser Gly Gly Gly Gly Ser Gln Val Gln
465                 470                 475                 480

Leu Val Gln Ser Gly Ala Glu Val Lys Lys Pro Gly Ser Ser Val Lys
                485                 490                 495

Val Ser Cys Lys Ala Ser Gly Gly Thr Phe Ser Thr Tyr Gly Ile Ser
            500                 505                 510

Trp Val Arg Gln Ala Pro Gly Gln Cys Leu Glu Trp Met Gly Gly Ile
    515                 520                 525

Ile Pro Ile Phe Asp Thr Gly Asn Ser Ala Gln Ser Phe Gln Gly Arg
    530                 535                 540

Val Thr Ile Thr Ala Asp Glu Ser Thr Ser Thr Ala Tyr Met Glu Leu
545                 550                 555                 560

Ser Ser Leu Arg Ser Glu Asp Thr Ala Val Tyr Tyr Cys Ala Arg Ser
            565                 570                 575

Ser Arg Ile Tyr Asp Leu Asn Pro Ser Leu Thr Ala Tyr Tyr Asp Met
            580                 585                 590

Asp Val Trp Gly Gln Gly Thr Met Val Thr Val Ser Ser Gly Gly Gly
            595                 600                 605

Gly Ser Gly Gly Gly Gly Ser Gly Gly Gly Gly Ser Gly Gly Gly Gly
        610                 615                 620

Ser Gln Ser Val Leu Thr Gln Pro Pro Ser Val Ser Ala Ala Pro Gly

```
                625                 630                 635                 640
        Gln Lys Val Thr Ile Ser Cys Ser Gly Ser Ser Asn Ile Gly Asn
                        645                 650                 655

Asn Tyr Val Ser Trp Tyr Gln Gln Leu Pro Gly Thr Ala Pro Lys Leu
                        660                 665                 670

Leu Ile Tyr Asp Asn Asn Lys Arg Pro Ser Gly Ile Pro Asp Arg Phe
                        675                 680                 685

Ser Gly Ser Lys Ser Gly Thr Ser Ala Thr Leu Gly Ile Thr Gly Leu
                        690                 695                 700

Gln Thr Gly Asp Glu Ala Asp Tyr Tyr Cys Gly Thr Trp Asp Ser Ser
        705                 710                 715                 720

Leu Ser Ala Trp Val Phe Gly Cys Gly Thr Lys Leu Thr Val Leu
                        725                 730                 735

<210> SEQ ID NO 18
<211> LENGTH: 2205
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
ctgcccgccc aggtggcctt tacccttat gccccgagc cggcagcac ctgtcggctg      60 agagagtact acgaccagac cgcccagatg tgctgcagca agtgctctcc tggccagcat    120
gccaaggtgt tctgcaccaa gaccagcgac accgtgtgcg acagctgcga ggacagcacc    180
tacacccagc tgtggaactg ggtgcccgag tgcctgagct gcggcagcag atgcagcagc    240
gaccaggtgg aaacccaggc ctgcaccaga gagcagaacc ggatctgcac ctgtagaccc    300
ggctggtact gcgccctgag caagcaggaa ggctgcagac tctgcgcccc tctgcggaag    360
tgcagacccg gctttggcgt ggccagaccc ggcaccgaga caagcgacgt ggtctgcaag    420
ccctgcgctc ctggcacctt cagcaacacc accagcagca ccgacatctg cagaccccac    480
cagatctgca acgtggtggc catccccggc aacgccagca tggatgccgt gtgcaccagc    540
accagcccca ccagaagtat ggcccctggc gccgtgcatc tgccccagcc tgtgtccacc    600
agaagccagc acacccagcc cacccctgag cctagcaccg ccccctccac cagctttctg    660
ctgcctatgg gccctagccc tccagccgag ggaagcacag gcgacgagcc caagagctgc    720
gacaagaccc acacctgtcc ccctgccct gccctgaac tgctgggcgg acccagcgtg    780
ttcctgttcc cccaaagcc caaggacacc ctgatgatca gccggacccc cgaagtgacc    840
tgcgtggtgg tggacgtgtc ccacgaggac cctgaagtga agttcaattg gtacgtggac    900
ggcgtggaag tgcacaacgc caagaccaag cccagagagg aacagtacaa ctccacctac    960
cgggtggtgt ccgtgctgac cgtgctgcac caggactggc tgaacggcaa agagtacaag   1020
tgcaaagtct ccaacaaggc cctgcctgcc cccatcgaga aaaccatcag caaggccaag   1080
ggccagcccc gcgagcctca ggtgtacaca ctgccccca gccgggaaga tgaccaag   1140 aaccaggtgt ccctgacctg cctggtcaaa ggcttctacc ccagcgatat cgccgtggaa   1200
tgggagagca acggccagcc cgagaacaac tacaagacca ccccccctgt gctggacagc   1260
gacggctcat tcttcctgta cagcaagctg accgtggaca agagccggtg gcagcagggc   1320
aatgtcttca gctgtagcgt gatgcacgag gccctgcaca accactacac ccagaagtcc   1380
ctgagcctga gccccggaaa gggcggaggc ggatccggag tgggggatc tcaggtgcag   1440
```

```
ctggtgcagt ctggcgccga agtgaagaaa cccggctcta gcgtgaaggt gtcctgcaag    1500
gccagcggcg gcaccttctc cacctacggc atcagctggg tccgccaggc ccctggacag    1560
tgtctggaat ggatgggcgg catcatcccc atcttcgaca ccggcaacag cgcccagagc    1620
ttccagggca gagtgaccat caccgccgac gagagcacct ccaccgccta catggaactg    1680
agcagcctgc ggagcgagga caccgccgtg tactactgcg ccagaagcag ccggatctac    1740
gacctgaacc ccagcctgac cgcctactac gacatggacg tgtggggcca gggcaccatg    1800
gtcacagtgt ctagcggagg cggaggcagc ggaggtggtg atctggtgg cggaggaagt     1860 ggcggcggag gctctcagag cgtgctgacc cagccccctt ctgtgtctgc cgcccctggc    1920
cagaaagtga ccatctcctg cagcggcagc agcagcaaca tcggcaacaa ctacgtgtcc    1980
tggtatcagc agctgcccgg caccgcccct aagctgctga tctacgacaa caacaagcgg    2040
cccagcggca tccccgaccg gtttagcggc agcaagagcg ggacttctgc tacactgggc    2100
atcacaggcc tgcagaccgg cgacgaggcc gactactact gcggcaccct ggacagcagc    2160
ctgagcgctt gggtgttcgg ctgcggcacc aagctgacag tgctg                    2205
```

<210> SEQ ID NO 19
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 19

Gly Gly Gly Gly Ser Gly Gly Gly Gly Ser Gly Gly Gly Gly Ser Gly
1               5                   10                  15

Gly Gly Gly Ser
            20

<210> SEQ ID NO 20
<211> LENGTH: 215
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Ile Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser

```
              115                 120                 125
Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 21
<211> LENGTH: 645
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
gaaatcgtgc tgacccagag ccccgccacc ctgtctctga gccctggcga gagagccacc    60
ctgagctgca gagccagcca gagcgtgtac tcctacctgg cttggtatca gcagaagccc   120
ggccaggccc ccagactgct gatctacgac gccagcaacc gggccatcgg catccctgcc   180 agatttctg gcagcggcag cggcaccgac ttcaccctga ccatcagcag cctggaaccc   240
gaggacttcg ccgtgtacta ctgccagcag cggagcaact ggccccccctt caccttcggc   300 cctggcacca aggtggacat caagcgtacg gtggctgcac catctgtctt catcttcccg   360
ccatctgatg agcagttgaa atctggaact gcctctgttg tgtgcctgct gaataacttc   420
tatcccagag aggccaaagt acagtggaag gtggataacg ccctccaatc gggtaactcc   480
caggagagtg tcacagagca ggacagcaag gacagcacct acagcctcag cagcaccctg   540
acgctgagca agcagactac gagaaacac aaagtctacg cctgcgaagt cacccatcag   600
ggcctgagct cgcccgtcac aaagagcttc aacaggggag agtgt                   645

<210> SEQ ID NO 22
<211> LENGTH: 724
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Ser Lys Asn Thr Leu Tyr
```

-continued

```
            65                  70                  75                  80
Leu Gln Met Asn Ser Leu Arg Ala Glu Asp Thr Ala Val Tyr Tyr Cys
                    85                  90                  95

Ala Arg Asp Arg Gly Ile Ser Ala Gly Gly Asn Tyr Tyr Tyr Tyr Gly
                100                 105                 110

Met Asp Val Trp Gly Gln Gly Thr Thr Val Thr Val Ser Ser Ala Ser
                115                 120                 125

Thr Lys Gly Pro Ser Val Phe Pro Leu Ala Pro Ser Ser Lys Ser Thr
            130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
                180                 185                 190

Ser Val Val Thr Val Pro Ser Ser Leu Gly Thr Gln Thr Tyr Ile
                195                 200                 205

Cys Asn Val Asn His Lys Pro Ser Asn Thr Lys Val Asp Lys Arg Val
            210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
                260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Tyr Thr Leu Pro Pro Ser Arg Glu Glu Met Thr
            355                 360                 365

Lys Asn Gln Val Ser Leu Thr Cys Leu Val Lys Gly Phe Tyr Pro Ser
370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly Lys Gly Gly Gly Ser Gly Gly Gly
            450                 455                 460

Gly Ser Gln Val Gln Leu Val Gln Ser Gly Ala Glu Val Lys Lys Pro
465                 470                 475                 480

Gly Ser Ser Val Lys Val Ser Cys Lys Ala Ser Gly Gly Thr Phe Ser
                485                 490                 495
```

Thr Tyr Gly Ile Ser Trp Val Arg Gln Ala Pro Gly Gln Cys Leu Glu
              500                 505                 510

Trp Met Gly Gly Ile Ile Pro Ile Phe Asp Thr Gly Asn Ser Ala Gln
            515                 520                 525

Ser Phe Gln Gly Arg Val Thr Ile Thr Ala Asp Glu Ser Thr Ser Thr
        530                 535                 540

Ala Tyr Met Glu Leu Ser Ser Leu Arg Ser Glu Asp Thr Ala Val Tyr
545                 550                 555                 560

Tyr Cys Ala Arg Ser Ser Arg Ile Tyr Asp Leu Asn Pro Ser Leu Thr
                565                 570                 575

Ala Tyr Tyr Asp Met Asp Val Trp Gly Gln Gly Thr Met Val Thr Val
            580                 585                 590

Ser Ser Gly Gly Gly Gly Ser Gly Gly Gly Ser Gly Gly Gly Gly
        595                 600                 605

Ser Gly Gly Gly Gly Ser Gln Ser Val Leu Thr Gln Pro Pro Ser Val
    610                 615                 620

Ser Ala Ala Pro Gly Gln Lys Val Thr Ile Ser Cys Ser Gly Ser Ser
625                 630                 635                 640

Ser Asn Ile Gly Asn Asn Tyr Val Ser Trp Tyr Gln Gln Leu Pro Gly
                645                 650                 655

Thr Ala Pro Lys Leu Leu Ile Tyr Asp Asn Asn Lys Arg Pro Ser Gly
            660                 665                 670

Ile Pro Asp Arg Phe Ser Gly Ser Lys Ser Gly Thr Ser Ala Thr Leu
        675                 680                 685

Gly Ile Thr Gly Leu Gln Thr Gly Asp Glu Ala Asp Tyr Tyr Cys Gly
    690                 695                 700

Thr Trp Asp Ser Ser Leu Ser Ala Trp Val Phe Gly Cys Gly Thr Lys
705                 710                 715                 720

Leu Thr Val Leu

<210> SEQ ID NO 23
<211> LENGTH: 2172
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23
caggtgcagc tggtggaaag cggcggaggc gtggtgcagc ccggcagaag cctgagactg      60
agctgcgctg ccagcggctt catcttcagc agctacgcca tgcactgggt ccgccaggcc     120
cctggcaacg gactggaatg ggtggccttc atgagctacg acggcagcaa caagaagtac     180
gccgacagcg tgaagggccg gttcaccatc agccgggaca cagcaagaa caccctgtac     240 ctgcagatga acagcctgcg ggctgaggac accgccgtgt actactgcgc cagagaccga     300
ggcatcagtg ctggcggcaa ctactactac tacggcatgg acgtgtgggg ccagggcacc     360
accgtgaccg tgtctagcgc gtcgaccaag ggcccatccg tcttccccct ggcaccctcc     420
tccaagagca cctctggggg cacagcggcc ctgggctgcc tggtcaagga ctacttcccc     480
gaaccggtga cggtgtcctg gaactcaggc gctctgacca gcggcgtgca caccttcccg     540
gctgtcctac agtcctcagg actctactcc ctcagcagcg tggtgaccgt gccctccagc     600
agcttgggca cccagaccta catctgcaac gtgaatcaca agcccagcaa caccaaggtg     660

```
gacaagagag ttgagcccaa atcttgtgac aaaactcaca catgcccacc gtgcccagca    720
cctgaactcc tggggggacc gtcagtcttc ctcttccccc caaaacccaa ggacaccctc    780
atgatctccc ggacccctga ggtcacatgc gtggtggtgg acgtgagcca cgaagaccct    840
gaggtcaagt tcaactggta cgtggacggc gtggaggtgc ataatgccaa gacaaagccg    900
cgggaggagc agtacaacag cacgtaccgt gtggtcagcg tcctcaccgt cctgcaccag    960
gactggctga atggcaagga gtacaagtgc aaggtctcca acaaagccct cccagccccc   1020
atcgagaaaa ccatctccaa agccaaaggg cagccccgag aaccacaggt ctacaccctg   1080
cccccatccc gggaggagat gaccaagaac caggtcagcc tgacctgcct ggtcaaaggc   1140
ttctatccca gcgacatcgc cgtggagtgg gagagcaatg ggcagccgga gaacaactac   1200
aagaccacgc ctcccgtgct ggactccgac ggctccttct tcctctatag caagctcacc   1260
gtggacaaga gcaggtggca gcaggggaac gtcttctcat gctccgtgat gcatgaggct   1320
ctgcacaacc actacacgca gaagagcctc tccctgtctc cgggtaaagg cggagggga   1380
tccggcggag ggggctctca ggtgcagctg gtgcagtctg gcgccgaagt gaagaaaccc   1440
ggctctagcg tgaaggtgtc ctgcaaggcc agcggcggca ccttctccac ctacggcatc   1500
agctgggtcc gccaggcccc tggacagtgt ctggaatgga tgggcggcat catccccatc   1560
ttcgacaccg caacagcgc ccagagcttc cagggcagag tgaccatcac cgccgacgag   1620
agcacctcca ccgcctacat ggaactgagc agcctgcgga gcgaggacac cgccgtgtac   1680
tactgcgcca gaagcagccg gatctacgac ctgaacccca gcctgaccgc ctactacgac   1740
atggacgtgt ggggccaggg caccatggtc acagtgtcta gcggaggcgg aggcagcgga   1800
ggtggtggat ctggtggcgg aggaagtggc ggcggaggct ctcagagcgt gctgacccag   1860
cccccttctg tgtctgccgc cctggccag aaagtgacca tctcctgcag cggcagcagc   1920
agcaacatcg gcaacaacta cgtgtcctgg tatcagcagc tgcccggcac cgcccctaag   1980
ctgctgatct acgacaacaa caagcggccc agcggcatcc ccgaccggtt tagcggcagc   2040
aagagcggga cttctgctac actgggcatc acaggcctgc agaccggcga cgaggccgac   2100
tactactgcg gcacctggga cagcagcctg agcgcttggg tgttcggctg cggcaccaag   2160
ctgacagtgc tg                                                       2172
```

<210> SEQ ID NO 24
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Trp Phe Gly
            20                  25                  30

Ala Phe Thr Trp Val Arg Gln Ala Pro Gly Gln Gly Leu Glu Trp Met
        35                  40                  45

Gly Gly Ile Ile Pro Ile Phe Gly Leu Thr Asn Leu Ala Gln Asn Phe
    50                  55                  60

Gln Gly Arg Val Thr Ile Thr Ala Asp Glu Ser Thr Ser Thr Val Tyr
65                  70                  75                  80
```

```
Met Glu Leu Ser Ser Leu Arg Ser Glu Asp Thr Ala Val Tyr Tyr Cys
            85                  90                  95

Ala Arg Ser Ser Arg Ile Tyr Asp Leu Asn Pro Ser Leu Thr Ala Tyr
        100                 105                 110

Tyr Asp Met Asp Val Trp Gly Gln Gly Thr Met Val Thr Val Ser Ser
        115                 120                 125

<210> SEQ ID NO 25
<211> LENGTH: 384
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
caggtgcagc tggtgcagtc tggggctgag gtgaagaagc ctgggtcctc ggtgaaggtc    60
tcctgcaagg cctctggagg caccttctgg ttcggcgcgt tcacctgggt gcgacaggcc   120
cctggacaag gacttgagtg gatgggaggg attattccta tcttcgggtt gacgaacttg   180
gcacagaact tccagggcag agtcacgatt accgcggacg aatccacgag cacagtctac   240
atggagctga gcagcttgag atctgaagac acggccgtat attattgtgc acgttcaagt   300
cgtatctacg atctgaaccc gtccctgacc gcctactacg atatggatgt ctggggccag   360
gggacaatgg tcaccgtctc gagt                                          384

<210> SEQ ID NO 26
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asp Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 27
<211> LENGTH: 330
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27
```

```
cagtctgtgc tgactcagcc gccatcagtg tctgcggccc caggacagaa ggtcaccatc        60
tcctgctctg gaagcagctc cgacattggg aataattatg tatcgtggta ccagcagctc       120
ccaggaacag cccccaaact cctcatttat gacaataata agcgaccctc agggattcct       180
gaccgattct ctggctccaa gtctggcacg tcagccaccc tgggcatcac cggactccag       240
actggggacg aggccgatta ttactgcgga acatgggata gcagcctgag tgcttgggtg       300
ttcggcggag ggaccaagct gaccgtccta                                        330
```

<210> SEQ ID NO 28
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Ala Met His Trp Val Arg Gln Ala Pro Gly Asn Gly Leu Glu Trp Val
        35                  40                  45

Ala Phe Met Ser Tyr Asp Gly Ser Asn Lys Lys Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Ile Ser Ala Gly Gly Asn Tyr Tyr Tyr Gly
            100                 105                 110

Met Asp Val Trp Gly Gln Gly Thr Thr Val Thr Val Ser Ser
        115                 120                 125
```

<210> SEQ ID NO 29
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Tyr Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Ile Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95
```

Phe Thr Phe Gly Pro Gly Thr Lys Val Asp Ile Lys
            100                 105

<210> SEQ ID NO 30
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Glu Val Gln Leu Val Gln Thr Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Thr Ala Val Tyr Tyr Cys
                85                  90                  95

Ala Ser Ser Arg Ile Tyr Asp Ala Asn Arg Gln Ala Val Pro Tyr
            100                 105                 110

Tyr Asp Met Asp Val Trp Gly Gln Gly Thr Met Val Thr Val Ser Ser
        115                 120                 125

<210> SEQ ID NO 31
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Gln Ala Val Leu Thr Gln Pro Ser Ser Val Ser Thr Pro Pro Gly Gln
1               5                   10                  15

Met Val Thr Ile Ser Cys Ser Gly Ser Ser Ser Asp Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 32
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Phe Thr Ser Gly Leu Ala Pro Tyr
            100                 105                 110

Tyr Asp Met Asp Val Trp Gly Gln Gly Thr Met Val Thr Val Ser Ser
        115                 120                 125

<210> SEQ ID NO 33
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Pro Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Thr Trp Val Phe Gly Gly Gly Thr Lys Leu Thr Val Leu
            100                 105                 110

<210> SEQ ID NO 34
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Ala Gly Asn Ser Ala Gln Ser Phe
50                  55                  60

Gln Gly Arg Val Thr Ile Thr Ala Asp Glu Ser Thr Ser Thr Ala His
65                  70                  75                  80

Met Glu Val Ser Ser Leu Arg Ser Glu Asp Thr Ala Val Tyr Tyr Cys
                85                  90                  95

Ala Ser Ser Arg Ile Tyr Asp His His Ile Gln Lys Gly Gly Tyr
                100                 105                 110

Tyr Asp Met Asp Val Trp Gly Gln Gly Thr Met Val Thr Val Ser Ser
            115                 120                 125

<210> SEQ ID NO 35
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gln Ala Val Leu Thr Gln Pro Ser Ser Val Ser Thr Pro Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 36
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
            35                  40                  45

Gly Gly Ile Ile Pro Ile Phe Asp Thr Gly Asn Ser Ala Gln Ser Phe
        50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                    85                  90                  95

Ala Ser Ser Ser Arg Ile Tyr Asp Tyr His Thr Ile Ala Tyr Tyr Asp
            100                 105                 110

<210> SEQ ID NO 37
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Gln Ala Val Leu Thr Gln Pro Ser Ser Val Ser Thr Pro Pro Gly Gln
1               5                   10                  15

Lys Val Thr Ile Ser Cys Ser Gly Ser Ser Asn Ile Gly Asn Asn
            20                  25                  30

Tyr Val Ser Trp Tyr Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 38
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
            35                  40                  45

Gly Gly Ile Ile Pro Ile Phe Asp Thr Gly Asn Ser Ala Gln Ser Phe
50                  55                  60

Gln Gly Arg Val Thr Ile Thr Ala Asp Glu Ser Thr Ser Thr Ala Tyr
65                  70                  75                  80

Met Lys Val Ser Ser Leu Arg Ser Asp Asp Thr Ala Val Tyr Tyr Cys
                85                  90                  95

Ala Ser Ser Ser Arg Ile Tyr Asp Tyr Ile Pro Gly Met Arg Pro Tyr
            100                 105                 110

Tyr Asp Met Asp Val Trp Gly Gln Gly Thr Met Val Thr Val Ser Ser
            115                 120                 125

<210> SEQ ID NO 39
<211> LENGTH: 110
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gln Ala Val Leu Thr Gln Pro Ser Ser Val Ser Thr Pro Pro Gly Gln
1               5                   10                  15

Lys Val Thr Ile Ser Cys Ser Gly Asn Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Arg Ser Gly Thr Leu Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 40
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Phe Asn Ser Ser Leu Ile Ala Tyr
            100                 105                 110

Tyr Asp Met Asp Val Trp Gly Gln Gly Thr Met Val Thr Val Ser Ser
        115                 120                 125

<210> SEQ ID NO 41
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Ala Val Leu Thr Gln Pro Ser Ser Val Ser Thr Pro Pro Gly Gln
1               5                   10                  15
```

Lys Val Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Thr Asp Tyr Tyr Cys Gly Thr Trp Asp Ser Ser Leu
                85                  90                  95

Ser Ala Trp Val Phe Ser Gly Gly Thr Lys Leu Thr Val Leu
            100                 105                 110

<210> SEQ ID NO 42
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Glu Val Gln Leu Val Gln Ser Gly Ala Glu Val Lys Lys Pro Gly Ser
1               5                   10                  15

Thr Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 43
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gln Ala Val Leu Thr Gln Pro Ser Ser Val Ser Thr Pro Pro Gly Gln
1               5                   10                  15

Lys Val Thr Ile Ser Cys Ser Gly Thr Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Trp Val Phe Gly Gly Gly Thr Lys Leu Thr Val Leu
            100                 105                 110

<210> SEQ ID NO 44
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Glu Val Gln Leu Val Gln Ser Gly Ala Glu Val Lys Lys Pro Gly Ser
  1               5                  10                  15

Ser Val Lys Val Ser Cys Lys Ala Ser Gly Gly Thr Phe Ser Thr Tyr
                 20                  25                  30

Gly Ile Ser Trp Val Arg Gln Ala Pro Gly Gln Gly Leu Glu Trp Ile
             35                  40                  45

Gly Gly Ile Ile Pro Ile Phe Gly Thr Gly Asn Ser Ala Gln Ser Phe
         50                  55                  60

Gln Gly Arg Val Thr Ile Thr Ala Asp Glu Ser Thr Ser Thr Ala Tyr
 65                  70                  75                  80

Met Glu Val Ser Ser Leu Arg Ser Asp Asp Thr Ala Val Tyr Tyr Cys
                 85                  90                  95

Ala Ser Ser Arg Ile Tyr Asp Phe Glu Pro Ser Leu Ile Tyr Tyr
                100                 105                 110

Tyr Asp Met Asp Val Trp Gly Gln Gly Thr Met Val Thr Val Ser Ser
            115                 120                 125

<210> SEQ ID NO 45
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gln Ala Val Leu Thr Gln Pro Ser Ser Val Ser Thr Pro Pro Gly Gln
  1               5                  10                  15

Lys Val Thr Ile Ser Cys Ser Gly Ser Ser Ser Asn Ile Gly Asn Asn
                 20                  25                  30

Tyr Val Ser Trp Tyr Gln Gln Leu Pro Gly Thr Ala Pro Lys Leu Leu
             35                  40                  45

Ile Tyr Asp Asn Asn Lys Arg Pro Ser Gly Ile Pro Asp Arg Phe Ser
         50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Trp Val Phe Gly Gly Gly Thr Lys Leu Thr Val Leu
            100                 105                 110

-continued

```
<210> SEQ ID NO 46
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 47
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asp Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Thr Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 48
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48
```

-continued

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 49
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 50
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

```
Gly Gly Ile Ile Pro Ile Phe Asp Thr Gly Asn Ser Ala Gln Ser Phe
        50                  55                  60

Gln Gly Arg Val Ala Ile Thr Ala Asp Glu Ser Thr Ser Thr Ala Tyr
 65                  70                  75                  80

Met Glu Val Ser Ser Leu Arg Ser Asp Asp Thr Ala Val Tyr Tyr Cys
                 85                  90                  95

Ala Ser Ser Ser Arg Ile Tyr Asp Leu Asn Pro Ser Leu Thr Ala Tyr
                100                 105                 110

Tyr Asp Met Asp Val Trp Gly Gln Gly Thr Met Val Thr Val Ser Ser
            115                 120                 125
```

<210> SEQ ID NO 51
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

```
Gln Ala Val Leu Thr Gln Pro Ser Ser Val Ser Thr Pro Pro Gly Gln
 1               5                  10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Gly Leu
                 85                  90                  95

Ser Ala Trp Val Phe Gly Gly Gly Thr Lys Leu Thr Val Leu
                100                 105                 110
```

<210> SEQ ID NO 52
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

```
Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Thr Tyr
                20                  25                  30

Gly Ile Ser Trp Val Arg Gln Ala Pro Gly Gln Gly Leu Glu Trp Ile
            35                  40                  45

Gly Gly Ile Ile Pro Ile Phe Asp Thr Ser Asn Ser Ala Gln Ser Phe
        50                  55                  60

Gln Gly Arg Val Thr Ile Thr Ala Asp Glu Ser Thr Ser Thr Ala Tyr
 65                  70                  75                  80

Met Glu Val Ser Ser Leu Arg Ser Asp Asp Thr Ala Val Tyr Tyr Cys
                 85                  90                  95

Ala Ser Ser Ser Arg Ile Tyr Asp Phe Arg Thr Leu Tyr Ser Thr Tyr
```

```
            100                 105                 110

Tyr Asp Met Asp Val Trp Gly Gln Gly Thr Met Val Thr Val Ser Ser
        115                 120                 125

<210> SEQ ID NO 53
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Ser Asp Arg Phe Ser
50                  55                  60

Gly Ser Lys Ser Gly Thr Ser Ala Thr Leu Gly Ile Ala Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 54
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 55
<211> LENGTH: 110
<212> TYPE: PRT
<213> ORGANISM: Artificial Sequence
```

<220> FEATURE:
<221> NAME/KEY: source
<223> OTHER INFORMATION: /note="Description of Artificial Sequence:
      Synthetic polypeptide"

<400> SEQUENCE: 55

Gln Ala Val Leu Thr Gln Pro Ser Ser Val Ser Thr Pro Pro Gly Gln
1               5                   10                  15

Glu Val Thr Ile Ser Cys Ser Gly Ser Ser Thr Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 56
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Glu Val Gln Leu Val Gln Ser Gly Ala Glu Val Lys Lys Pro Gly Ser
1               5                   10                  15

Ser Val Arg Ile Ser Cys Lys Ala Ser Gly Gly Thr Phe Ser Thr Tyr
                20                  25                  30

Gly Val Ser Trp Val Arg Gln Ala Pro Gly Gln Gly Leu Glu Trp Ile
            35                  40                  45

Gly Gly Ile Ile Pro Ile Phe Asp Thr Gly Asn Ser Ala Gln Ser Phe
50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 57
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Gln Ala Val Leu Thr Gln Pro Ser Ser Val Ser Thr Pro Pro Gly Gln
1               5                   10                  15

Lys Val Thr Ile Ser Cys Ser Gly Ser Ser Asn Ile Gly Asn Asn
                 20                  25                  30

Tyr Val Ser Trp Tyr Gln Gln Leu Pro Gly Thr Ala Pro Lys Leu Leu
             35                  40                  45

Ile Tyr Asp Asn Asn Lys Arg Pro Ser Gly Val Pro Asp Arg Phe Ser
 50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Ser Ser Leu
                 85                  90                  95

Ser Ala Trp Val Phe Gly Gly Gly Thr Lys Leu Thr Val Leu
            100                 105                 110

<210> SEQ ID NO 58
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

Glu Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ala Tyr
                 20                  25                  30

Gly Ile Ser Trp Val Arg Gln Ala Pro Gly Gln Gly Leu Glu Trp Ile
             35                  40                  45

Gly Gly Ile Ile Pro Ile Phe Asn Thr Gly Asn Ser Ala Gln Ser Phe
 50                  55                  60

Gln Gly Arg Val Thr Ile Thr Ala Asp Glu Ser Thr Ser Thr Ala Tyr
 65                  70                  75                  80

Met Glu Val Ser Ser Leu Arg Ser Asp Asp Thr Ala Val Tyr Tyr Cys
                 85                  90                  95

Ala Ser Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val
        115                 120                 125

<210> SEQ ID NO 59
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Gln Ala Val Leu Thr Gln Pro Ser Ser Val Ser Thr Pro Pro Gly Gln
 1               5                  10                  15

Lys Val Thr Val Ser Cys Ser Gly Ser Ser Ser Asn Ile Gly Asn Asn
                 20                  25                  30

Tyr Val Ser Trp Tyr Gln Gln Leu Pro Gly Thr Ala Pro Lys Leu Leu
             35                  40                  45

Ile Tyr Asp Asn Asn Lys Arg Pro Ser Gly Ile Pro Asp Arg Phe Ser
 50                  55                  60

Gly Ser Lys Ser Gly Thr Ser Ala Thr Leu Gly Ile Thr Gly Leu Gln

```
                65                  70                  75                  80
Thr Gly Asp Glu Ala Asp Tyr Tyr Cys Gly Thr Trp Asp Ser Ser Leu
                    85                  90                  95

Ser Ala Trp Val Phe Gly Gly Gly Thr Lys Leu Thr Val Leu
                100                 105                 110

<210> SEQ ID NO 60
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
                20                  25                  30

Gly Ile Ser Trp Val Arg Gln Ala Pro Gly Gln Gly Leu Glu Trp Ile
            35                  40                  45

Gly Gly Ile Ile Pro Ile Phe Asp Thr Gly Asn Ser Ala Gln Ser Phe
        50                  55                  60

Gln Asp Arg Val Thr Ile Thr Ala Asp Glu Ser Thr Ser Thr Ala Tyr
65                  70                  75                  80

Met Glu Val Gly Ser Leu Arg Ser Asp Asp Thr Ala Val Tyr Tyr Cys
                85                  90                  95

Ala Ser Ser Arg Ile Tyr Asp Leu Asn Pro Ser Leu Thr Ala Tyr
                100                 105                 110

Tyr Asp Met Asp Val Trp Gly His Gly Thr Met Val Thr Val Ser Ser
            115                 120                 125

<210> SEQ ID NO 61
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
                100                 105                 110

<210> SEQ ID NO 62
```

<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 62

```
Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Val Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Met Ile Ser Ser Leu Gln Pro Tyr
            100                 105                 110

Tyr Asp Met Asp Val Trp Gly Gln Gly Thr Met Val Thr Val Ser Ser
        115                 120                 125
```

<210> SEQ ID NO 63
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 63

```
Gln Ala Val Leu Thr Gln Pro Ser Ser Val Ser Thr Pro Pro Gly Gln
1               5                   10                  15

Lys Ala Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110
```

<210> SEQ ID NO 64
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Phe His Leu Ala Asn Lys Gly Tyr
            100                 105                 110

Tyr Asp Met Asp Val Trp Gly Gln Gly Thr Met Val Thr Val Ser Ser
        115                 120                 125

<210> SEQ ID NO 65
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Gln Ala Val Leu Thr Gln Pro Ser Ser Val Ser Thr Pro Pro Gly Gln
1               5                   10                  15

Lys Ala Thr Ile Ser Cys Ser Gly Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Asp Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 66
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 66

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Gly Thr Gly Asn Ser Ala Gln Ser Phe

```
                50                  55                  60
Gln Gly Arg Val Thr Ile Thr Ala Asp Glu Ser Thr Ser Thr Ala Tyr
 65                  70                  75                  80

Met Glu Val Ser Ser Leu Arg Ser Asp Asp Thr Ala Val Tyr Tyr Cys
                    85                  90                  95

Ala Ser Ser Arg Ile Tyr Asp His His Asn His Val Gly Gly Tyr
                100                 105                 110

Tyr Asp Met Asp Val Trp Gly Gln Gly Thr Met Val Thr Val Ser Ser
            115                 120                 125
```

<210> SEQ ID NO 67
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

```
Gln Ala Val Leu Thr Gln Pro Ser Ser Val Ser Thr Pro Pro Gly Gln
 1               5                   10                  15

Lys Val Thr Ile Ser Cys Ser Gly Ser Ser Asn Ile Gly Asn Asn
                20                  25                  30

Tyr Ala Ser Trp Tyr Gln Gln Leu Pro Gly Thr Ala Pro Lys Leu Leu
                35                  40                  45

Ile Tyr Asp Asn Asn Lys Arg Pro Ser Gly Ile Pro Asp Arg Phe Ser
            50                  55                  60

Gly Ser Lys Ser Gly Thr Ser Ala Thr Leu Gly Ile Thr Gly Leu Gln
 65                  70                  75                  80

Thr Gly Asp Glu Ala Asp Tyr Tyr Cys Gly Thr Trp Asp Gly Ser Leu
                    85                  90                  95

Ser Ala Trp Val Phe Gly Gly Gly Thr Lys Leu Thr Val Leu
                100                 105                 110
```

<210> SEQ ID NO 68
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

```
Glu Val Gln Leu Val Gln Ser Gly Ala Glu Val Lys Lys Pro Gly Ser
 1               5                   10                  15

Ser Ala Lys Val Ser Cys Lys Ala Ser Gly Gly Thr Phe Ser Thr Tyr
                20                  25                  30

Gly Ile Ser Trp Val Arg Gln Ala Pro Gly Gln Gly Leu Glu Trp Ile
                35                  40                  45

Gly Gly Ile Ile Pro Ile Phe Asp Thr Gly Asn Ser Ala Gln Ser Phe
            50                  55                  60

Gln Gly Arg Val Thr Ile Thr Ala Asp Glu Ser Thr Ser Thr Ala Tyr
 65                  70                  75                  80

Met Glu Val Ser Ser Leu Arg Ser Asp Asp Thr Ala Val Tyr Tyr Cys
                    85                  90                  95

Ala Ser Ser Arg Ile Tyr Asp Leu Asn Pro Ser Leu Thr Ala Tyr
                100                 105                 110
```

Tyr Asp Met Asp Val Trp Gly Gln Gly Thr Met Val Thr Val Ser Ser
            115                 120                 125

<210> SEQ ID NO 69
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 69

Gln Ala Val Leu Thr Gln Pro Ser Ser Val Ser Thr Pro Pro Gly Gln
1               5                   10                  15

Lys Val Thr Ile Ser Cys Ser Gly Ser Asn Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val
            100                 105

<210> SEQ ID NO 70
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 70

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 71
<211> LENGTH: 110
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 71

Gln Ala Val Leu Thr Gln Pro Ser Ser Val Ser Thr Pro Pro Gly Gln
1               5                   10                  15

Lys Val Thr Ile Ser Cys Ser Gly Ser Ser Asn Ile Glu Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 72
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 72

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Arg Leu Glu Trp Ile
        35                  40                  45

Gly Gly Ile Ile Pro Ile Phe Asp Thr Gly Asn Ser Ala Gln Ser Phe
50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Ala Thr Thr Gly Leu Thr Pro Tyr
            100                 105                 110

Tyr Asp Met Asp Val Trp Gly Gln Gly Thr Met Val Thr Val Ser Ser
        115                 120                 125

<210> SEQ ID NO 73
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 73

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
```

```
                    20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
        50                  55                  60

Gly Ser Lys Ser Gly Thr Ser Ala Thr Leu Gly Ile Thr Gly Leu Arg
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 74
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

Glu Val Gln Leu Val Gln Ser Gly Ala Glu Val Arg Lys Pro Gly Ser
1               5                   10                  15

Ser Val Lys Val Ser Cys Lys Ala Tyr Gly Gly Thr Phe Ser Thr Tyr
            20                  25                  30

Gly Ile Ser Trp Val Arg Gln Ala Pro Gly Gln Gly Leu Glu Trp Val
        35                  40                  45

Gly Gly Ile Ile Pro Ile Phe Asp Thr Arg Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Ser Arg Ile Tyr Asp Met Val Ser Thr Leu Ile Pro Tyr
            100                 105                 110

Tyr Asp Met Asp Val Trp Gly Gln Gly Thr Met Val Thr Val Ser Ser
        115                 120                 125

<210> SEQ ID NO 75
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80
```

```
Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 76
<211> LENGTH: 126
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 76

Glu Val Gln Leu Val Gln Ser Gly Ala Glu Val Lys Lys Pro Gly Ser
1               5                   10                  15

Ser Val Arg Val Ser Cys Lys Ala Ser Gly Gly Thr Phe Ser Thr Tyr
            20                  25                  30

Gly Ile Ser Trp Val Arg Gln Ala Pro Gly Gln Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Ala His Leu Gln Ala Tyr Tyr Asp
            100                 105                 110

Met Asp Val Trp Gly Gln Gly Thr Met Val Thr Val Ser Ser
        115                 120                 125

<210> SEQ ID NO 77
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Pro Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Arg Asp Ser Ser Leu
                85                  90                  95

Ser Ala Trp Val Phe Gly Gly Gly Thr Lys Leu Thr Val Leu
            100                 105                 110

<210> SEQ ID NO 78
<211> LENGTH: 128
```

-continued

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 78

Glu Val Gln Leu Val Gln Ser Gly Ala Glu Ala Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Arg Gly Leu Glu Trp Ile
        35                  40                  45

Gly Gly Ile Ile Pro Ile Phe Asp Thr Gly Asn Ser Ala Gln Ser Phe
    50                  55                  60

Gln Gly Arg Val Ala Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Ala His Leu Asn His His Gly Tyr
            100                 105                 110

Tyr Asp Met Asp Val Trp Gly Gln Gly Thr Met Val Thr Val Ser Ser
        115                 120                 125

<210> SEQ ID NO 79
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Gln Ala Val Leu Thr Gln Pro Ser Ser Val Ser Thr Pro Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Ala Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110

<210> SEQ ID NO 80
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Glu Val Gln Leu Val Gln Ser Gly Ala Val Val Lys Lys Pro Gly Ser
```

-continued

```
                1               5                  10                 15
            Ser Val Lys Val Ser Cys Lys Ala Ser Gly Gly Thr Phe Ser Thr Tyr
                        20                  25                 30

Gly Ile Ser Trp Val Arg Gln Ala Pro Gly Gln Gly Leu Glu Trp Ile
                        35                  40                 45

Gly Gly Ile Ile Pro Ile Phe Asp Thr Gly Ser Ser Ala Gln Ser Phe
                        50                  55                 60

Gln Gly Arg Val Thr Ile Thr Ala Asp Glu Ser Thr Ser Thr Ala Tyr
             65                 70                  75                 80

Met Glu Val Ser Ser Leu Arg Ser Asp Asp Thr Ala Val Tyr Tyr Cys
                            85                 90                  95

Ala Ser Ser Arg Ile Tyr Asp Leu Asn Pro Ser Leu Thr Ala Tyr
                            100                105                110

Tyr Asp Met Asp Val Trp Gly Gln Gly Thr Met Val Thr Val Ser Ser
                        115                 120                125
```

<210> SEQ ID NO 81
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 81

```
            Gln Ala Val Leu Thr Gln Pro Ser Ser Val Ser Thr Pro Pro Gly Gln
             1               5                  10                 15

Lys Val Thr Ile Ser Cys Ser Gly Ser Ser Ser Asn Thr Gly Asn Asn
                        20                  25                 30

Tyr Val Ser Trp Tyr Gln Gln Leu Ser Gly Thr Ala Pro Lys Leu Leu
                        35                  40                 45

Ile Tyr Asp Asn Asn Lys Arg Pro Ser Gly Ile Pro Asp Arg Phe Ser
                        50                  55                 60

Gly Ser Lys Ser Gly Thr Ser Ala Thr Leu Gly Ile Thr Gly Leu Gln
             65                 70                  75                 80

Thr Gly Asp Glu Ala Asp Tyr Tyr Cys Gly Thr Trp Asp Ser Ser Leu
                            85                 90                  95

Ser Ala Trp Val Phe Gly Gly Gly Thr Lys Leu Thr Val Leu
                        100                 105                110
```

<210> SEQ ID NO 82
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 82

```
            Glu Met Gln Leu Val Gln Ser Gly Ala Glu Val Lys Lys Pro Gly Ser
             1               5                  10                 15

Ser Val Lys Val Ser Cys Lys Ala Ser Gly Gly Thr Phe Ser Thr Tyr
                        20                  25                 30

Gly Ile Ser Trp Val Arg Gln Ala Pro Gly Gln Gly Leu Glu Trp Ile
                        35                  40                 45

Gly Gly Ile Ile Pro Ile Phe Asp Thr Gly Asn Ser Ala Gln Ser Phe
                        50                  55                 60
```

Gln Gly Arg Val Thr Ile Thr Ala Asp Glu Ser Thr Ser Thr Ala Tyr
65                  70                  75                  80

Met Glu Val Ser Ser Leu Arg Ser Asp Asp Thr Ala Val Tyr Tyr Cys
                85                  90                  95

Ala Ser Ser Arg Ile Tyr Asp Phe Asn Ser Ala Leu Ile Ser Tyr
            100                 105                 110

Tyr Asp Met Asp Val Trp Gly Gln Gly Thr Met Val Thr Val Ser Ser
        115                 120                 125

<210> SEQ ID NO 83
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

Gln Ala Val Leu Thr Gln Pro Ser Ser Val Ser Pro Pro Gly Gln
1               5                   10                  15

Lys Val Thr Ile Ser Cys Ser Gly Ser Ser Ser Asn Ile Gly Asn Asn
                20                  25                  30

Tyr Val Ser Trp Tyr Gln Gln Leu Pro Gly Thr Ala Pro Lys Leu Leu
            35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val
            100                 105

<210> SEQ ID NO 84
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Ala Tyr His
                20                  25                  30

Tyr Leu His Trp Val Arg Gln Ala Pro Gly Gln Gly Leu Glu Trp Met
            35                  40                  45

Gly Gly Ile Ile Pro Ile Phe Gly Thr Thr Asn Tyr Ala Gln Arg Phe
        50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ala Asp Tyr Val Trp Gly Ser Tyr Arg Pro Asp Trp Tyr Phe
            100                 105                 110

Asp Leu Trp Gly Arg Gly Thr Met Val Thr Val Ser Ser
            115                 120                 125

<210> SEQ ID NO 85
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Arg Leu Pro Gly Ala Ala Pro Gln Leu Leu
        35                  40                  45

Ile Tyr Asn Asn Asp Gln Arg Pro Ser Gly Ile Pro Asp Arg Phe Ser
    50                  55                  60

Gly Ser Lys Ser Gly Thr Ser Gly Ser Leu Val Ile Ser Gly Leu Gln
65                  70                  75                  80

Ser Glu Asp Glu Ala Asp Tyr Tyr Cys Ala Ser Trp Asp Asp Ser Leu
                85                  90                  95

Asn Gly Arg Val Phe Gly Gly Gly Thr Lys Leu Thr Val Leu
            100                 105                 110

<210> SEQ ID NO 86
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Gln Met Gln Leu Val Gln Ser Gly Ala Glu Val Lys Lys Thr Gly Ser
1               5                   10                  15

Ser Val Lys Val Ser Cys Lys Ala Ser Gly His Thr Phe Ala Tyr His
            20                  25                  30

Tyr Leu His Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Arg Phe
    50                  55                  60

Gln Asp Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ala Asp Tyr Ala Trp Glu Ser Tyr Gln Pro Pro Gln Ile Asn
            100                 105                 110

Gly Val Trp Gly Arg Gly Thr Met Val Thr Val Ser Ser
        115                 120                 125

<210> SEQ ID NO 87
<211> LENGTH: 110
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic polypeptide"

<400> SEQUENCE: 87

Gln Ser Val Leu Thr Gln Pro Pro Ser Val Ser Ala Ala Pro Gly Gln
1               5                   10                  15

Lys Val Thr Ile Thr Cys Ser Gly Ser Thr Ser Asn Ile Gly Asn Asn
            20                  25                  30

Tyr Val Ser Trp Tyr Gln Gln His Pro Gly Lys Ala Pro Lys Leu Met
        35                  40                  45

Ile Tyr Asp Val Ser Lys Arg Pro Ser Gly Val Pro Asp Arg Phe Ser
    50                  55                  60

Gly Ser Lys Ser Gly Asn Ser Ala Ser Leu Asp Ile Ser Gly Leu Gln
65                  70                  75                  80

Ser Glu Asp Glu Ala Asp Tyr Tyr Cys Ala Ala Trp Asp Asp Ser Leu
                85                  90                  95

Ser Glu Phe Phe Phe Gly Thr Gly Thr Lys Leu Thr Val Leu
                100                 105                 110

<210> SEQ ID NO 88
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 88

Phe Gly Ala Phe Thr
1               5

<210> SEQ ID NO 89
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 89

Gly Ile Ile Pro Ile Phe Gly Leu Thr Asn Leu Ala Gln Asn Phe Gln
1               5                   10                  15

Gly

<210> SEQ ID NO 90
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 90

Ser Ser Arg Ile Tyr Asp Leu Asn Pro Ser Leu Thr Ala Tyr Tyr Asp
1               5                   10                  15

Met Asp Val

<210> SEQ ID NO 91
<211> LENGTH: 13
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 91

Ser Gly Ser Ser Ser Asp Ile Gly Asn Asn Tyr Val Ser
1               5                   10

<210> SEQ ID NO 92
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 92

Asp Asn Asn Lys Arg Pro Ser
1               5

<210> SEQ ID NO 93
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 93

Gly Thr Trp Asp Ser Ser Leu Ser Ala Trp Val
1               5                   10

<210> SEQ ID NO 94
<211> LENGTH: 128
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 94

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Tyr
            20                  25                  30

Gly Ile Ser Trp Val Arg Gln Ala Pro Gly Gln Cys Leu Glu Trp Met
        35                  40                  45

Gly Gly Ile Ile Pro Ile Phe Asp Thr Gly Asn Ser Ala Gln Ser Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 95
```

```
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95
```

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Cys Gly Thr Lys Leu Thr Val Leu
            100                 105                 110

```
<210> SEQ ID NO 96
<211> LENGTH: 125
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96
```

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Pro Tyr His
            20                  25                  30

Tyr Leu His Trp Val Arg Gln Ala Pro Gly Gln Gly Leu Glu Trp Met
        35                  40                  45

Gly Gly Ile Ile Pro Ile Phe Gly Thr Thr Asn Tyr Ala Gln Arg Phe
50                  55                  60

Gln Asp Arg Val Thr Ile Thr Ala Asp Glu Ser Thr Ser Thr Ala Tyr
65                  70                  75                  80

Met Glu Phe Ser Ser Leu Arg Ser Glu Asp Thr Ala Val Tyr Tyr Cys
                85                  90                  95

Ala Ser Ala Asp Tyr Val Trp Glu Ser Tyr His Pro Ala Thr Ser Leu
            100                 105                 110

Ser Leu Trp Gly Arg Gly Thr Met Val Thr Val Ser Ser
        115                 120                 125

```
<210> SEQ ID NO 97
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 97
```

```
Gln Ser Val Leu Thr Gln Pro Pro Ser Val Ser Ala Ala Pro Gly Gln
1               5                   10                  15

Lys Val Thr Ile Ser Cys Pro Gly Ser Thr Ser Asn Ile Gly Asn Asn
            20                  25                  30

Tyr Val Ser Trp Tyr Gln Gln Arg Pro Gly Lys Ala Pro Lys Leu Met
        35                  40                  45

Ile Tyr Asp Val Ser Lys Arg Pro Ser Gly Val Pro Asp Arg Phe Ser
    50                  55                  60

Gly Ser Lys Ser Gly Asn Ser Ala Ser Leu Asp Ile Ser Glu Leu Gln
65                  70                  75                  80

Ser Glu Asp Glu Ala Asp Tyr Tyr Cys Ala Ala Trp Asp Asp Ser Leu
                85                  90                  95

Ser Glu Phe Leu Phe Gly Thr Gly Thr Lys Leu Thr Val Leu
            100                 105                 110

<210> SEQ ID NO 98
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Gly Gly Gly Gly Ser Gly Gly Gly Gly Ser
1               5                   10

<210> SEQ ID NO 99
<211> LENGTH: 2205
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 99
ctgcccgccc aggtggcctt tacccttat gctcctgagc ccggctctac ctgccggctg      60
agagagtact acgaccagac cgcccagatg tgctgctcca agtgctctcc tggccagcac     120
gccaaggtgt tctgcaccaa gacctccgat accgtgtgcg actcctgcga ggactccacc    180
tacacccagc tgtggaactg ggtgcccgag tgcctgtcct gcggctccag atgttcctcc    240
gaccaggtgg aaacccaggc ctgcaccaga gagcagaacc ggatctgcac ctgtcggcct    300
ggctggtact gcgccctgtc taagcaggaa ggctgcagac tgtgcgcccc tctgcggaag    360
tgtagacctg gctttggcgt ggccagaccc ggcaccgaga catctgatgt cgtgtgcaag    420
ccttgcgccc ctggcacctt ctccaacacc acctcctcca ccgacatctg ccggcctcac    480
cagatctgca acgtggtggc catccctggc aacgcctcta tggacgccgt gtgcacctct    540
acctccccca ccagaagtat ggcccctggc gctgtgcatc tgcccagcc tgtgtctacc    600 agatcccagc acacccagcc cacccctgag ccttctaccg ccccttctac cagcttcctg    660
ctgcctatgg gcctagccc tcctgctgag ggatctacag cgacgagcc caagtcctgc    720 gacaagaccc acacctgtcc cccttgtcct gcccctgaac tgctgggcgg accttccgtg    780
ttcctgttcc ccccaaagcc caaggacacc ctgatgatca gccggacccc tgaagtgacc    840
tgcgtggtgg tggatgtgtc ccacgaggat cccgaagtga agttcaattg gtacgtggac    900
ggcgtggaag tgcacaacgc caagaccaag cccagagagg aacagtacaa ctccacctac    960
```

```
cgggtggtgt ccgtgctgac cgtgctgcac caggattggc tgaacggcaa agagtacaag    1020
tgcaaggtgt ccaacaaggc cctgcctgcc cccatcgaaa agaccatctc caaggccaag    1080
ggccagcccc gggaacccca ggtgtacaca ctgcccccta gccgggaaga gatgaccaag    1140
aaccaggtgt ccctgacctg tctcgtgaag ggcttctacc cctccgatat cgccgtggaa    1200
tgggagtcca acggccagcc tgagaacaac tacaagacca cccccctgt gctggactcc     1260 gacggctcat tcttcctgta ctccaagctg acagtggaca agtcccggtg gcagcagggc    1320
aacgtgttct cctgctccgt gatgcacgag gccctgcaca accactacac ccagaagtcc    1380
ctgtccctga gccctggaaa aggcggcgga ggatctggcg gaggcggatc tcaggtgcag    1440
ctggtgcagt ctggcgctga agtgaagaaa cccggctcct ccgtgaaggt gtcctgcaag    1500
gcttctggcg gcaccttctc tacctacggc atctcctggg tgcgacaggc ccctggccag    1560
tgcctggaat ggatgggcgg catcatcccc atcttcgaca ccggcaactc cgcccagagc    1620
ttccagggca gagtgaccat caccgccgac gagtctacct ccaccgccta catggaactg    1680
tcctccctgc ggagcgagga caccgccgtg tactactgcg cccggtcctc tcggatctac    1740
gacctgaacc cttccctgac cgcctactac gacatggacg tgtggggcca gggcacaatg    1800
gtcaccgtgt catctggtgg tggcggctct ggtggcggag gaagtggggg aggggttct    1860 gggggggag gatctcagtc tgtgctgacc cagcctcctt ccgtgtctgc tgccccaggc    1920
cagaaagtga caatctcctg cagcggctcc agctccaaca tcggcaacaa ctacgtgtcc    1980
tggtatcagc agctgcccgg caccgctccc aaactgctga tctacgataa caacaagcgg    2040
ccctccggca tccccgacag attctccggc tctaagtccg gcacctctgc caccctgggc    2100
atcaccggac tgcagacagg cgacgaggcc gactactact gtggcacctg ggactcctcc    2160
ctgtccgctt gggtgttcgg ctgcggcacc aaactgactg tgctg                   2205
```

COMPOUNDS AND METHODS FOR TREATING PAIN

RELATED APPLICATIONS

This application is a continuation of U.S. application Ser. No. 14/612,137, filed Feb. 2, 2015, which claims the benefit of U.S. Provisional Application No. 61/934,828, filed Feb. 2, 2014. The specifications of each of the foregoing applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 20, 2017, is named 1848081-054-102_Seq.txt and is 129,631 bytes in size.

BACKGROUND

Pain is one of the most common symptoms for which medical assistance is sought and is the primary complaint of half of all patients visiting a physician. Despite the existence and widespread use of numerous pain medications, the elimination of pain, particularly chronic pain, has been without success. Thus, the burden on society remains high. Various studies estimate that pain results in 50 million workdays lost each year and $61.2 billion in lost productivity. For chronic pain sufferers, only about half are able to manage pain with the available prescribed treatment options. And, the total prescription pain medication market is approximately $25 billion per year. As is suggested by these data, a large need remains for safe and effective novel analgesics.

Therapeutic agents that reduce the tissue levels or inhibit the effects of secreted nerve growth factor (NGF or beta-NGF) have the potential to be just such novel analgesics. NGF plays a well-known pivotal role in the development of the nervous system; however, NGF is also a well-validated target for pain as it causes pain in animals and humans. In adults, NGF, in particular, promotes the health and survival of a subset of central and peripheral neurons (Huang & Reichardt, Ann. Rev. Neurosci. 24:677-736 (2001)). NGF also contributes to the modulation of the functional characteristics of these neurons and exerts tonic control over the sensitivity, or excitability, of sensory pain receptors called nociceptors (Priestley et al., Can. J. Physiol. Pharmacol. 80:495-505 (2002); Bennett, Neuroscientist 7:13-17 (2001)). Nociceptors sense and transmit to the central nervous system the various noxious stimuli that give rise to perceptions of pain (nociception). NGF receptors are located on nociceptors. The expression of NGF is increased in injured and inflamed tissue and is upregulated in human pain states. Thus, because of NGF's role in nociception, NGF-binding agents that reduce levels of NGF possess utility as analgesic therapeutics.

Subcutaneous injections of NGF itself produce pain in humans and animals. Injected NGF causes a rapid thermal hyperalgesia, followed by delayed thermal hyperalgesia and mechanical allodynia (Petty et al., Ann. Neurol. 36:244-46 (1994); McArthur et al., Neurology 54:1080-88 (2000)). Endogenously secreted NGF is similarly pro-nociceptive. Tissue-injury-induced release of NGF and its subsequent action in the periphery plays a major role in the induction of thermal hyperalgesia through the process of "peripheral sensitization" (Mendell & Arvanian, Brain Res. Rev. 40:230-39 (2002)). Tissue injury promotes the release of pro-nociceptive and pro-inflammatory cytokines, which, in turn, induce the release of NGF from keratinocytes and fibroblasts. This released NGF acts directly on nociceptors to induce painful or nociceptive states within minutes of the noxious insult. Thus, NGF also acts indirectly to induce and maintain nociceptive/pain states in a feed-forward release. It triggers mast cell degranulation, releasing pro-nociceptive agents such as histamine and serotonin and, importantly, more NGF, and can also stimulate sympathetic nerve terminals to release pro-nociceptive neurotransmitters, such as noradrenaline (Ma & Woolf, Neuroreport. 8:807-10 (1997)).

Tissue levels of NGF are elevated in complete Freund's adjuvant (CFA)- and carrageenan-injected animals (Ma & Woolf, Neuroreport. 8:807-10 (1997); Amann & Schuligoi, Neurosci. Lett. 278:173-78 (2000)). NGF potentiates DRG (dorsal root ganglia) capsaicin response in the rat. Increased levels of NGF have been documented in patients suffering from rheumatoid arthritis (Aloe & Tuveri, Clin. Exp. Rheumatol. 15:433-38 (1997)) or cystitis (Lowe et al., Br. J. Urol. 79:572-77 (1997)). In rodents, peripheral nerve injury increases the expression of NGF mRNA in macrophages, fibroblasts, and Schwann cells (Heumann et al., J. Cell Biol. 104:1623-31 (1987)). Over-expression of NGF in transgenic mice results in enhanced neuropathic pain behavior following nerve injury above that of wild-type mice (Ramer et al., Pain, Supp. 6:S111-20 (1998)). Over hours and 15 days, elevated NGF levels play a role in promoting "central sensitization"—the enhancement of neurotransmission at synapses in the nociceptive pathways of the spinal cord. Central sensitization results in persistent and chronic hyperalgesia and allodynia. This process is thought to involve internalization of complexes of NGF and its high affinity receptor, tyrosine receptor kinase A (trkA). Retrograde transport of these complexes to nociceptor cell bodies in the DRG potentiates secretion of nociceptive neuropeptides, e.g., substance P, or calcitonin gene related peptide (CGRP), protein kinase C (PKC) activation, and N-methyl-D-aspartate (NMDA) receptor activation in the dorsal horn of the spinal cord (Sah et al., Nat. Rev. Drug Disc. 2:460-72 (2003))—all processes that promote the sensitization of the nociceptive pathways. NGF also plays a role in the up-regulation and re-distribution of voltage-dependent and ligand-gated ion channels, including sodium channel subtypes and the capsaicin receptor, transient receptor potential cation channel subfamily V member 1 (TRPV1) (Mamet et al., J. Biol. Chem. 278:48907-13 (1999); Fjell et al., J. Neurosci. Res. 57:39-47 (1999); Priestley et al., Can. J. Physiol. Pharmacol. 80:495-505 (2002)). The altered activities and/or expression of transmitters, receptors, and ion channels underlie the increased sensitivity and excitability of nociceptors associated with neuropathic pain states.

NGF-induced nociception/pain is mediated by the high affinity NGF receptor, trkA (tyrosine receptor kinase A) (Sah, et al., Nat. Rev. Drug Disc. 2:460-72 (2003)). About 40-45% of nociceptor cell bodies in DRGs express trkA. These are the cell bodies of the small diameter fibers, or C-fibers, that also express the secreted pro-nociceptive peptides, substance P and CGRP. These fibers terminate in laminae I and II of the dorsal horn, where they transfer to the central nervous system the noxious stimuli sensed by peripheral nociceptors. Mutations or deletions in the trkA gene produce a phenotype characterized by loss of pain sensation both in humans (Indo, Clin. Auton. Res. 12 (Supp 1):I120-I32 (2002)) and in trkA knock-out mice (de Castro et al., Eur. J. Neurosci. 10:146-52 (1998)). Significantly, the expression of trkA is up-regulated in animals subjected to models of arthritic (Pozza et al., J. Rheumatol. 27:1121-27 (2000)) or cystitic pain (Qiao & Vizzard, J. Comp. Neurol. 454:200-11 (2002)), or the inflammatory pain induced by injection of CFA or carrageenan into the paw (Cho et al., Brain Res. 716:197-201 (1996)).

NGF also binds to the p75 neurotrophin receptor (p75NTR). The role of p75NTR is dependent on its cellular environment and the presence of other receptors with which it is believed to play an accessory or co-receptor function. Interaction between trkA and p75NTR results in the formation of high affinity binding sites for NGF. The importance of such receptor interactions in NGF-mediated pain signaling is not clear, but recent studies have implicated the p75NTR in cellular processes that may be relevant (Zhang & Nicol, Neurosci. Lett. 366:187-92 (2004)). However, while p75NTR knockout mice display elevated thresholds to noxious stimuli, they remain responsive to the hyperalgesic effects of NGF, suggesting that trkA receptors alone are sufficient to mediate these effects (Bergmann et al., Neurosci. Lett. 255:87-90 (1998)).

NGF blockade produces step-change efficacy versus NSAIDs in chronic nociceptive pain, e.g., in osteoarthritis, (OA) and in chronic lower back pain. A number of therapeutic antibody candidates targeting NGF are in various stages of preclinical and clinical development. Such antibodies include, e.g., Tanezumab (PF-4383119; Pfizer), which is a humanized antibody in an IgG2 format; SAR164877/REGN475 (Sanofi-Aventis/Regeneron Pharmaceuticals), which is a human antibody in an IgG4 format; AMG 403 (Amgen/Johnson & Johnson), which is a human antibody in an IgG2 format; PG110 (PanGenetics/Abbott), which is a humanized antibody in an IgG4 format. Another therapeutic antibody candidate is disclosed in WO 2006/077441, which relates to NGF antibodies and to methods of treating diseases or disorders in which NGF plays a role with the disclosed antibodies. MEDI-578 is a human antibody in an IgG4 format. Despite the development of these candidates, there remains a need to provide analgesic relief for a broader range of pain conditions through an NGF-binding agent that has robust efficacy and improved safety profiles.

Tumor necrosis factor-alpha (TNFα), also called cachectin, is a pleiotropic cytokine with a broad range of biological activities including cytotoxicity, immune cell proliferation, inflammation, tumorigenesis, and viral replication. Kim et al., J. Mol. Biol. 374, 1374 (2007). TNFα is first produced as a transmembrane protein (tm TNFα), which is then cleaved by a metalloproteinase to a soluble form (sTNFα). Wallis, Lancet Infect. Dis. 8(10): 601 (2008). TNFα (~17 kDa) exists as a rigid homotrimeric molecule, which binds to cell-surface TNF Receptor 1 or TNF Receptor 2, inducing receptor oligomerization and signal transduction.

Inflammatory cytokines, and in particular TNFα, are known to have a role in the generation of hyperalgesia. Leung, L., and Cahill, C M., J. Neuroinflammation 7:27 (2010). Some preliminary data has shown that TNFα inhibitors may be useful in the control of neuropathic pain. See, e.g., Sommer C, et al., J. Peripher. Nerv. Syst. 6:67-72 (2001), Cohen et al, A&A February 2013, 116, 2, 455-462, Genevay et al., Ann Rheum Dis 2004, 63, 1120-1123. The results from clinical studies testing TNFα inhibitors as a single therapy in the treatment of neuropathic pain remain inconclusive. See Leung and Cahill (2010).

Despite the development of NGF-targeting and TNFα-targeting candidates for the treatment of pain, there remains a need to provide analgesic relief for various pain conditions through agents that have better efficacy than current standard of care. This disclosure provides combination treatments that target both NGF and TNFα, which can increase efficacy and have the potential to decrease both the amount and frequency of administration for pain-sufferers.

BRIEF SUMMARY OF THE DISCLOSURE

This disclosure provides methods for controlling pain in a subject, comprising administering to a subject in need thereof an effective amount of a nerve growth factor (NGF) antagonist and a tumor necrosis factor-alpha (TNFα) antagonist, or a binding molecule comprising an NGF antagonist domain and a TNFα antagonist domain. In some embodiments, the administration controls pain in the subject more effectively than an equivalent amount of the NGF antagonist or the TNFα antagonist administered alone. In some embodiments, the method comprises co-administering a TNFα antagonist and an NGF antagonist. In some embodiments, the TNFα antagonist and the NGF antagonist are administered sequentially or simultaneously.

In some embodiments, the method is sufficient to prevent, reduce, ameliorate, or eliminate pain in the subject. In some embodiments, the pain is acute pain, short-term pain, persistent or chronic nociceptive pain, or persistent or chronic neuropathic pain. In some embodiments, the method is at least 5%, 10%, 20%, 30%, 40%, 50%, 60%, 70% 80%, 90%, or 100% more effective at controlling pain in the subject than an equivalent amount of the NGF antagonist or the TNFα antagonist administered alone.

In some embodiments, the TNFα antagonist portion of the binding molecule binds a polypeptide comprising the amino acid sequence of SEQ ID NO: 2. In some embodiments, the NGF antagonist binds a polypeptide comprising the amino acid sequence of SEQ ID NO: 1.

In some embodiments, the NGF antagonist portion of the binding molecule is an anti-NGF antibody, or antigen-binding fragment thereof. In some embodiments, the anti-NGF antibody or fragment thereof can inhibit NGF binding to TrkA, p75NTR, or both TrkA and p75NTR. In some embodiments, the anti-NGF antibody preferentially blocks NGF binding to TrkA over NGF binding to p75NTR. In some embodiments, the anti-NGF antibody or fragment thereof binds human NGF with an affinity of about 0.25-0.44 nM. In some embodiments, the anti-NGF antibody or fragment thereof binds to the same epitope as MEDI-578. In some embodiments, the anti-NGF antibody or fragment thereof competitively inhibits binding of MEDI-578 to human NGF.

In some embodiments, the anti-NGF antibody or fragment thereof comprises an antibody VH domain comprising a set of CDRs HCDR1, HCDR2, HCDR3 and an antibody VL domain comprising a set of CDRs LCDR1, LCDR2 and LCDR3, wherein the HCDR1 has the amino acid sequence of SEQ ID NO: 4 or SEQ ID NO: 4 with up to two amino acid substitutions, the HCDR2 has the amino acid sequence of SEQ ID NO: 5 or SEQ ID NO: 5 with up to two amino acid substitutions, the HCDR3 has the amino acid sequence of SEQ ID NO: 6, SEQ ID NO: 6 with up to two amino acid substitutions, SSRIYDFNSALISYYDMDV (SEQ ID NO: 11), or SSRIYDMISSLQPYYDMDV (SEQ ID NO: 12), the LCDR1 has the amino acid sequence of SEQ ID NO: 8 or SEQ ID NO: 8 with up to two amino acid substitutions, the LCDR2 has the amino acid sequence of SEQ ID NO: 9 or SEQ ID NO: 9 with up to two amino acid substitutions, and the LCDR3 has the amino acid sequence of SEQ ID NO: 10 or SEQ ID NO: 10 with up to two amino acid substitutions. In some embodiments, the anti-NGF antibody or fragment thereof comprises a VH having the amino acid sequence of SEQ ID NO: 3. In some embodiments, the anti-NGF antibody or fragment thereof comprises a VL comprising the amino acid sequence of SEQ ID NO: 7. In some embodiments, the anti-NGF antibody or fragment thereof comprises a VH having an amino acid sequence that is at least 80%, 85%, 90%, 95% or 99% identical to the amino acid sequence of SEQ ID NO: 3. In some embodiments, the anti-NGF antibody or fragment thereof comprises a VL having an amino acid sequence that is at least 80%, 85%, 90%, 95% or 99% identical to the amino acid sequence of SEQ ID NO: 7. In some embodiments, the anti-NGF antibody or fragment thereof comprises a VH having the amino acid sequence of SEQ ID NO: 94. In some embodiments, the anti-NGF antibody or fragment thereof comprises a VL comprising the amino acid sequence of SEQ ID NO: 95. In some embodiments, the anti-NGF antibody or fragment thereof comprises a VH having an amino acid sequence that is at least 80%, 85%, 90%, 95% or 99% identical to the amino acid sequence of SEQ ID NO: 94. In some embodiments, the anti-NGF antibody or fragment thereof comprises a VL having an amino acid sequence that is at least 80%, 85%, 90%, 95% or 99% identical to the amino acid sequence of SEQ ID NO: 95.

In some embodiments, the anti-NGF antibody or fragment thereof is a full $H_2L_2$ antibody, an Fab, fragment, an Fab' fragment, an F(ab)$_2$ fragment or a single chain Fv (scFv) fragment. In some embodiments, the anti-NGF antibody or fragment thereof is humanized, chimeric, primatized, or fully human. In some embodiments, the NGF antagonist is an anti-NGF scFv fragment. In some embodiments, the scFv is SS-stabilized. In some embodiments, the anti-NGF scFv fragment comprises, from N-terminus to C-terminus, a VH comprising the amino acid sequence of SEQ ID NO: 3, a 15-amino acid linker sequence (GGGGS)$_3$ (SEQ ID NO:15), and a VL comprising the amino acid sequence of SEQ ID NO: 7. In some embodiments, the anti-NGF scFv fragment comprises, from N-terminus to C-terminus, a VH comprising the amino acid sequence of SEQ ID NO: 94, a 20-amino acid linker sequence (GGGGS)$_4$ (SEQ ID NO: 19), and a VL comprising the amino acid sequence of SEQ ID NO: 95.

In some aspects, the method comprises administering a TNFα antagonist that inhibits binding of TNFα to a TNF receptor (TNFR), thereby blocking TNFα activity. In some embodiments, the TNFα antagonist comprises an anti-TNFα antibody, or antigen-binding fragment thereof. In some embodiments, the anti-TNFα antibody or fragment thereof comprises an antibody VH domain comprising a set of CDRs HCDR1, HCDR2, and HCDR3 and an antibody VL domain comprising a set of CDRs LCDR1, LCDR2 and LCDR3, wherein CDRs the are identical to the HCDR1, HCDR2, HCDR3, LCDR1, LCDR2 and LCDR3 of infliximab or the HCDR1, HCDR2, HCDR3, LCDR1, LCDR2 and LCDR3 of adalimumab.

In some embodiments, the binding molecule comprises a complete anti-TNFα antibody and an anti-NGF scFv fused to the C-terminus of the heavy chain of the anti-TNFα antibody. That binding molecule may comprise a light chain comprising the amino acid sequence of SEQ ID NO: 20 and a heavy chain comprising the amino acid sequence of SEQ ID NO: 22.

In some embodiments, the TNFα antagonist comprises a soluble, TNFα-binding fragment of a TNFR. In some embodiments, the TNFR is TNFR-2 or a soluble fragment thereof. In other embodiments, the TNFR is TNFR-1 or a soluble fragment thereof. In some embodiments, the soluble fragment of TNFR-1 is a 55 kD fragment. In other embodiments, the soluble fragment of TNFR-2 fragment is a 75 kD fragment. In some embodiments, the TNFR fragment is fused to an immunoglobulin Fc domain. In some embodiments, the immunoglobulin Fc domain is a human IgG1 Fc domain. In some embodiments, the TNFα antagonist has an amino acid sequence set forth in SEQ ID NO: 13, or a functional fragment thereof.

In some embodiments, the binding molecule comprises a fusion protein that comprises the NGF antagonist fused to the TNFα antagonist through a linker. In some embodiments, the binding molecule is a homodimer of the fusion protein.

In some embodiments, the NGF antagonist is an anti-NGF scFv domain and the TNFα antagonist is a soluble, TNFα-binding fragment of TNFR-2 fused at its carboxy-terminus to an immunoglobulin Fc domain. In some embodiments, the scFv is fused to the carboxy-terminus of the immunoglobulin Fc domain via a linker.

In some embodiments, the binding molecule comprises a homodimer of a fusion polypeptide comprising, from N-terminus to C-terminus, a TNFα-binding 75 kD fragment of TNFR-2, a human IgG1Fc domain, a 10-amino-acid linker (GGGGS)$_2$, a VH comprising the amino acid sequence of SEQ ID NO 3, a 15-amino acid linker sequence (GGGGS)$_3$ (SEQ ID NO: 15), and a VL comprising the amino acid sequence of SEQ ID NO: 7. In some embodiments, the binding molecule comprises a homodimer of a fusion polypeptide comprising the amino acid sequence of SEQ ID NO: 14. In some embodiments, the binding molecule comprises a homodimer of a fusion polypeptide comprising an amino acid sequence that is at least 80%, 85%, 90%, 95% or 99% identical to the amino acid sequence of SEQ ID NO: 14.

In some embodiments, the binding molecule comprises a homodimer of a fusion polypeptide comprising, from N-terminus to C-terminus, a TNFα-binding 75 kD fragment of TNFR-2, a human IgG1Fc domain, a 10-amino-acid linker (GGGGS)$_2$, a VH comprising the amino acid sequence of SEQ ID NO: 94, a 20-amino acid linker sequence (GGGGS)$_4$ (SEQ ID NO: 19), and a VL comprising the amino acid sequence of SEQ ID NO: 95. In some embodiments, the binding molecule comprises a homodimer of a fusion polypeptide comprising the amino acid sequence of SEQ ID NO: 17. In some embodiments, the binding molecule comprises a homodimer of a fusion polypeptide comprising an amino acid sequence that is at least 80%, 85%, 90%, 95% or 99% identical to the amino acid sequence of SEQ ID NO: 17.

In some embodiments, the binding molecule comprises a homodimer of a fusion polypeptide comprising, from N-terminus to C-terminus, a TNFα-binding 75 kD fragment of TNFR-2, a human IgG1Fc domain, a linker sequence, and an anti-NGF scFv domain.

The disclosure also provides methods for inhibiting p38 phosphorylation in a cell, wherein the method comprises contacting a cell with any of the polypeptides described herein (e.g., any of the binding molecules comprising an NGF antagonist domain and a TNFα antagonist domain described herein). The disclosure also provides methods for inhibiting ERK phosphorylation in a cell, wherein the method comprises contacting a cell with any of the polypeptides described herein (e.g., any of the binding molecules comprising an NGF antagonist domain and a TNFα antagonist domain described herein). In some embodiments, the cell is a neuronal cell. In other embodiments, the cell is a peripheral neuronal cell. In yet other embodiments, the cell is a central neuronal cell. In some embodiments, the cell is in a mammal. In some embodiments, the mammal is a human. In some embodiments, the cell is in a culture of cells.

The disclosure also provides polynucleotide sequences encoding the binding molecules disclosed herein, vectors comprising those polynucleotide sequences, and host cells comprising those polynucleotides or vectors.

The disclosure also provides methods of producing the binding molecules described herein.

The disclosure also provides compositions, pharmaceutical compositions and kits comprising the binding molecules described herein.

BRIEF DESCRIPTION OF THE DRAWINGS/FIGURES

FIGS. 1A and 1B: Schematic representation of a TNFR2-Fc fusion protein (FIG. 1A), and an exemplary multispecific binding molecule, TNFR2-Fc_VH#4, comprising a TNFR2-Fc domain fused to an anti-NGF scFv domain (FIG. 1B).

FIG. 2A shows the results of SEC-HPLC analysis of the levels of aggregate, monomer and protein fragmentation in a batch of purified TNFR2-Fc_VH#4.

FIG. 2B shows SDS-PAGE analysis of purified TNFR2-Fc_VH#4 and the purified TNFR2-Fc protein under reduced and non-reduced conditions. Gel loading order: 1. TNFR2-Fc_VH#4, 2. TNFR2-Fc_VL-VH (TNFR2-Fc fused to an anti-NGF scFv with reverse variable domain gene orientation), 3. TNFR2-Fc irrelevant scFv 1, 4. TNFR2-Fc, 5. TNFR2-Fc irrelevant scFv 2.

FIG. 5A shows binding to NGF, FIG. 5B shows binding to TNFα, and FIG. 5C shows simultaneous binding to TNFα and NGF.

Figure 6:
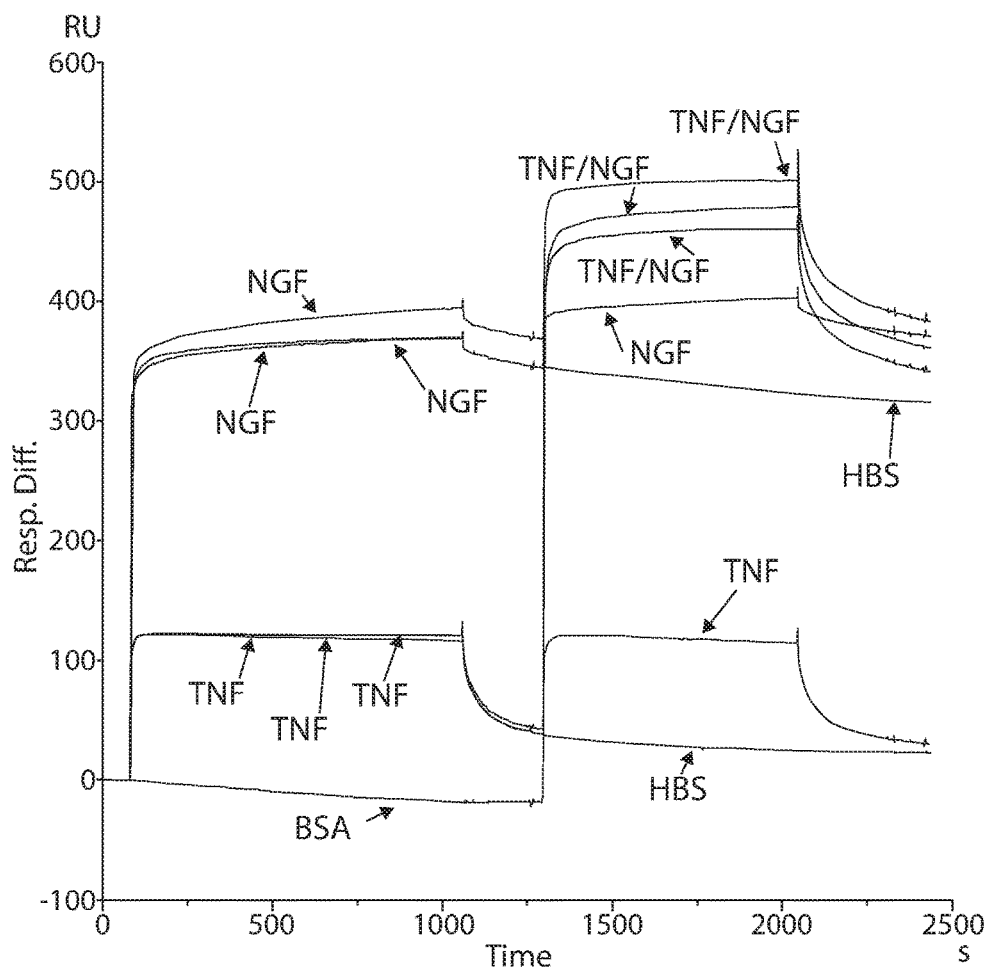

FIG. 6 shows a sensorgram of a surface plasmon resonance binding assay for TNFR2-Fc_VH#4. Concurrent antigen binding of the TNFR2-Fc_VH#4 multispecific antibody was performed using BIAcore 2000. Simultaneous antigen binding was assessed by serially binding TNFα and NGF over TNFR2-Fc_VH#4 bound to the sensor surface. The first part of the sensorgram shows binding of saturating amounts of TNFα to the multispecific antibody, the second part of the sensorgram shows binding when a second antigen was applied, either TNFα again, which showed the surface was saturated, or an equimolar mixture of TNFα and NGF. An increase in resonance units equated to binding of the NGF to the multispecific molecule, and hence simultaneous antigen engagement. The assay was also performed with antigen addition in the reverse order confirming these data.

FIGS. 7A-7E show the inhibition of NGF-mediated proliferation of TF-1 cells. 7A. NGF-mediated proliferation in the absence of added NGF antagonist. 7B. Inhibition of human NGF response by TNFR2-Fc_VH#4. 7C. Inhibition of murine NGF response by TNFR2-Fc_VH#4. Activity of NGF is normally represented as RLU—Relative luminescence Unit, and % of NGF mediated proliferation calculated as % response to NGF ligand alone using the following formula: 100*(well RLU−background RLU)/(Total RLU−background RLU), wherein background RLU=average of media controls, and Total RLU=average of ligand only controls. 7D. Inhibition of human NGF response by TNFR2-Fc_VarB and ndimab VarB. 7E. Inhibition of murine NGF response by TNFR2-Fc_VarB and ndimab VarB.

Figure 7C:
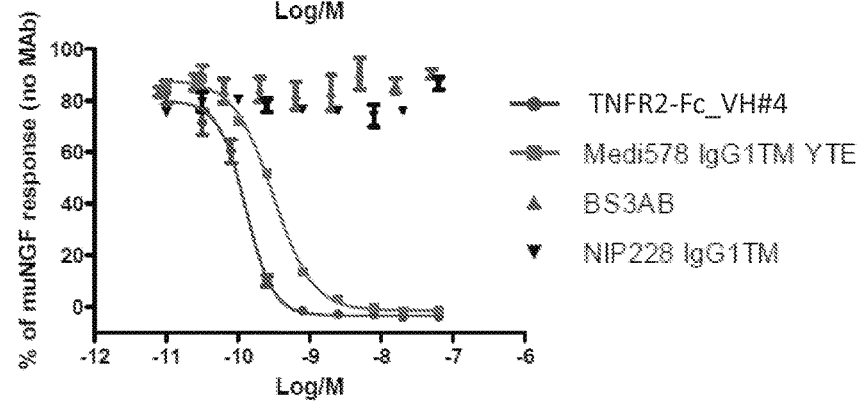
Figure 7D:
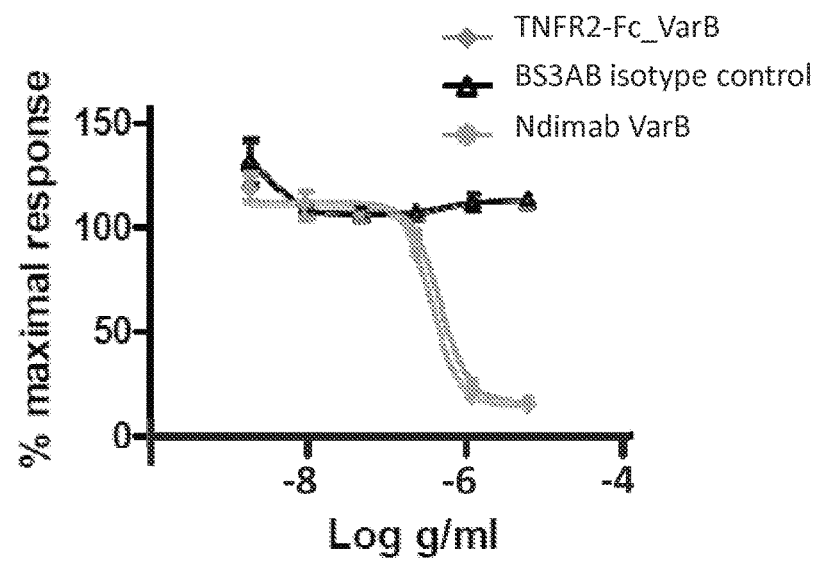
Figure 7E:
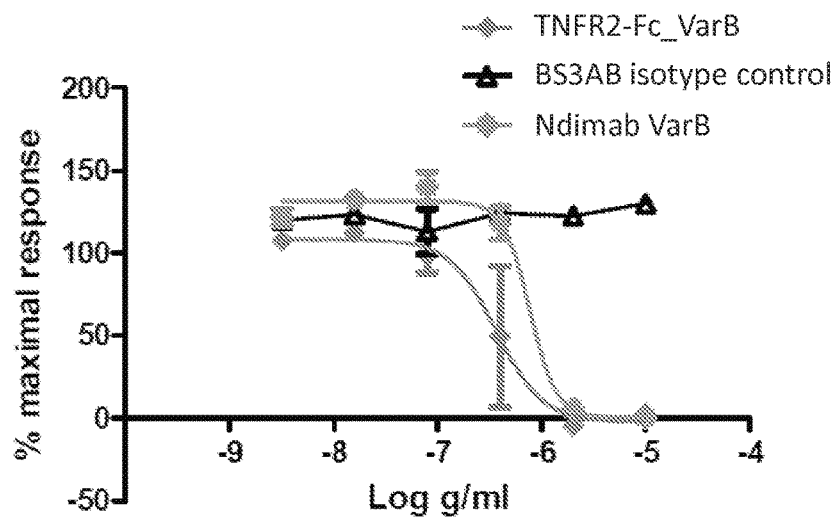
Figure 8A:
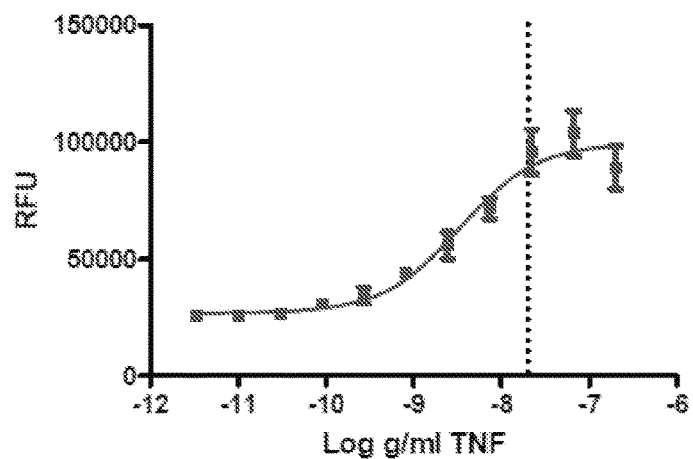
Figure 8B:
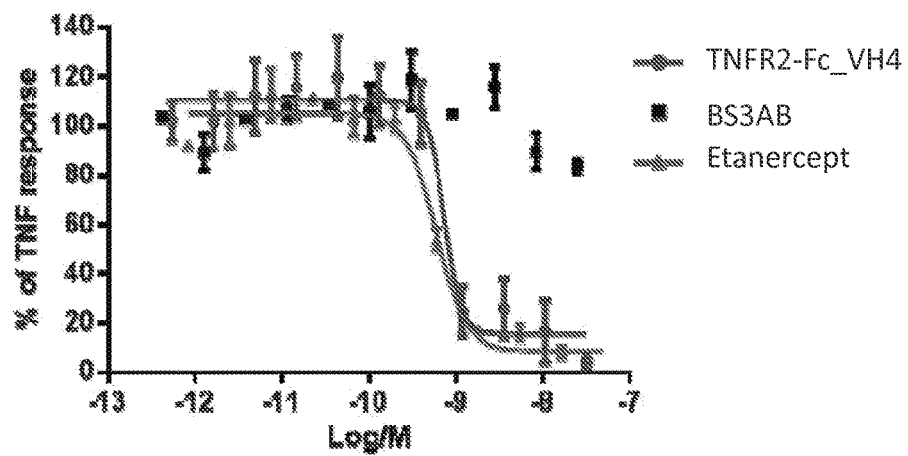
Figure 8C:
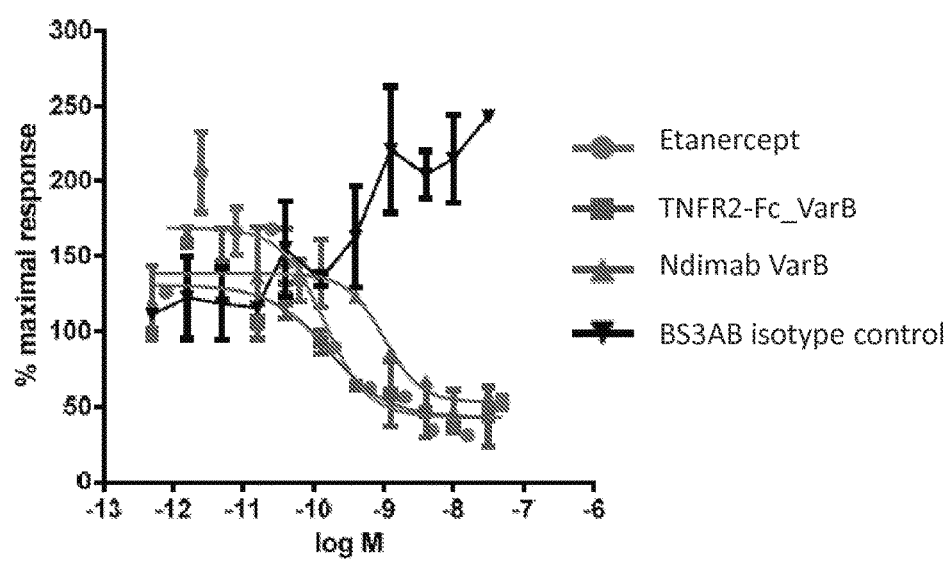

FIGS. 8A-8C show the inhibition of TNFα induced Caspase 3 activity in U937 cells. 8A. TNFα induced Caspase 3 activity in U937 cells in the absence of added TNFα antagonist. 8B. Inhibition of TNFα induced Caspase 3 activity in U937 cells shown as percent of response in the absence of added antagonist. Activity of TNF is normally represented as RFU—Relative Florescence Unit, and % of TNF mediated caspase 3 release was calculated as % response to TNF ligand alone using the using the formula as described above in FIG. 7C: 8C. Similar results shown for a related molecule TNFR2-Fc_varB and ndimab VarB.

Figure 9:
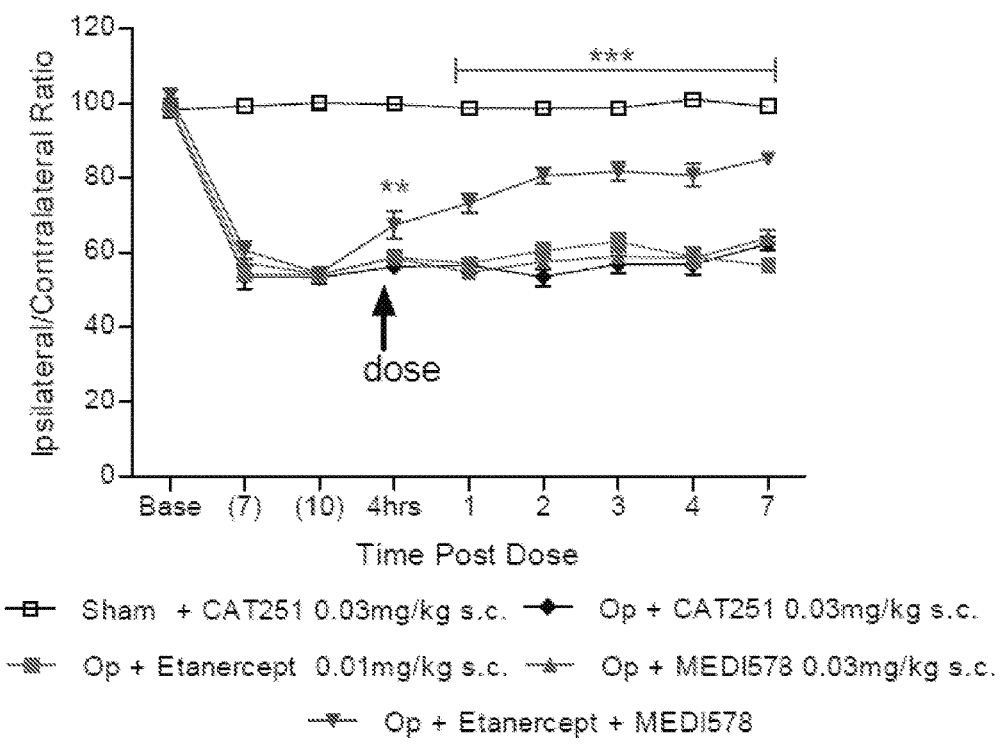

FIG. 9 shows the effect of combination treatment with etanercept and MEDI-578 on a partial sciatic nerve ligation-induced mechanical hyperalgesia. Results are shown as the ipsilateral/contralateral ratio. N=9-10 per group. Data was analyzed using a 2-way ANOVA analysis with time and treatment as dependent factors. Subsequent statistical significance was obtained using Boniferroni's Post Hoc test. ***p<0.001 to Op+CAT-251 control.

Figure 10A:
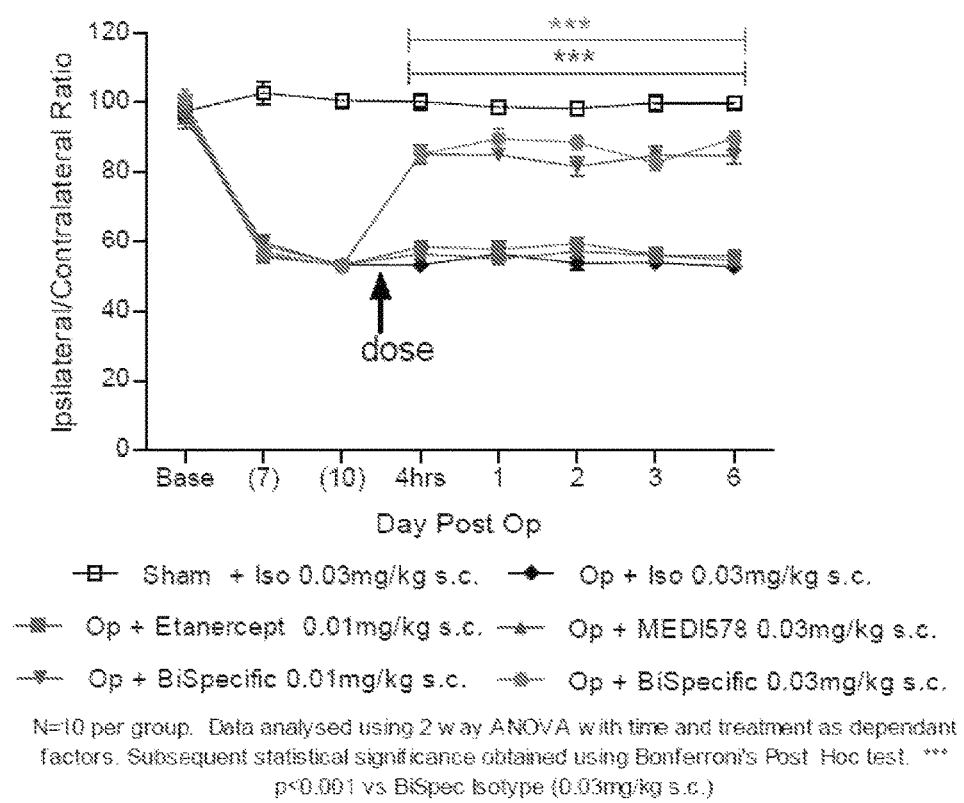
Figure 10B:
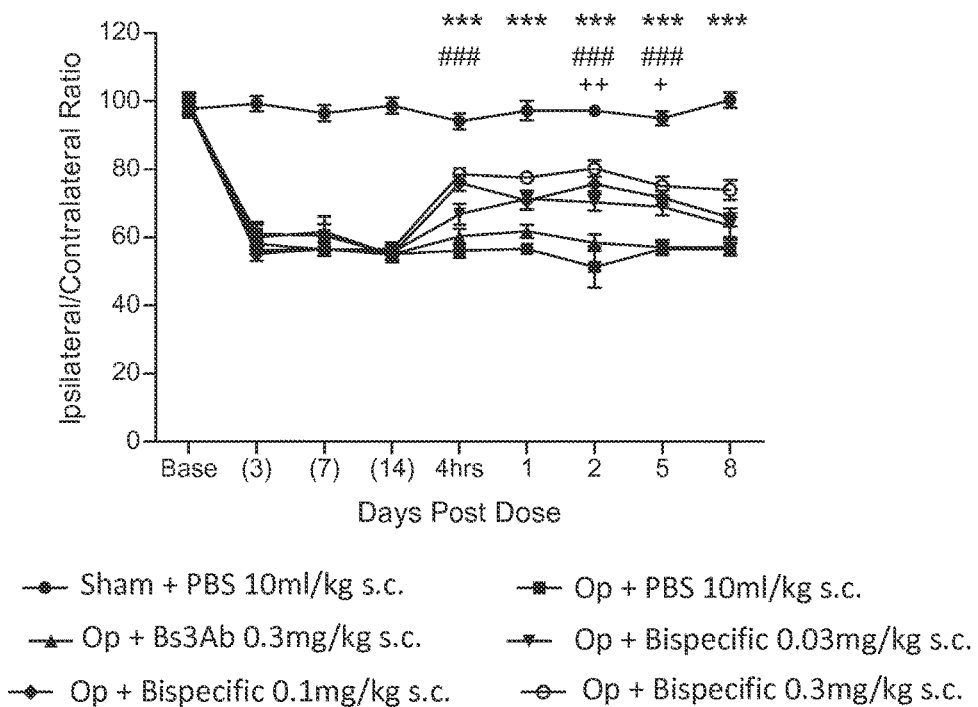

FIG. 10A shows the effect of TNFR2-Fc_VH#4 on partial sciatic nerve ligation-induced mechanical hyperalgesia. Results are shown as the ipsilateral/contralateral ratio. N=10 per group. Data was analyzed using a 2-way ANOVA analysis with time and treatment as dependent factors. Subsequent statistical significance was obtained using Boniferroni's Post Hoc test. ***p<0.001 vs bispecific isotype control. FIG. 10B shows similar results with a related molecule TNFR2-Fc_varB.

Figure 11:
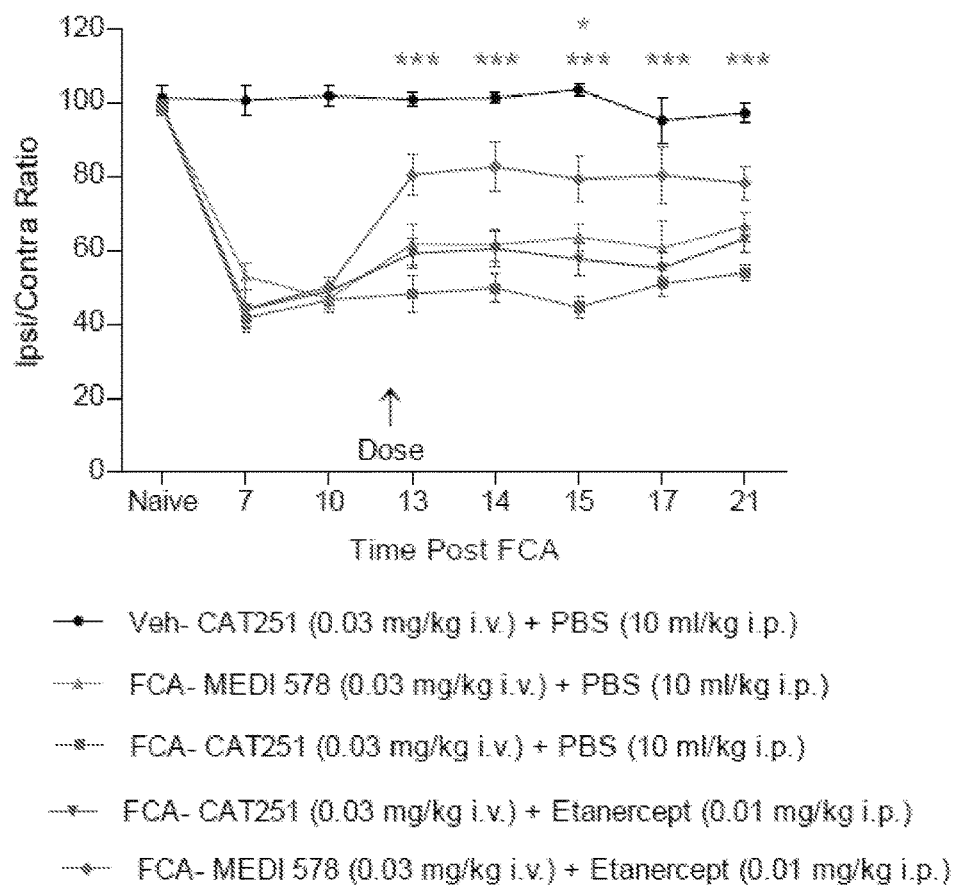

FIG. 11 shows the effect of co-administration of MEDI-578 and etanercept on pain reduction in a joint pain model of mechanical hypersensitivity. N=9-10 per group. Data was analyzed using a 2-way ANOVA analysis. Subsequent statistical significance was obtained using Boniferroni's Post Hoc test. *P>0.05; ***P<0.001 vs. CAT-251.

Figure 12:
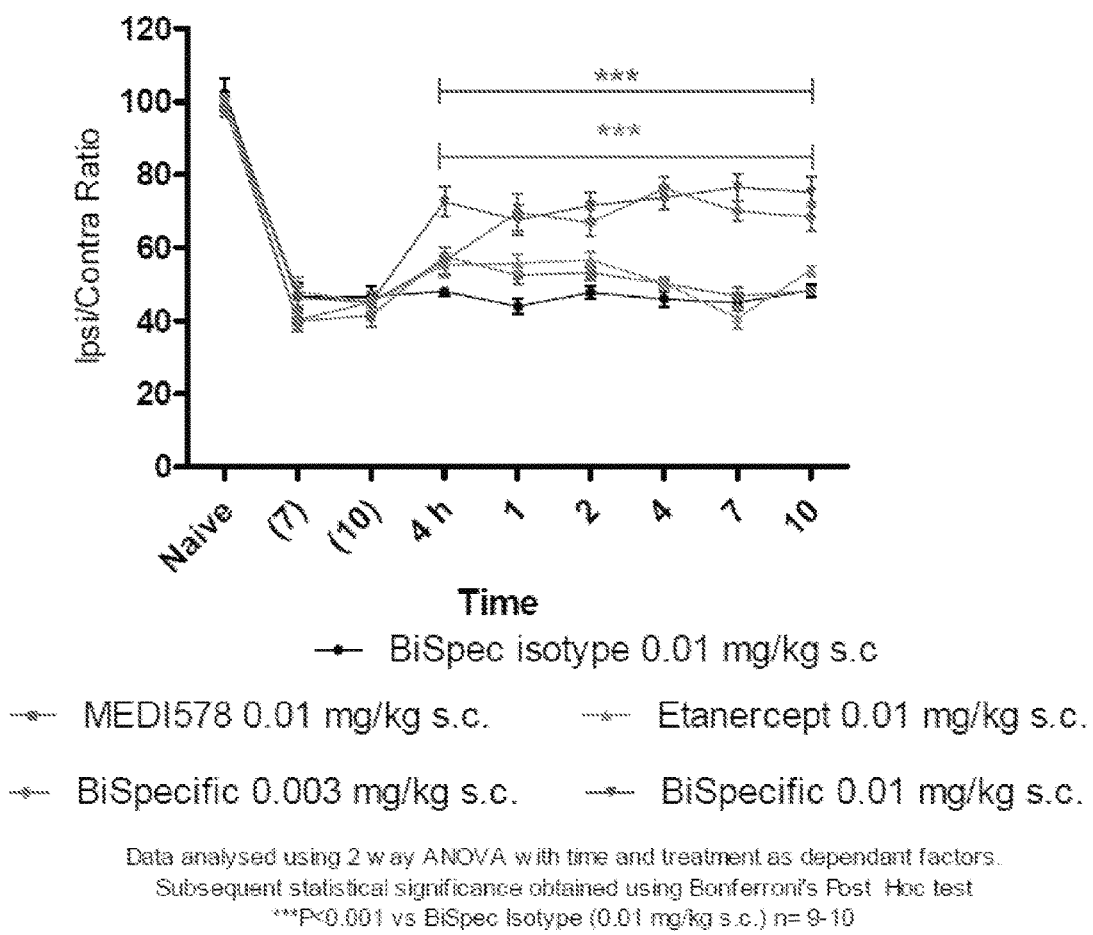

FIG. 12 shows the effect of TNFR2-Fc_VH#4 on pain reduction in a joint pain model of mechanical hypersensitivity. N=9-10 per group. Data was analyzed using a 2-way ANOVA analysis. Subsequent statistical significance was obtained using Boniferroni's Post Hoc test. ***P<0.001 vs. bispecific isotype control.

Figure 13:
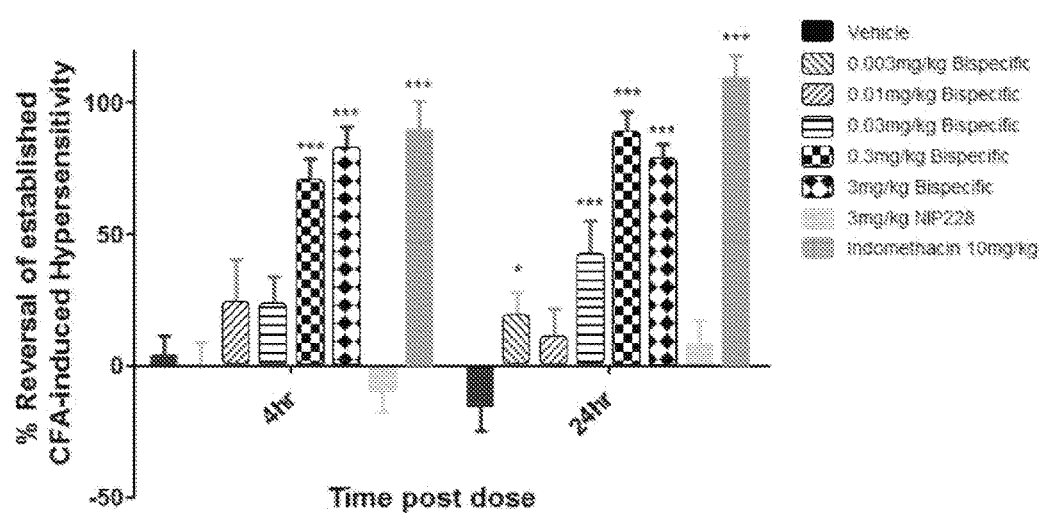

FIG. 13 shows the effects of five different doses of TNFR2-Fc_varB on CFA-induced hyperalgesia in a rat model.

Figure 14:
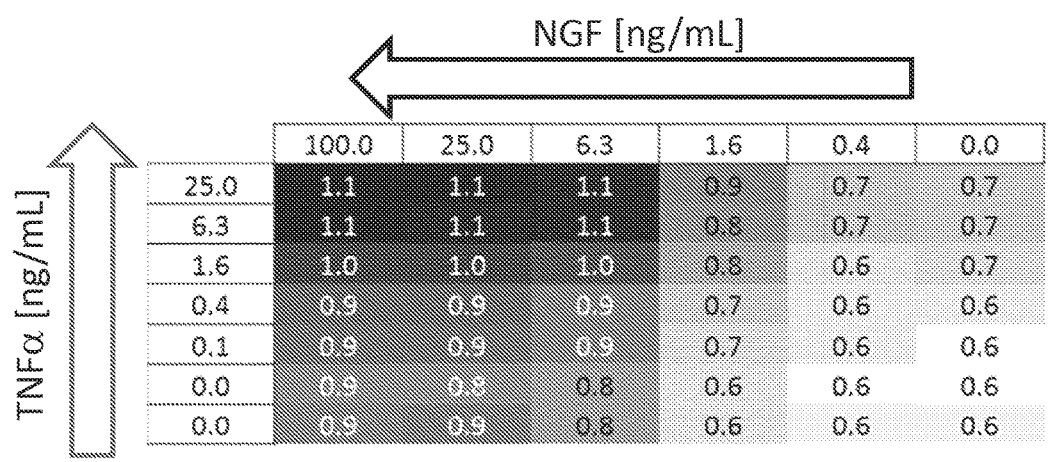

FIG. 14: A heat map showing HTRF ratios from phospho-p38 reactions.

Figure 15:
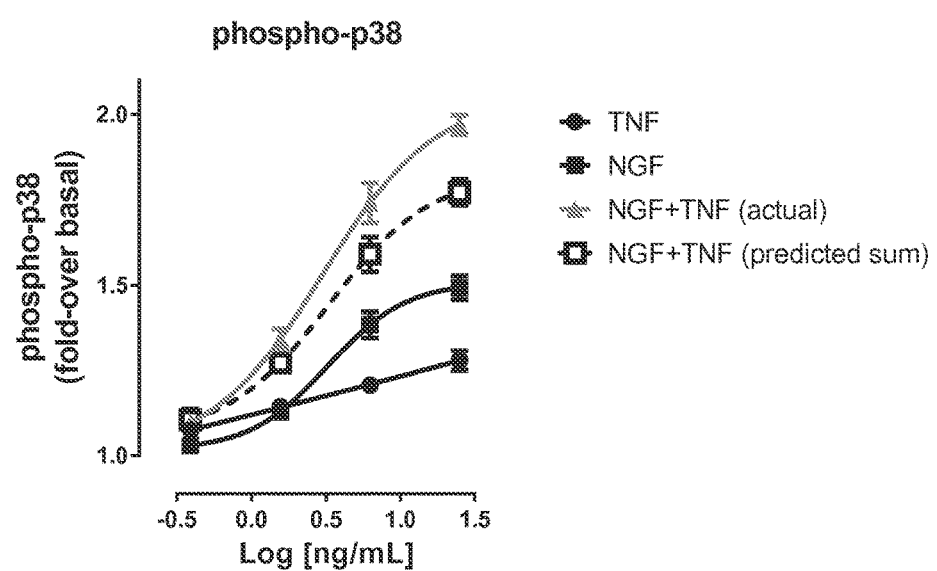

FIG. 15: Dose response curves showing the effect of TNFα, NGF, or a combination of TNFα and NGF on p38 phosphorylation.

Figure 16:
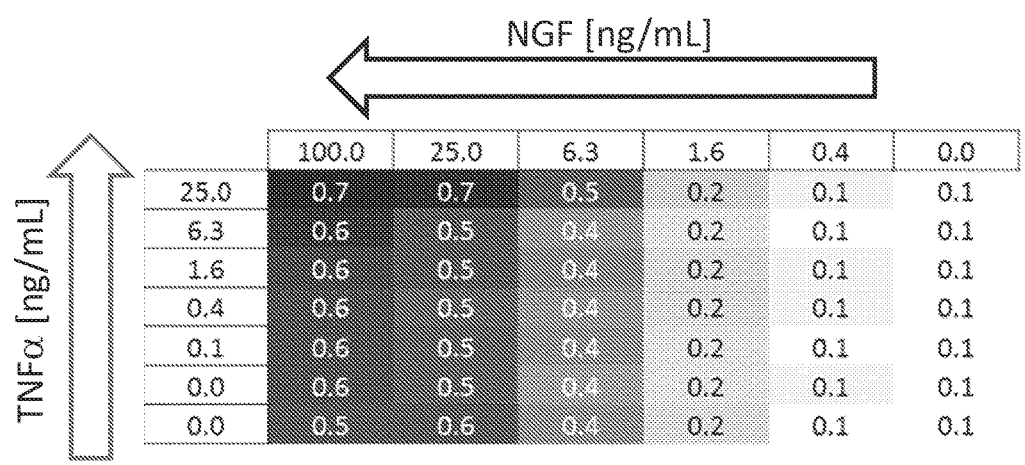

FIG. 16: A heat map showing HTRF ratios from phospho-ERK reactions.

Figure 17:
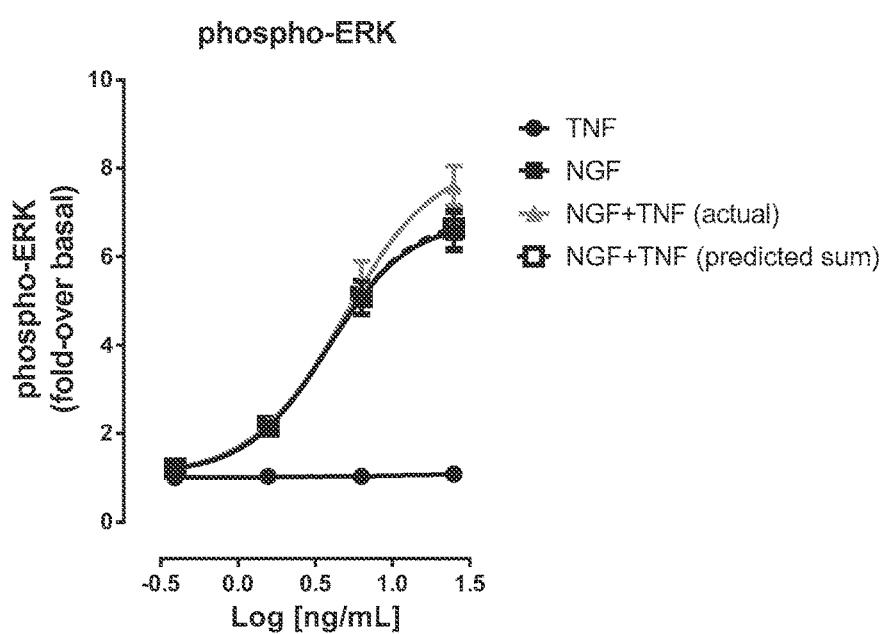

FIG. 17: Dose response curves showing the effect of TNFα, NGF, or a combination of TNFα and NGF on ERK phosphorylation.

DETAILED DESCRIPTION

Definitions

It is to be noted that the term "a" or "an" entity refers to one or more of that entity. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

As used herein, the term "binding molecule" refers in its broadest sense to a molecule that specifically binds an antigenic determinant, e.g., antigen. Non-limiting example of an binding molecule include antibodies or fragment thereof, soluble receptor fusion proteins or fragment thereof, non-immunoglobulin scaffolds or fragments thereof, each retaining antigen specific binding. Exemplary non-immunoglobulin scaffolds include Tn3 (Koide et al., J Mol Biol 2012 Jan. 13; 415(2):393-405), DARPin (Boersma & Pluckthun, Curr Opin Biotechnol. 2011 22(6):849-57), anticalin (Gebauer & Skerra, Methods Enzymol. 2012; 503:157-88). Exemplary soluble receptor fusion proteins and antibodies are provided below. In certain embodiments, the binding molecule could be engineered to comprise combinations of such antibodies or fragments thereof, soluble receptor fusion proteins or fragments thereof, and non-immunoglobulin-based scaffolds or fragment thereof.

The binding molecule, or any portion of the binding molecule that recognizes an antigen is referred to herein as a "binding domain." Unless specifically referring to full-sized binding molecules such as naturally-occurring antibodies, the term "binding molecule" encompasses, without limitation, full-sized antibodies or other non-antibody binding molecules, as well as antigen-binding fragments, variants, analogs, or derivatives of such binding molecules, e.g., naturally occurring antibody or immunoglobulin molecules or engineered binding molecules or fragments that bind antigen in a manner similar to full-sized binding molecule.

In certain embodiments, the disclosure provides certain multi-specific binding molecules, e.g., bispecific, trispecific, tetraspecific, etc. binding molecules, or antigen-binding fragments, variants, or derivatives thereof. As used herein, a multi-specific binding molecule can include one or more antibody binding domains, one or more non-antibody binding domains, or a combination thereof.

The term "nerve growth factor" ("NGF") also referred to in the literature as beta-nerve growth factor, as used herein refers to a secreted protein that functions in the growth and survival of various neurons. Human NGF is presented as Genbank Accession Number NP_002497.2, and is presented here as SEQ ID NO: 1. The term NGF as used herein is not limited to human NGF, and includes all species orthologs of human NGF. The term "NGF" encompasses the pro-form of NGF, pro-NGF, full-length NGF, as well as any form of NGF that results from processing within the cell. The term also encompasses naturally occurring variants of NGF, e.g., splice variants, allelic variants, and isoforms. NGF can bind to two receptors: the p75 neurotrophin receptor (p75(NTR)) and TrkA, a transmembrane tyrosine kinase. NGF is a well-validated target for pain being known to mediate sensitization of nociceptors.

A variety of agents are being tested as antagonists of NGF activity. One such anti-NGF agent is trkA-Fc, which acts as a decoy or scavenger to bind to, and thereby inactivate, endogenous NGF. TrkA-Fc is a fusion protein consisting of the NGF binding region of trkA linked to a constant domain fragment (Fc) of an IgG antibody. TrkA-Fc produces hypoalgesia in naive animals, decreases nociceptor responses, and decreases sprouting of unmyelinated pain-sensing neurons (Bennett, D. L. et al. (1998) *Eur J Neurosci*, 10:1282-91).

NGF-mediated pain is particularly well suited to safe and effective treatment with binding molecules as set forth herein because NGF levels increase in the periphery in response to noxious stimuli and antibodies have low blood-brain barrier permeability. A number of anti-NGF antibodies and antigen-binding fragments thereof which can be used in the therapies and compositions described herein can be found in the literature, see, e.g., PCT Publication Nos. WO02/096458 and WO04/032870.

The term "MEDI-578" refers to an antibody that specifically binds NGF, which is the subject of International Appl. No. PCT/GB2006/000238 and U.S. Patent Appl. Pub. No. 2008/0107658 A1, both of which are incorporated by reference herein in their entirety. The MEDI-578 heavy and light chain sequences are shown in SEQ ID NOs: 3 and 7, respectively.

The term NGF-NG refers to an antibody that specifically binds NGF. The NGF-NG heavy and light chain sequences are shown in SEQ ID NOs: 24 and 26, respectively.

The term "tumor necrosis factor alpha" ("TNFα"), also referred to in the literature as cachectin, APC1 protein; tumor necrosis factor; TNF; or tumor necrosis factor ligand superfamily member 2, as used herein refers to the specific TNFα protein, and not the superfamily of TNF ligands. Human TNFα is presented as Genbank Accession Number NP_000585.2, and is presented as SEQ ID NO: 2. The term TNFα as used herein is not limited to human TNF, and includes all species orthologs of human TNFα. The term "TNFα" encompasses the pro-form of TNFα, pro-TNFα, full-length TNFα, as well as any form of TNFα that results from processing within the cell. The term also encompasses naturally occurring and non-naturally-occurring variants of TNFα, e.g., splice variants, allelic variants, and isoforms. TNFα can bind two receptors, TNFR1 (TNF receptor type 1; CD120a; p55/60) and TNFR2 (TNF receptor type 2; CD120b; p75/80). TNFα functions as a pro-inflammatory cytokine, e.g., functioning in neuroinflammation. For example, TNFα is thought to be functionally involved in the generation of neuropathic pain (Leung, L., and Cahill, C M., *J. Neuroinflammation* 7:27 (2010)).

A large number of TNFα antagonists are known in the art, and many are commercially available as therapeutics. Examples of commercially available TNF-alpha antagonists which can be used in the therapies and compositions provided herein include etanercept (ENBREL®, Amgen/Pfizer), infliximab (e.g., REMICADE®, Centocor), certolizumab pegol (e.g., CIMZIA®, UCB), golimumab (e.g., SIMPONI™, Centocor), and adalimumab (e.g., HUMIRA®/TRUDEXA®, Abbott).

An "isolated" binding molecule, polypeptide, antibody, polynucleotide, vector, host cell, or composition refers to a binding molecule, polypeptide, antibody, polynucleotide, vector, host cell, or composition that is in a non-naturally-occurring form. Isolated binding molecules, polypeptides, antibodies, polynucleotides, vectors, host cells or compositions include those which have been changed, adapted, combined, rearranged, engineered, or otherwise manipulated to a degree that they are no longer in the form in which they are found in nature. In some aspects a binding molecule, antibody, polynucleotide, vector, host cell, or composition that is isolated is "recombinant."

As used herein, the terms "multifunctional polypeptide" and "bifunctional polypeptide" refer to a non-naturally-occurring binding molecule designed to target two or more antigens. A multifunctional polypeptide as described herein is typically a genetically engineered fusion protein designed to bring together two different desired biological functions into a single binding molecule. For example, a multifunctional polypeptide can be a multifunctional binding molecule. An exemplary multifunctional polypeptide described herein is a multifunctional binding molecule comprising an NGF antagonist domain, e.g., a peptide domain which blocks, reduces, or inhibits one or more natural NGF functions, and a TNFα antagonist domain, e.g., a peptide domain which blocks, reduces, or inhibits one or more natural TNFα functions.

One group of multifunctional polypeptides provided herein are multispecific binding molecules, e.g., binding molecules that include one or more antibody binding domains, e.g., a "multispecific antibody," one or more non-antibody binding domains, e.g., a decoy receptor, or a combination thereof. Multispecific binding molecules, e.g., including one or more antibody binding domains, one or more non-antibody binding domains, or a combination thereof, are molecules with binding domains capable of specifically recognizing and binding to at least two different epitopes. The different epitopes can either be within the same molecule (e.g., the same NGF) or on different molecules such that, for example, multispecific binding molecules that can specifically recognize and bind NGF as well as another epitope-containing molecule, e.g., TNFα, such that the multispecific binding molecule specifically recognizes NGF and TNFα.

Techniques for making multispecific binding molecules, e.g., including one or more antibody binding domains, one or more non-antibody binding domains, or a combination thereof, are available in the art (Dimasi, N., et al., 2009, *J Mol Biol.* 393:672-92; Milstein et al., 1983, *Nature* 305: 537-539; Brennan et al., 1985, *Science* 229:81; Suresh et al., 1986, *Methods in Enzymol.* 121:120; Traunecker et al., 1991, *EMBO J.* 10:3655-3659; Shalaby et al., 1992, *J. Exp. Med.* 175:217-225; Kostelny et al., 1992, *J. Immunol.* 148: 1547-1553; Gruber et al., 1994, *J. Immunol.* 152:5368; and U.S. Pat. No. 5,731,168). Antibodies with more than two valencies are also contemplated. For example, trispecific antibodies can be prepared (Tutt et al., *J. Immunol.* 147:60 (1991)).

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')$_2$, and Fv fragments), single chain Fv (scFv) mutants, multispecific antibodies such as bispecific, trispecific, tetraspecific, etc antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations.

In some embodiments, a "blocking" binding molecule, e.g., a blocking antibody or an "antagonist" binding molecule, such as for example, an antagonist antibody or fusion protein is one that inhibits or reduces biological activity of the antigen to which it binds, such as NGF or TNFα. In certain aspects blocking antibodies or antagonist binding molecules substantially or completely inhibit the biological activity of the antigen. For example, the biological activity can be reduced by 0.01%, 0.1%, 0.5%, 1%, 5%, 10%, 20%, 30%, 50%, 70%, 80%, 90%, 95%, or even 100%. "Antagonists" and "antagonist domains" as used herein include polypeptides or other molecules that bind to their target (e.g., TNFα or NGF), thereby blocking or inhibiting the target from interacting with a receptor. NGF and/or TNFα antagonists thus include molecules that block or inhibit NGF interaction with trkA or p75 neurotrophin, or TNFα interaction with TNFR-1 or TNFR-2. NGF and/or TNFα antagonists also include molecules that reduce p38 phosphorylation and/or ERK phosphorylation. Exemplary antagonists include, but are not limited to antibodies or antigen-binding fragments thereof, and target-specific, soluble, non-signaling receptor peptides ("decoy receptors," or ligand-binding fragments thereof).

The term "antibody fragment" refers to a portion of an intact antibody and refers to the antigenic determining variable regions of an intact antibody. Examples of antibody fragments include, but are not limited to Fab, Fab', F(ab')$_2$, and Fv fragments, linear antibodies, single chain antibodies, and multispecific antibodies formed from antibody fragments. Antigen-binding fragments of non-antibody binding molecules, described elsewhere herein, are also provided by this disclosure.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')$_2$, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., 1986, Nature, 321:522-525; Riechmann et al., 1988, Nature, 332:323-327; Verhoeyen et al., 1988, Science, 239:1534-1536). In some instances, the Fv framework region (FR or FW) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539 or 5,639,641.

A "variable region" of an antibody refers to the variable region of the antibody light chain or the variable region of the antibody heavy chain, either alone or in combination. The variable regions of the heavy and light chain each consist of four framework regions (FR or FW) connected by three complementarity-determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) *J. Molec. Biol.* 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., Sequences of Immunological Interest, 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g., residues 82a, 82b, and 82c, etc according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk *J. Mol. Biol.* 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software. A comparison is provide in Table 1 below.

TABLE 1

Comparison of Antibody Numbering Systems

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | | (Kabat Numbering) |
| H1 | H31-H35 | H26-H35 | H26-H32 |
| | | | (Chothia Numbering) |
| H2 | H50-H65 | H50-H58 | H52-H56 |
| H3 | H95-H102 | H95-H102 | H95-H102 |

The term "human antibody" means a native human antibody or an antibody having an amino acid sequence corresponding to a native human antibody, made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species. Multispecific binding molecules, e.g., including one or more antibody binding domains, one or more non-antibody binding domains, or a combination thereof, e.g., TNFα antagonists and/or NGF antagonists provided herein can comprise antibody constant regions (e.g., Fc regions) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. Modified constant regions provided herein can comprise alterations or modifications to one or more of the three heavy chain constant domains (CH1, CH2 or CH3) and/or to the light chain constant domain (CL). In some aspects, one or more constant domains can be partially or entirely deleted. In some aspects, the entire CH2 domain can be deleted (ΔCH2 constructs). See, e.g., Oganesyan V, et al., 2008 *Acta Crystallogr D Biol Crystallogr.* 64:700-4; Oganesyan V, et al., *Mol Immunol.* 46:1750-5; Dall'Acqua, W. F., et al., 2006. *J. Biol. Chem.* 281:23514-23524; and Dall'Acqua, et al., 2002. *J. Immunol.* 169:5171-5180.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. An epitope as described herein need not be defined down to the specific amino acids that form the epitope. In some aspects an epitope can be identified by examination of binding to peptide subunits of a polypeptide antigen, or by examining binding competition to the antigen by a group of antigen-specific antibodies.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, sports animals, and zoo animals including, e.g., humans, non-human primates, dogs, cats, guinea pigs, rabbits, rats, mice, horses, cattle, bears, and so on.

The terms "composition and "pharmaceutical composition" refer to a preparation which is in such form as to permit the biological activity of the active ingredient to be effective, and which contains no additional components which are unacceptably toxic to a subject to which the composition would be administered. Such compositions can be sterile.

As used herein, the terms "effective amount" and "therapeutically effective amount" refer to an amount of one or more therapeutic compositions effective to control pain in a subject. The term "control pain" and grammatical equivalents is used herein to describe any beneficial or desirable effect in a subject in need of pain control. For example, an effective amount of one or more therapeutic compositions described herein can, e.g., prevent pain, maintain a tolerable level of pain, ameliorate pain, reduce pain, minimize pain, or eliminate pain in the subject.

The term "administering" as used herein refers to administering to a subject one or more therapeutic compositions described herein, e.g., a bifunctional polypeptide comprising an NGF antagonist domain and a TNFα antagonist domain, a therapeutic composition comprising a combination of an NGF antagonist and a TNFα antagonist, or separate therapeutic compositions, one comprising an NGF antagonist and one comprising a TNFα antagonist. The term "co-administering" refers to administering to a subject two or more therapeutic compositions, e.g., one comprising an NGF antagonist and one comprising a TNFα antagonist. As used herein, co-administering includes, but does not require that the two or more therapeutic compositions be administered to the subject simultaneously. The two or more therapeutic compositions can be administered to the subject sequentially, e.g., thirty minutes apart, one hour apart, two hours apart, three hours apart, four hours apart, or five or more hours apart. The sequence and timing of a co-administration as described herein can be fixed, or can be varied based on the judgment of a healthcare professional.

The terms "polynucleotide" and "nucleic acid" refer to a polymeric compound comprised of covalently linked nucleotide residues. Polynucleotides can be DNA, cDNA, RNA, single stranded, or double stranded, vectors, plasmids, phage, or viruses.

The term "vector" means a construct, which is capable of delivering, and expressing, one or more gene(s) or sequence (s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and non-amino acids can interrupt it. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In certain aspects, conservative substitutions in the sequences of polypeptides and antibodies provided herein do not abrogate the binding or other functional activity of the polypeptide containing the amino acid sequence. Methods of identifying nucleotide and amino acid conservative substitutions which do not affect function are well-known in the art (see, e.g., Brummell et al., *Biochem.* 32: 1180-1 187 (1993); Kobayashi et al. *Protein Eng.* 12:879-884 (1999); and Burks et al. *Proc. Natl. Acad. Sci. USA* 94:412-417 (1997)).

Binding Molecule Comprising an NGF Antagonist Domain and a TNFα Antagonist Domain This disclosure provides a bifunctional polypeptide comprising an NGF antagonist domain and a TNFα antagonist domain. In certain aspects, administration of an effective amount of a bifunctional polypeptide provided herein can control pain, in a subject in need thereof, more effectively than an equivalent amount of the NGF antagonist or the TNFα antagonist administered alone. Bifunctional polypeptides provided herein can include the NGF antagonist domain and the TNFα antagonist domain in any order, structure, or conformation. Any suitable NGF antagonists or TNFα antagonists can be part of a bifunctional polypeptide provided herein. Exemplary NGF antagonists and TNFα antagonists are described elsewhere in this disclosure.

In certain aspects, the NGF antagonist is a non-antibody molecule, or a binding domain thereof, capable of inhibiting NGF activity, e.g., a soluble, NGF-binding fragment of TrkA. In certain aspects, the NGF antagonist is an anti-NGF antibody, or antigen-binding fragment thereof. Suitable anti-NGF antagonists, e.g., antagonist antibodies can inhibit NGF binding to TrkA, p75NRT, or both TrkA and p75NRT. In certain aspects, an anti-NGF antagonist, e.g., an antagonist antibody or fragment thereof for use in a bifunctional molecule provided herein, e.g., a multispecific binding molecule, can preferentially block NGF binding to TrkA over NGF binding to p75NRT.

Exemplary antibodies or fragments thereof for use in bifunctional polypeptides, e.g., multispecific binding molecules disclosed herein are available in U.S. Appl. Publication No. 2008/0107658, which is incorporated herein by reference in its entirety. In certain aspects, the anti-NGF antibody or fragment thereof binds to the same epitope as, can competitively inhibit, or can bind to NGF with a greater affinity than the anti-NGF antibody MEDI-578. In certain embodiments, the anti-NGF antibody or fragment thereof binds human NGF and/or rat NGF with an affinity of or less than 1, 0.8, 0.7, 0.6, 0.5, 0.4, 0.3 or 0.2 nM. For example, the anti-NGF antibody or fragment thereof may bind human NGF with an affinity of about 0.2-0.8, 0.2-0.7, 0.2-06, 0.2-0.5, and/or 0.25-0.44 nM and rat NGF with an affinity of about 0.2-0.9, 0.2-0.8, and/or 0.25-0.70 nM.

In certain aspects, the anti-NGF antibody or fragment thereof is MEDI-578. MEDI-578 is disclosed in U.S. Appl. Publication No. 2008/0107658 as clone 1252A5. In other aspects, the anti-NGF antibody or fragment thereof is tanezumab (RN-624), a humanized anti-NGF mAb (Pfizer; described in Kivitz et al., (2013) PAIN, 154, 9, 1603-161), fulranumab, a fully human anti-NGF mAb (Amgen; described in Sanga et al., PAIN, Volume 154, Issue 10, October 2013, Pages 1910-1919); REGN475/SAR164877, a fully human anti-NGF mAb (Regeneron/Sanafi-Aventis); ABT-110 (PG110), a humanized anti-NGF mAb (Abbott Laboratories). An anti-NGF antibody or fragment thereof included in a bifunctional polypeptide, e.g., multispecific binding molecule provided herein, can be, e.g., humanized, chimeric, primatized, or fully human.

In certain aspects, the anti-NGF antibody or fragment thereof comprises an antibody VH domain comprising the HCDR1, HCDR2, and HCDR3 domains of MEDI-578, variants of the MEDI-578 heavy chain CDRs with up to one, two, three, four, five, or more amino acid substitutions, e.g., conservative amino acid substitutions. For example, the anti-NGF antibody or fragment thereof can comprise an HCDR1 with the exact amino acid sequence of SEQ ID NO: 4 or with the amino acid sequence of SEQ ID NO: 4 with one or more, e.g., one, two, three, four, five, or more amino acid substitutions. Similarly, the anti-NGF antibody or fragment thereof can comprise an HCDR2 with the exact amino acid sequence of SEQ ID NO: 5 or with the amino acid sequence of SEQ ID NO: 5 with one or more, e.g., one, two, three, four, five, or more amino acid substitutions. Likewise, the anti-NGF antibody or fragment thereof can comprise an HCDR3 with the exact amino acid sequence of SEQ ID NO: 6 or with the amino acid sequence of SEQ ID NO: 6 with one or more, e.g., one, two, three, four, five, or more amino acid substitutions. In certain aspects, the HCDR3 can comprise the amino acid sequence SSRIYDFNSALISYYDMDV (SEQ ID NO: 11), or SSRIYDMISSLQPYYDMDV (SEQ ID NO: 12).

In certain aspects, the anti-NGF antibody or fragment thereof comprises an antibody VL domain comprising the LCDR1, LCDR2, and LCDR3 domains of MEDI-578, variants of the MEDI-578 light chain CDRs with up to one, two, three, four, five, or more amino acid substitutions, e.g., conservative amino acid substitutions. In certain aspects, the anti-NGF antibody or fragment thereof can comprise an LCDR1 with the exact amino acid sequence of SEQ ID NO: 8 or with the amino acid sequence of SEQ ID NO: 8 with one or more, e.g., one, two, three, four, five, or more amino acid substitutions. Similarly, the anti-NGF antibody or fragment thereof can comprise an LCDR2 with the exact amino acid sequence of SEQ ID NO: 9 or with the amino acid sequence of SEQ ID NO: 9 with one or more, e.g., one, two, three, four, five, or more amino acid substitutions. Likewise, the anti-NGF antibody or fragment thereof can comprise an LCDR3 with the exact amino acid sequence of SEQ ID NO: 10 or with the amino acid sequence of SEQ ID NO: 10 with one or more, e.g., one, two, three, four, five, or more amino acid substitutions.

In certain aspects, the anti-NGF antibody or fragment thereof comprises an antibody VH domain comprising a VH amino acid sequence at least 80%, 85%, 90%, 95%, 96%, 97%, 98%, or 99% identical to the amino acid sequence of SEQ ID NO: 3. In some aspects the anti-NGF antibody or fragment thereof comprises an antibody VH domain comprising the VH amino acid sequence of SEQ ID NO: 3.

In certain aspects, the anti-NGF antibody or fragment thereof comprises an antibody VL domain comprising a VL amino acid sequence at least 80%, 85%, 90%, 95%, 96%, 97%, 98%, or 99% identical to the amino acid sequence of SEQ ID NO: 7. In some aspects the anti-NGF antibody or fragment thereof comprises an antibody VL domain comprising the VL amino acid sequence of SEQ ID NO: 7.

In certain aspects, the anti-NGF antibody or fragment thereof comprises an antibody VH domain comprising a VH amino acid sequence at least 80%, 85%, 90%, 95%, 96%, 97%, 98%, or 99% identical to the amino acid sequence of SEQ ID NO: 94. In some aspects the anti-NGF antibody or fragment thereof comprises an antibody VH domain comprising the VH amino acid sequence of SEQ ID NO: 94.

In certain aspects, the anti-NGF antibody or fragment thereof comprises an antibody VL domain comprising a VL amino acid sequence at least 80%, 85%, 90%, 95%, 96%, 97%, 98%, or 99% identical to the amino acid sequence of SEQ ID NO: 95. In some aspects the anti-NGF antibody or fragment thereof comprises an antibody VL domain comprising the VL amino acid sequence of SEQ ID NO: 95.

In certain aspects, the anti-NGF antibody or fragment thereof comprises an antibody VH domain comprising the HCDR1, HCDR2, and HCDR3 domains of any one of SEQ ID NOs: 30, 32, 34, 36, 38, 40, 42, 44, 46, 48, 50, 52, 54, 56, 58, 60, 62, 64, 66, 68, 70, 72, 74, 76, 78, 80, 82, 84, 86 and 96, or variants thereof with up to one, two, three, four, five, or more amino acid substitutions, e.g., conservative amino acid substitutions.

In certain aspects, the anti-NGF antibody or fragment thereof comprises an antibody VL domain comprising the LCDR1, LCDR2, and LCDR3 domains of any one of SEQ ID NOs: 31, 33, 35, 37, 39, 41, 43, 45, 47, 49, 51, 53, 55, 57, 59, 61, 63, 65, 67, 69, 71, 73, 75, 77, 79, 81, 83, 85, 87 and 97, or variants thereof with up to one, two, three, four, five, or more amino acid substitutions, e.g., conservative amino acid substitutions.

In certain aspects, the anti-NGF antibody or fragment thereof comprises an antibody VH domain comprising a VH amino acid sequence at least 80%, 85%, 90%, 95%, 96%, 97%, 98%, or 99% identical to the amino acid sequence of any one of SEQ ID NOs: 30, 32, 34, 36, 38, 40, 42, 44, 46, 48, 50, 52, 54, 56, 58, 60, 62, 64, 66, 68, 70, 72, 74, 76, 78, 80, 82, 84, 86 and 96. In some aspects the anti-NGF antibody or fragment thereof comprises an antibody VH domain comprising the VH amino acid sequence of any one of SEQ ID NOs: 30, 32, 34, 36, 38, 40, 42, 44, 46, 48, 50, 52, 54, 56, 58, 60, 62, 64, 66, 68, 70, 72, 74, 76, 78, 80, 82, 84, 86 and 96.

In certain aspects, the anti-NGF antibody or fragment thereof comprises an antibody VL domain comprising a VL amino acid sequence at least 80%, 85%, 90%, 95%, 96%, 97%, 98%, or 99% identical to the amino acid sequence of any one of SEQ ID NOs: 31, 33, 35, 37, 39, 41, 43, 45, 47, 49, 51, 53, 55, 57, 59, 61, 63, 65, 67, 69, 71, 73, 75, 77, 79, 81, 83, 85, 87 and 97. In some aspects the anti-NGF antibody or fragment thereof comprises an antibody VL domain comprising the VL amino acid sequence of any one of SEQ ID NOs: 31, 33, 35, 37, 39, 41, 43, 45, 47, 49, 51, 53, 55, 57, 59, 61, 63, 65, 67, 69, 71, 73, 75, 77, 79, 81, 83, 85, 87 and 97.

In certain aspects, the anti-NGF antibody or fragment thereof comprises an antibody VH domain comprising the HCDR1, HCDR2, and HCDR3 domains of NGF-NG, variants of the NGF-NG heavy chain CDRs with up to one, two, three, four, five, or more amino acid substitutions, e.g., conservative amino acid substitutions. For example, the anti-NGF antibody or fragment thereof can comprise an HCDR1 with the exact amino acid sequence of SEQ ID NO: 88 or with the amino acid sequence of SEQ ID NO: 88 with one or more, e.g., one, two, three, four, five, or more amino acid substitutions. Similarly, the anti-NGF antibody or fragment thereof can comprise an HCDR2 with the exact amino acid sequence of SEQ ID NO: 89 or with the amino acid sequence of SEQ ID NO: 89 with one or more, e.g., one, two, three, four, five, or more amino acid substitutions. Likewise, the anti-NGF antibody or fragment thereof can comprise an HCDR3 with the exact amino acid sequence of SEQ ID NO: 90 or with the amino acid sequence of SEQ ID NO: 90 with one or more, e.g., one, two, three, four, five, or more amino acid substitutions.

In certain aspects, the anti-NGF antibody or fragment thereof comprises an antibody VL domain comprising the LCDR1, LCDR2, and LCDR3 domains of NGF-NG, variants of the NGF-NG light chain CDRs with up to one, two, three, four, five, or more amino acid substitutions, e.g., conservative amino acid substitutions. In certain aspects, the anti-NGF antibody or fragment thereof can comprise an LCDR1 with the exact amino acid sequence of SEQ ID NO: 91 or with the amino acid sequence of SEQ ID NO: 91 with one or more, e.g., one, two, three, four, five, or more amino acid substitutions. Similarly, the anti-NGF antibody or fragment thereof can comprise an LCDR2 with the exact amino acid sequence of SEQ ID NO: 92 or with the amino acid sequence of SEQ ID NO: 92 with one or more, e.g., one, two, three, four, five, or more amino acid substitutions. Likewise, the anti-NGF antibody or fragment thereof can comprise an LCDR3 with the exact amino acid sequence of SEQ ID NO: 93 or with the amino acid sequence of SEQ ID NO: 93 with one or more, e.g., one, two, three, four, five, or more amino acid substitutions.

In certain aspects, the anti-NGF antibody or fragment thereof comprises an antibody VH domain comprising a VH amino acid sequence at least 80%, 85%, 90%, 95%, 96%, 97%, 98%, or 99% identical to the amino acid sequence of SEQ ID NO:24. In some aspects the anti-NGF antibody or fragment thereof comprises an antibody VH domain comprising the VH amino acid sequence of SEQ ID NO: 24.

In certain aspects, the anti-NGF antibody or fragment thereof comprises an antibody VL domain comprising a VL amino acid sequence at least 80%, 85%, 90%, 95%, 96%, 97%, 98%, or 99% identical to the amino acid sequence of SEQ ID NO: 26. In some aspects the anti-NGF antibody or fragment thereof comprises an antibody VL domain comprising the VL amino acid sequence of SEQ ID NO: 26.

A multifunctional polypeptide, e.g., multispecific binding molecule as provided by this disclosure can comprise a complete anti-NGF antibody, i.e., an antibody comprising two complete heavy chains and two complete light chains in an $H_2L_2$ format. Where the anti-NGF antibody is a complete antibody, one or more TNFα antagonist domains can be fused to the N-terminus or C-terminus of one or more heavy chains of the anti-NGF antibody or to the N-terminus or C-terminus of one or more light chains of the anti-NGF antibody. Alternatively, a multifunctional polypeptide, e.g., multispecific binding molecule as provided by this disclosure can comprise an antigen-binding fragment of an anti-NGF antibody. In certain aspects an anti-NGF antibody fragment can comprise any portion of the antibody's constant domains or can comprise only the variable domains. Exemplary anti-NGF antibody fragments for inclusion in a bifunctional polypeptide, e.g., multispecific binding molecule, include, but are not limited to Fab fragments, Fab' fragments, F(ab)$_2$ fragments or single chain Fv (scFv) fragments.

In certain exemplary compositions provided herein, the anti-NGF antibody is a scFv fragment, e.g. an scFv fragment of MEDI-578, or an NGF-binding variant thereof. In certain exemplary compositions provided herein, the anti-NGF antibody is a scFv fragment, e.g. an scFv fragment of NGF-NG, or an NGF-binding variant thereof. An anti-NGF scFv polypeptide can comprise the VH and VL domains in any order, either N—VH-VL-C, or N-VL-VH-C. ScFv molecules are typically engineered such that the VH and VL domains are connected via a flexible linker. Exemplary scFv structures, including various linkers can be found in Dimasi, N., et al., *J Mol Biol.* 393:672-92 (2009), and in PCT Publication No. WO 2013/070565, both of which are incorporated herein by reference in their entireties. As is understood by persons of ordinary skill in the art, scFv antibody fragments can have reduced stability relative to the variable domains existing in a standard Fab conformation. In some aspects the scFv can be structurally stabilized by introducing stabilizing mutations or by introducing interchain disulfide bond(s) (e.g., SS-stabilized). However, stabilizing mutations and/or an introduced interchain disulfide bond is not required and, in certain aspects, is not present. A number of art-recognized methods are available to stabilize scFv polypeptides.

Linkers can be used to join domains/regions of bifunctional polypeptides provided herein. Linkers can be used to connect the NGF antagonist domain and the TNFα antagonist domain of a bifunctional molecule, and can also be used to interconnect the variable heavy and light chains of an scFv. An exemplary, non-limiting example of a linker is a polypeptide chain comprising at least 4 residues. Portions of such linkers can be flexible, hydrophilic and have little or no secondary structure of their own (linker portions or flexible linker portions). Linkers of at least 4 amino acids can be used to join domains and/or regions that are positioned near to one another after a bifunctional polypeptide molecule has assembled. Longer linkers can also be used. Thus, linkers can be about 1, 2, 3, 4, 5, 6, 7, 8, 9, 10, 11, 12, 13, 14, 15, 16, 17, 18, 19, 20, 25, 30, 35, 40, 45, 50, residues. Linkers can also be, for example, from about 100-175 residues. When multiple linkers are used to interconnect portions of a bifunctional polypeptide molecule, the linkers can be the same or different (e.g., the same or different length and/or amino acid sequence).

The linker(s) in a bifunctional polypeptide molecule facilitate formation of the desired structure. Linkers can comprise (Gly-Ser)$_n$ residues (where n is an integer of at least one, two and up to, e.g., 3, 4, 5, 6, 10, 20, 50, 100, or more), with some Glu or Lys residues dispersed throughout to increase solubility. Alternatively, certain linkers do not comprise any Serine residues, e.g., where the linker is subject to O-linked glycosyation. In some aspects, linkers can contain cysteine residues, for example, if dimerization of linkers is used to bring the domains of a bifunctional polypeptide into their properly folded configuration. In some aspects, a bifunctional polypeptide can comprise at least one, two, three, four, or more polypeptide linkers that join domains of the polypeptide.

In some aspects, a polypeptide linker can comprise 1-50 residues, 1-25 residues, 25-50 residues, or 30-50 residues. In some aspects, the polypeptide linker can comprise a portion of an Fc moiety. For example, in some aspects, the polypeptide linker can comprise a portion of immunoglobulin hinge domain of an IgG1, IgG2, IgG3, and/or IgG4 antibody or a variant thereof.

In some aspects, a polypeptide linker can comprise or consists of a gly-ser linker. As used herein, the term "gly-ser linker" refers to a peptide that consists of glycine and serine residues. An exemplary gly-ser linker comprises an amino acid sequence of the formula (Gly$_4$Ser)n, where n is an integer of at least one, two and up to, e.g., 3, 4, 5, 6, 10, 20, 50, 100, or more. In some aspects, a polypeptide linker can comprise at least a portion of a hinge region (e.g., derived from an IgG1, IgG2, IgG3, or IgG4 molecule) and a series of gly-ser amino acid residues (e.g., a gly-ser linker such as (Gly$_4$Ser)n).

When a multifunctional polypeptide, e.g., a multispecific binding molecule, comprises an scFv, a flexible linker can connect the heavy and light chains of the scFv. This flexible linker generally does not include a hinge portion, but rather, is a gly-ser linker or other flexible linker. The length and amino acid sequence of a flexible linker interconnecting domains of an scFv can be readily selected and optimized.

In certain aspects, a multifunctional polypeptide, e.g., a multispecific binding molecule, can comprise an anti-NGF scFv fragment which comprises, from N-terminus to C-terminus, a VH, a 15-amino acid linker sequence (GGGGS)$_3$, and a VL. In certain embodiments, the linker joining the VH and VL of the scFv is a 20 amino acid linker sequence (GGGGS)$_4$. In certain aspects the VH comprises the amino acid sequence of SEQ ID NO 3. In certain aspects the VL comprises the amino acid sequence of SEQ ID NO: 7. In certain embodiments, the VH comprises the amino acid sequence of any one of SEQ ID NOs: 24, 30, 32, 34, 36, 38, 40, 42, 44, 46, 48, 50, 52, 54, 56, 58, 60, 62, 64, 66, 68, 70, 72, 74, 76, 78, 80, 82, 84, 86, 94 and 96. In certain embodiments, the VL comprises the amino acid sequence of any one of SEQ ID NOs: 26, 31, 33, 35, 37, 39, 41, 43, 45, 47, 49, 51, 53, 55, 57, 59, 61, 63, 65, 67, 69, 71, 73, 75, 77, 79, 81, 83, 85, 87, 95 and 97. In certain aspects, the VH domain comprises an amino acid sequence at least 80%, 85%, 90%, 95%, 96%, 97%, 98%, or 99% identical to the amino acid sequence of any one of SEQ ID NOs: 3, 24, 30, 32, 34, 36, 38, 40, 42, 44, 46, 48, 50, 52, 54, 56, 58, 60, 62, 64, 66, 68, 70, 72, 74, 76, 78, 80, 82, 84, 86, 94 and 96. In certain aspects, the VL domain comprises an amino acid sequence at least 80%, 85%, 90%, 95%, 96%, 97%, 98%, or 99% identical to the amino acid sequence of any one of SEQ ID NOs: 7, 26, 31, 33, 35, 37, 39, 41, 43, 45, 47, 49, 51, 53, 55, 57, 59, 61, 63, 65, 67, 69, 71, 73, 75, 77, 79, 81, 83, 85, 87, 95 and 97.

In other aspects, the stability of the polypeptide can be improved by addition of an inter-chain disulphide bond between the VH domain and the VL domain by modifying certain residues within the VH and VL domain to cysteine residues. See for example, Michaelson, J. S., et al. (2009) *MAbs* 1, 128-41; Brinkmann, U., et al., (1993) *Proc Natl Acad Sci USA* 90, 7538-42; Young, N. M., et al., (1995) *FEBS Lett* 377, 135-9. For example, the glycine residue at positions 100, 101 or 102 of the VL can be modified to a cysteine residue and the glycine residue at position 44 of the VH can be modified to a cysteine residue.

A multifunctional polypeptide, e.g., a multispecific binding molecule as provided herein can include a TNFα antagonist domain. In certain aspects, a TNFα antagonist domain can inhibit the binding of TNFα to a TNF receptor (TNFR) on the surface of cells, thereby blocking TNF activity.

In certain aspects, the TNFα antagonist domain of a multifunctional polypeptide as provided herein is an anti-TNFα antibody or antigen-binding fragment thereof. In certain aspects, the anti-TNFα antibody is infliximab, adalimumab, certolizumab pegol, golimumab, or an antigen-binding fragment of any of these antibodies.

In certain aspects, the anti-TNFα antibody or fragment thereof binds to the same epitope as, can competitively inhibit, or can bind to TNFα with a greater affinity than any of anti-TNFα antibodies infliximab, adalimumab, certolizumab pegol, or golimumab, or an antigen-binding fragment of any of these antibodies. In certain aspects the anti-TNFα antibody is infliximab, adalimumab, certolizumab pegol, or golimumab, or an antigen-binding fragment of any of these antibodies. The structure and sequences of these anti-TNFα antibodies are easily available to the skilled artisan, and can be included in a multifunctional polypeptide, e.g., a multispecific binding molecule, as described herein without undue experimentation. An anti-TNFα antibody or fragment thereof included in a multifunctional polypeptide can be, e.g., humanized, chimeric, primatized, or fully human.

In certain aspects, the anti-TNFα antibody or fragment thereof comprises an antibody VH domain comprising the HCDR1, HCDR2, and HCDR3 domains of infliximab, adalimumab, certolizumab pegol, or golimumab, or variants of the infliximab, adalimumab, certolizumab pegol or golimumab heavy chain CDRs with up to one, two, three, four, five, or more amino acid substitutions, e.g., conservative amino acid substitutions.

In certain aspects, the anti-TNFα antibody or fragment thereof comprises an antibody VL domain comprising the LCDR1, LCDR2, and LCDR3 domains of infliximab, adalimumab, certolizumab pegol, or golimumab, or variants of the infliximab, adalimumab, certolizumab pegol, or golimumab heavy chain CDRs with up to one, two, three, four, five, or more amino acid substitutions, e.g., conservative amino acid substitutions.

In certain aspects, the anti-TNFα antibody or fragment thereof comprises an antibody VH domain comprising a VH amino acid sequence at least 80%, 85%, 90%, 95%, 96%, 97%, 98%, or 99% identical to the VH amino acid sequence of infliximab, adalimumab, certolizumab pegol, or golimumab. In some aspects the anti-TNFα antibody or fragment thereof comprises an antibody VH domain comprising the VH amino acid sequence of infliximab, adalimumab, certolizumab pegol, or golimumab.

In certain aspects, the anti-TNFα antibody or fragment thereof comprises an antibody VL domain comprising a VL amino acid sequence at least 80%, 85%, 90%, 95%, 96%, 97%, 98%, or 99% identical to the VL amino acid sequence of infliximab, adalimumab, certolizumab pegol, or golimumab. In some aspects the anti-TNFα antibody or fragment thereof comprises an antibody VL domain comprising the VL amino acid sequence of infliximab, adalimumab, certolizumab pegol, or golimumab.

In certain aspects, the anti-TNFα antibody or fragment thereof comprises an antibody VH domain comprising a VH amino acid sequence at least 80%, 85%, 90%, 95%, 96%, 97%, 98%, or 99% identical to the amino acid sequence of SEQ ID NO: 28. In some aspects, the anti-TNFα antibody or fragment thereof comprises an antibody VH domain comprising the VH amino acid sequence of SEQ ID NO: 28.

In certain aspects, the anti-TNFα antibody or fragment thereof comprises an antibody VH domain comprising a VL amino acid sequence at least 80%, 85%, 90%, 95%, 96%, 97%, 98%, or 99% identical to the amino acid sequence of SEQ ID NO: 29. In some aspects, the anti-TNFα antibody or fragment thereof comprises an antibody VL domain comprising the VL amino acid sequence of SEQ ID NO: 29.

A multifunctional polypeptide, e.g., a multispecific binding molecule, as provided by this disclosure can comprise a complete anti-TNFα antibody, i.e., an antibody comprising two complete heavy chains and two complete light chains in an $H_2L_2$ format. Where the anti-TNFα antibody is a complete antibody, one or more NGF antagonist domains can be fused to the N-terminus or C-terminus of one or more heavy chains of the anti-TNFα antibody or to the N-terminus or C-terminus of one or more light chains of the anti-TNFα antibody. Alternatively, a multifunctional polypeptide, e.g., a multispecific binding molecule, as provided by this disclosure can comprise an antigen-binding fragment of an anti-TNFα antibody. In certain aspects an anti-TNFα antibody fragment can comprise any portion of the antibody's constant domains or can comprise only the variable domains. Exemplary anti-TNFα antibody fragments for inclusion in a multifunctional polypeptide include, but are not limited to Fab fragments, Fab' fragments, F(ab)₂ fragments or single chain Fv (scFv) fragments.

In some aspects, the multifunctional molecule is ndimab varB, which is a molecule comprising a complete anti-TNFα antibody, i.e., an antibody comprising two complete heavy chains and two complete light chains in an $H_2L_2$ format, with MEDI-578 scFv fused to the C-terminus of the heavy chain of the anti-TNFα antibody. Ndimab varB comprises a light chain comprising the amino acid sequence of SEQ ID NO: 20, and a heavy chain comprising the amino acid sequence of SEQ ID NO: 22. In some aspects, the bifunctional molecule comprises a light chain comprising an amino acid sequence that is at least 80%, 85%, 90%, 95%, 96%, 97%, 98%, or 99% identical to SEQ ID NO: 20, and a heavy chain comprising an amino acid sequence that is at least 80%, 85%, 90%, 95%, 96%, 97%, 98%, or 99% identical to SEQ ID NO: 22.

In certain aspects, the anti-TNFα antibody is an scFv fragment, e.g. an scFv fragment derived from infliximab, adalimumab, certolizumab pegol, or golimumab, or a TNFα-binding variant thereof. An anti-TNFα scFv polypeptide can comprise the VH and VL domains in any order, either N—VH-VL-C, or N-VL-VH-C. ScFv molecules are typically engineered such that the VH and VL domains are connected via a flexible linker, and can assume a number of different structures, as described above. An anti-TNFα scFv polypeptide can be stabilized, also as described above.

In certain aspects, the TNFα antagonist is a TNFα-binding soluble fragment of a TNF receptor, e.g., TNFR-1 or TNFR-2, or a variant thereof or a soluble fragment thereof. In certain aspects, the soluble fragment of TNFR-1 is a 55 kD fragment. In certain embodiments, the soluble fragment of TNFR-2 is a 75 kD fragment. In certain aspects the TNF receptor fragment is fused to a heterologous polypeptide, e.g., an immunoglobulin Fc fragment, e.g., an IgG1 Fc domain. In certain aspects, the TNFα antagonist comprises an amino acid set forth in SEQ ID NO: 13, or a TNFα-binding fragment thereof. The TNFR-2 portion comprises amino acids 1 to 235 of SEQ ID NO: 13. In certain aspects, a variant of a TNFα-binding soluble fragment of TNFR-2 comprises an amino acid sequence at least 80%, 85%, 90%, 95%, 96%, 97%, 98%, 99%, or 100% identical to amino acids 1 to 235 of SEQ ID NO: 13. In certain aspects, a variant of a TNFα-binding soluble fragment of TNFR-2 comprises amino acids 1 to 235 of SEQ ID NO: 13, except for, e.g., 1, 2, 3, 4, 5, 10, 20, 20, 40, or 50 amino acid insertions, substitutions, or deletions. The IgG1 Fc portion comprises amino acids 236 to 467 of SEQ ID NO: 13. In certain aspects, the TNFα-binding soluble fragment of TNFR-2 can be fused to an Fc portion of any human or non-human antibody, or to any other protein or non-protein substance that would provide stability, e.g., albumin or polyethylene glycol. In certain aspects, a variant of a TNFα-binding soluble fragment of TNFR-2 comprises an amino acid sequence at least 80%, 85%, 90%, 95%, 96%, 97%, 98%, 99%, or 100% identical to amino acids 236 to 467 of SEQ ID NO: 13. In certain aspects, a variant of a TNFα-binding soluble fragment of TNFR-2 comprises amino acids 236 to 467 of SEQ ID NO: 13, except for, e.g., 1, 2, 3, 4, 5, 10, 20, 20, 40, or 50 amino acid insertions, substitutions, or deletions. In certain aspects, a variant of a TNFα-binding soluble fragment of TNFR-2 comprises an amino acid sequence at least 80%, 85%, 90%, 95%, 96%, 97%, 98%, 99%, or 100% identical to SEQ ID NO: 13. In certain aspects, a variant of a TNFα-binding soluble fragment of TNFR-2 comprises SEQ ID NO: 13, except for, e.g., 1, 2, 3, 4, 5, 10, 20, 20, 40, or 50 amino acid insertions, substitutions, or deletions.

In certain aspects, TNFα-binding soluble fragment of TNFR-2 is a single-chain fusion protein. In certain aspects the TNFα-binding soluble fragment of TNFR-2 is a dimer of two fusion proteins, associated, e.g., through disulfide bonds between the two Fc domains.

A multifunctional polypeptide, e.g., a multispecific binding molecule, as provided herein can have a variety of different structures and conformations. In one aspect, a multifunctional polypeptide as provided herein comprises a fusion protein where the NGF antagonist domain, as described above, is fused to the TNFα antagonist domain, as described above, through a flexible linker. Examples of linkers are described elsewhere herein. In certain aspects, the multifunctional polypeptide comprises a homodimer of the fusion protein.

In an exemplary aspect, a multifunctional polypeptide is provided in which the NGF antagonist is an anti-NGF scFv domain derived, e.g., from MEDI-578 and the TNFα antagonist is a soluble, TNFα-binding fragment of TNFR-2 fused at its carboxy-terminus to an immunoglobulin Fc domain. The anti-NGF scFv can be, in some aspects, fused to the carboxy-terminus of the immunoglobulin Fc domain via a linker. In certain aspects, monomers of this multifunctional polypeptide form a homodimer with each subunit comprising, from N-terminus to C-terminus, a TNFα-binding 75 kD fragment of TNFR-2, a human IgG1Fc domain, a 10-amino-acid linker (GGGGS)$_2$ (SEQ ID NO: 98), an anti-NGF VH comprising the amino acid sequence of SEQ ID NO 3, a 15-amino acid linker sequence (GGGGS)$_3$ (SEQ ID NO: 15), and an anti-NGF VL comprising the amino acid sequence of SEQ ID NO: 7. In one aspect, the multifunctional polypeptide is TNFR2-Fc_VH#4, which comprises a homodimer of a fusion polypeptide comprising the amino acid sequence of SEQ ID NO: 14. In some aspects, the multifunctional polypeptide comprises a homodimer of a fusion polypeptide comprising an amino acid sequence that is at least 80%, 85%, 90%, 95%, 96%, 97%, 98%, 99% identical to SEQ ID NO: 14.

In another exemplary aspect, the multifunctional polypeptide comprises, from N-terminus to C-terminus, a TNFα-binding 75 kD fragment of TNFR-2, a human IgG1Fc domain, a 10-amino-acid linker (GGGGS)$_2$ (SEQ ID NO: 98), an anti-NGF VH comprising the amino acid sequence of SEQ ID NO 94, a 20-amino acid linker sequence (GGGGS)$_4$ (SEQ ID NO: 19), and an anti-NGF VL comprising the amino acid sequence of SEQ ID NO: 95. In some aspect, the multifunctional polypeptide is TNFR2-Fc_varB, which comprises a homodimer of a fusion polypeptide comprising the amino acid sequence of SEQ ID NO: 17. In some aspects, the multifunctional polypeptide comprises a homodimer of a fusion polypeptide comprising an amino acid sequence that is at least 80%, 85%, 90%, 95%, 96%, 97%, 98%, 99% identical to SEQ ID NO: 17.

Polypeptides

Polypeptides as provided herein, e.g., multifunctional polypeptides comprising an NGF antagonist domain and a TNFα antagonist domain, or individual polypeptides comprising an NGF antagonist domain and a TNFα antagonist domain, respectively, can be recombinant polypeptides, derived from natural polypeptides, or synthetic polypeptides. It will be recognized in the art that some amino acid sequences can be varied without significant effect of the structure or function of the protein. Thus, the disclosure further provides variations of polypeptides provided herein having substantial activity or which include NGF antagonist domains and TNFα antagonist domains. Such mutants include deletions, insertions, inversions, repeats, and type substitutions.

The polypeptides and analogs can be further modified to contain additional chemical moieties not normally part of the protein. Those derivatized moieties can improve the solubility, the biological half-life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

In certain aspects, a multifunctional polypeptide provided herein can include an NGF or TNFα binding domain that is not an antibody. A variety of methods for identifying and producing non-antibody polypeptides that bind with high affinity to a protein target are known in the art. See, e.g., Skerra, Curr. Opin. Biotechnol., 18:295-304 (2007), Hosse et al., Protein Science, 15:14-27 (2006), Gill et al., Curr. Opin. Biotechnol., 17:653-658 (2006), Nygren, FEBS J., 275:2668-76 (2008), and Skerra, FEBS J., 275:2677-83 (2008), each of which is incorporated by reference herein in its entirety. In certain aspects, phage display technology can be used to identify/produce the suitable multifunctional polypeptides. In certain aspects, a multifunctional polypeptide, e.g., a multispecific binding molecule provided herein can comprise a protein scaffold of a type selected from the group consisting of protein A, a lipocalin, a fribronectin domain, an ankyrin consensus repeat domain, and thioredoxin.

Polynucleotides, Vectors, and Host Cells

This disclosure provides nucleic acid molecules comprising polynucleotides that encode a multifunctional polypeptide comprising an NGF antagonist domain and a TNFα antagonist domain. This disclosure further provides nucleic acid molecules comprising polynucleotides that encode individual polypeptides comprising, respectively, an NGF antagonist and a TNFα antagonist. In certain aspects such polynucleotides encode a peptide domain that specifically binds NGF or a fragment thereof, and also binds TNFα or a fragment thereof. For example, this disclosure provides a polynucleotide that encodes a polypeptide domain comprising an anti-NGF antibody or an antigen-binding fragment thereof, and a polypeptide domain comprising a TNFα antagonist, such as an anti-TNFα antibody or antigen-binding fragment thereof, or a soluble TNFα-binding portion of a TNF receptor, e.g., TNFR2. Polynucleotides can be in the form of RNA or in the form of DNA. DNA includes cDNA, genomic DNA, and synthetic DNA; and can be double-stranded or single-stranded, and if single stranded can be the coding strand or non-coding (anti-sense) strand.

In some embodiments, the isolated polynucleotide that encodes a multifunctional polypeptide described herein comprises the nucleotide sequence of SEQ ID NO: 16, 18 or 99, or fragments thereof, or a sequence at least 80%, 85%, 90%, 95%, 96%, 97%, 98%, or 99% identical to SEQ ID NO: 16, 18 or 99, or fragments thereof.

The isolated polypeptides described herein can be produced by any suitable method known in the art. Such methods range from direct protein synthetic methods to constructing a DNA sequence encoding isolated polypeptide sequences and expressing those sequences in a suitable transformed host. In some aspects, a DNA sequence is constructed using recombinant technology by isolating or synthesizing a DNA sequence encoding a multifunctional polypeptide comprising an NGF antagonist domain and a TNFα antagonist domain, or individual polypeptides comprising an NGF antagonist domain and a TNFα antagonist domain, respectively. Accordingly, this disclosure provides an isolated polynucleotide that encodes a bifunctional polypeptide comprising an NGF antagonist domain and a TNFα antagonist domain as described in detail above. Further provided are isolated polynucleotides that encode individual polypeptides that comprise, respectively, an NGF antagonist domain and a TNFα antagonist domain.

In some aspects a DNA sequence encoding a multifunctional polypeptide, e.g., a multispecific binding molecule of interest or individual polypeptides comprising an NGF antagonist domain and a TNFα antagonist domain, respectively can be constructed by chemical synthesis using an oligonucleotide synthesizer. Such oligonucleotides can be designed based on the amino acid sequence of the desired multifunctional polypeptide and selecting those codons that are favored in the host cell in which the recombinant polypeptide of interest will be produced. Standard methods can be applied to synthesize an isolated polynucleotide sequence encoding a multifunctional polypeptide of interest. For example, a complete amino acid sequence can be used to construct a back-translated gene. Further, a DNA oligomer containing a nucleotide sequence coding for the particular multifunctional polypeptide or individual polypeptides can be synthesized. For example, several small oligonucleotides coding for portions of the desired polypeptide can be synthesized and then ligated. The individual oligonucleotides typically contain 5' or 3' overhangs for complementary assembly.

In certain aspects, polynucleotides provided herein can comprise the coding sequence for the mature polypeptide fused in the same reading frame to a marker sequence that allows, for example, for purification of the encoded polypeptide. For example, the marker sequence can be a hexahistidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used.

Polynucleotides provided herein can further contain alterations in the coding regions, non-coding regions, or both. In some aspects the polynucleotide variants contain alterations that produce silent substitutions, additions, or deletions, but do not alter the properties or activities of the encoded polypeptide. In some aspects, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

Vectors and cells comprising the polynucleotides described herein are also provided. Once assembled (by synthesis, site-directed mutagenesis or another method), the polynucleotide sequences encoding a particular isolated polypeptide of interest can be inserted into an expression vector and operatively linked to an expression control sequence appropriate for expression of the protein in a desired host. This disclosure provides such vectors. Nucleotide sequencing, restriction mapping, and expression of a biologically active polypeptide in a suitable host can confirm proper assembly. As is well known in the art, in order to obtain high expression levels of a transfected gene in a host, the gene must be operatively linked to transcriptional and translational expression control sequences that are functional in the chosen expression host.

In certain aspects, recombinant expression vectors can be used to amplify and express DNA encoding multifunctional polypeptides, e.g., multispecific binding molecules, comprising an NGF antagonist domain and a TNFα antagonist domain, or individual polypeptides comprising an NGF antagonist domain and a TNFα antagonist domain, respectively. Recombinant expression vectors are replicable DNA constructs that have synthetic or cDNA-derived DNA fragments encoding a multifunctional polypeptide or individual polypeptides comprising an NGF antagonist domain and a TNFα antagonist domain, respectively, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR 1, pBR322, pMB9 and their derivatives, wider host range plasmids, such as M13 and filamentous single-stranded DNA phages.

This disclosure further provides host cells comprising polynucleotides encoding the polypeptides provided herein. Suitable host cells for expression of the polypeptides provided herein include prokaryotes, yeast, insect or higher eukaryotic cells under the control of appropriate promoters. Prokaryotes include gram negative or gram-positive organisms, for example *E. coli* or bacilli. Higher eukaryotic cells include established cell lines of mammalian origin as described below. Cell-free translation systems can also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems can also be advantageously employed to express recombinant protein. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

This disclosure further provides a method of producing the multifunctional polypeptide as described herein, or for producing individual polypeptides comprising, respectively an NGF antagonist, and a TNFα antagonist. The method entails culturing a host cell as described above under conditions promoting expression of the multifunctional polypeptide or individual polypeptides, and recovering the multifunctional polypeptide or individual polypeptides.

For long-term, high-yield production of recombinant proteins, stable expression is appropriate. For example, cell lines which stably express the multifunctional polypeptide may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may be used to engineer cell lines which express the multifunctional polypeptide.

In certain embodiments, multifunctional polypeptides presented herein are expressed in a cell line with transient expression of the multifunctional polypeptide. Transient transfection is a process in which the nucleic acid introduced into a cell does not integrate into the genome or chromosomal DNA of that cell but is maintained as an extrachromosomal element, e.g. as an episome, in the cell. Transcription processes of the nucleic acid of the episome are not affected and a protein encoded by the nucleic acid of the episome is produced.

The cell line, either stable or transiently transfected, is maintained in cell culture medium and conditions known in the art resulting in the expression and production of polypeptides. In certain embodiments, the mammalian cell culture media is based on commercially available media formulations, including, for example, DMEM or Ham's F12. In some embodiments, the cell culture media is modified to support increases in both cell growth and biologic protein expression. As used herein, the terms "cell culture medium," "culture medium," and "medium formulation" refer to a nutritive solution for the maintenance, growth, propagation, or expansion of cells in an artificial in vitro environment outside of a multicellular organism or tissue. Cell culture medium may be optimized for a specific cell culture use, including, for example, cell culture growth medium which is formulated to promote cellular growth, or cell culture production medium which is formulated to promote recombinant protein production. The terms nutrient, ingredient, and component may be used interchangeably to refer to the constituents that make up a cell culture medium.

In various embodiments, the cell lines are maintained using a fed batch method. As used herein, "fed batch method," refers to a method by which a fed batch cell culture is supplied with additional nutrients after first being incubated with a basal medium. For example, a fed batch method may comprise adding supplemental media according to a determined feeding schedule within a given time period. Thus, a "fed batch cell culture" refers to a cell culture where the cells, typically mammalian, and culture medium are supplied to the culturing vessel initially and additional culture nutrients are fed, continuously or in discrete increments, to the culture during culturing, with or without periodic cell and/or product harvest before termination of culture.

In some embodiments, the cell culture medium comprises a basal medium and at least one hydrolysate, e.g., soy-based, hydrolysate, a yeast-based hydrolysate, or a combination of the two types of hydrolysates resulting in a modified basal medium. The additional nutrients may sometimes include only a basal medium, such as a concentrated basal medium, or may include only hydrolysates, or concentrated hydrolysates. Suitable basal media include, but are not limited to Dulbecco's Modified Eagle's Medium (DMEM), DME/F12, Minimal Essential Medium (MEM), Basal Medium Eagle (BME), RPMI 1640, F-10, F-12, .alpha.-Minimal Essential Medium (.alpha.-MEM), Glasgow's Minimal Essential Medium (G-MEM), PF CHO (see, e.g., CHO protein free medium (Sigma) or EX-CELL™ 325 PF CHO Serum-Free Medium for CHO Cells Protein-Free (SAFC Bioscience), and Iscove's Modified Dulbecco's Medium. Other examples of basal media which may be used in the technology herein include BME Basal Medium (Gibco-Invitrogen; Dulbecco's Modified Eagle Medium (DMEM, powder) (Gibco-Invitrogen (#31600)).

In certain embodiments, the basal medium may be is serum-free, meaning that the medium contains no serum (e.g., fetal bovine serum (FBS), horse serum, goat serum, or any other animal-derived serum known to one skilled in the art) or animal protein free media or chemically defined media.

The basal medium may be modified in order to remove certain non-nutritional components found in standard basal medium, such as various inorganic and organic buffers, surfactant(s), and sodium chloride. Removing such components from basal cell medium allows an increased concentration of the remaining nutritional components, and may improve overall cell growth and protein expression. In addition, omitted components may be added back into the cell culture medium containing the modified basal cell medium according to the requirements of the cell culture conditions. In certain embodiments, the cell culture medium contains a modified basal cell medium, and at least one of the following nutrients, an iron source, a recombinant growth factor; a buffer; a surfactant; an osmolarity regulator; an energy source; and non-animal hydrolysates. In addition, the modified basal cell medium may optionally contain amino acids, vitamins, or a combination of both amino acids and vitamins. In some embodiments, the modified basal medium further contains glutamine, e.g, L-glutamine, and/or methotrexate.

In some embodiments, protein production is conducted in large quantity by a bioreactor process using fed-batch, batch, perfusion or continuous feed bioreactor methods known in the art. Large-scale bioreactors have at least 50 L liters of capacity, sometimes about more than 500 liters or 1,000 to 100,000 liters of capacity. These bioreactors may use agitator impellers to distribute oxygen and nutrients. Small scale bioreactors refers generally to cell culturing in no more than approximately 100 liters in volumetric capacity, and can range from about 1 liter to about 100 liters. Alternatively, single-use bioreactors (SUB) may be used for either large-scale or small scale culturing.

Temperature, pH, agitation, aeration and inoculum density may vary depending upon the host cells used and the recombinant protein to be expressed. For example, a recombinant protein cell culture may be maintained at a temperature between 30 and 45 degrees Celsius. The pH of the culture medium may be monitored during the culture process such that the pH stays at an optimum level, which may be for certain host cells, within a pH range of 6.0 to 8.0. An impellor driven mixing may be used for such culture methods for agitation. The rotational speed of the impellor may be approximately 50 to 200 cm/sec tip speed, but other airlift or other mixing/aeration systems known in the art may be used, depending on the type of host cell being cultured. Sufficient aeration is provided to maintain a dissolved oxygen concentration of approximately 20% to 80% air saturation in the culture, again, depending upon the selected host cell being cultured. Alternatively, a bioreactor may sparge air or oxygen directly into the culture medium. Other methods of oxygen supply exist, including bubble-free aeration systems employing hollow fiber membrane aerators.

Protein Purification

The proteins produced by a transformed host as described above can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems that secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify an NGF-binding agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying recombinant polypeptides also include, for example, those described in U.S. Patent Publication No. 2008/0312425, 2008/0177048, and 2009/0187005, each of which is hereby incorporated by reference herein in its entirety.

Methods of Use and Pharmaceutical Compositions

This disclosure provides methods for controlling or treating pain in a subject, comprising administering a therapeutically effective amount of a TNFα and NGF antagonist multifunctional polypeptide, e.g., a multispecific binding molecule, as provided herein or comprising co-administration of a TNFα antagonist and an NGF antagonist. In certain aspects, the subject is a human.

This disclosure further provides pharmaceutical compositions comprising a TNFα and NGF antagonist multifunctional polypeptide, e.g., a multispecific binding molecule, as provided herein or comprising a combination of a TNFα antagonist and an NGF antagonist as provided herein. In certain aspects, the pharmaceutical compositions further comprise a pharmaceutically acceptable vehicle. These pharmaceutical compositions are useful in treating pain, e.g., neuropathic and inflammatory (e.g., osteo or rheumatoid-arthritic) pain.

The multifunctional polypeptides and compositions comprising an NGF antagonist and a TNFα antagonist provided herein can be useful in a variety of applications including, but not limited to, the control or treatment of pain, e.g., neuropathic pain. The methods of use may be in vitro, ex vivo, or in vivo methods.

In certain aspects, the disease, disorder, or condition treated with the NGF-binding agent (e.g., an antibody or polypeptide) is associated with pain. In certain aspects, the pain is associated with chronic nociceptive pain, chronic lower back pain, neuropathic pain, cancer pain, postherpetic neuralgia (PHN) pain, or visceral pain conditions.

This disclosure provides a method for controlling pain in a subject, comprising administering to a subject in need of pain control an effective amount of a nerve growth factor (NGF) antagonist and a tumor necrosis factor (TNFα) antagonist, wherein the administration can control pain in the subject more effectively than an equivalent amount of the NGF antagonist or the TNFα antagonist administered alone.

In certain aspects, the administration is a co-administration of an NGF antagonist and a TNFα antagonist as a combination therapy. As discussed elsewhere herein, the individual components can be administered simultaneously or sequentially. The individual NGF antagonist or the TNFα antagonist can be any NGF or TNFα antagonists provided herein, e.g., a soluble NGF-binding TrkA receptor fragment, an anti-NGF antibody or antigen-binding fragment thereof, a soluble TNFα-binding fragment of a TNF receptor, e.g., TNFR-2, or an anti-TNFα antibody or fragment thereof, e.g., infliximab, adalimumab, certolizumab pegol, golimumab, or an antigen-binding fragment of any of these antibodies.

The co-administration can comprise various doses of each of the antagonists as needed to control pain. In some aspects, the co-administration can include lower doses or less frequent doses of each component than would be normally administered as an individual therapy, thereby providing for additional safety, convenience, and economy.

In certain aspects, the method of controlling pain as provided herein comprises administration of a multifunctional polypeptide, e.g., a multispecific binding molecule, comprising a NGF antagonist domain and a TNFα antagonist domain. Exemplary multifunctional polypeptides for use in this method are described in detail herein. Based on the disclosure, additional multifunctional polypeptides useful in this method will be apparent to the person of ordinary skill in the art.

By controlling pain "more effectively" than the components administered alone it is meant that the combination treatment is more effective at controlling pain than equivalent amounts of either the NGF antagonist or the TNFα antagonist administered individually. In certain aspects, and as described in more detail below, the method of controlling pain provided herein can provide synergistic efficacy, e.g., the effect of the administration of both the NGF antagonist and the TNFα antagonist can provide more than an additive effect, or can be effective where neither the NGF antagonist nor the TNFα antagonist are effective individually. In certain aspects the combination can allow for dose sparing, e.g., the effective dosages of the individual components when co-administered can be less than the effective doses of either component individually.

In certain aspects, the method of controlling pain provided herein is at least 5%, 10%, 20%, 30%, 40%, 50%, 60%, 70% 80%, 90%, or 100% more effective at controlling pain in the subject than an equivalent amount of the NGF antagonist or the TNFα antagonist administered alone. In certain aspects, dosages of the individual NGF antagonist or the TNFα antagonist co-administered to the subject or the dose of the relative dose of the NGF antagonist or the TNFα antagonist provided upon administration of a bifunctional polypeptide provided herein can be lower, e.g., 5%, 10%, 20%, 30%, 40%, 50% 60%, 70%, 80% or 90% lower than the dosages necessary for the components administered alone.

The efficacy of pain control can be measured by asking a patient to rate the quality and intensity of pain experienced according to a number of different scales. A verbal pain scale uses words to describe a range from no pain, mild pain, moderate pain and severe pain with a score from 0-3 assigned to each. Alternatively a patient may be asked to rate their pain according to a numerical pain scale from 0 (no pain) to 10 (worst possible pain). On a visual analog scale (VAS) a vertical or horizontal line has words to describe pain from no pain to worst possible pain and the patient is asked to mark the line at the point that represents their current level of pain. The McGill pain index enables patients to describe both the quality and intensity of pain by selecting words that best describe their pain from a series of short lists e.g. pounding, burning, pinching. Other pain scales can be used for adults who experience difficulty using VAS or numerical scales e.g. FACES or for non-verbal patients e.g. Behavioural rating scale. The functional activity score relates how impeded a patient is by their pain by asking them to carry out a task related to the painful area. Improvements in pain score using these types of scale would potentially indicate an improvement in efficacy of an analgesic.

According to the method of controlling pain provided herein, the administration is sufficient to control pain in a subject in need of pain control, e.g., the co-administration of a NGF antagonist and a TNFα antagonist, or administration of a multifunctional polypeptide, e.g., a multispecific binding molecule comprising an NGF antagonist domain and a TNFα antagonist domain can prevent, reduce, ameliorate, or eliminate pain in the subject. In certain aspects, the pain can be acute pain, short-term pain, persistent or chronic nociceptive pain, or persistent or chronic neuropathic pain.

In certain aspects, formulations are prepared for storage and use by combining a TNFα and NGF antagonist multifunctional polypeptide, e.g., a multispecific binding molecule as provided herein or a combination of a TNFα antagonist and an NGF antagonist as provided herein, with a pharmaceutically acceptable vehicle (e.g., carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes (e.g., Zn-protein complexes); and non-ionic surfactants such as TWEEN or polyethylene glycol (PEG).

Multifunctional polypeptides of the present disclosure may be formulated in liquid, semi-solid or solid forms depending on the physicochemical properties of the molecule and the route of delivery. Formulations may include excipients, or combinations of excipients, for example: sugars, amino acids and surfactants. Liquid formulations may include a wide range of polypeptide concentrations and pH. Solid formulations may be produced by lyophilisation, spray drying, or drying by supercritical fluid technology, for example. In some embodiments, any of the formulations described herein is a lyophilized formulation.

In a specific embodiment, a multifunctional polypeptide of the disclosure is formulated in 20 mM sodium phosphate, 50 mM L-arginine-HCL, 150 mM sucrose, 0.03% (w/v) polysorbate 80, pH 6.5.

A pharmaceutical composition provided herein can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

A TNFα and NGF antagonist multifunctional polypeptide as provided herein or a combination of a TNFα antagonist and an NGF antagonist as provided herein can be further combined in a pharmaceutical combination formulation, or dosing regimen as combination therapy, with a second (or third) compound having anti-nociceptive properties.

For the treatment of pain, the appropriate dosage of a TNFα and NGF antagonist multifunctional polypeptide, e.g., a multispecific binding molecule as provided herein or a combination of a TNFα antagonist and an NGF antagonist as provided herein depends on the type of pain to be treated, the severity and course of the pain, the responsiveness of the pain, whether the multifunctional polypeptide or polypeptide combination is administered for therapeutic or prophylactic purposes, previous therapy, patient's clinical history, and so on all at the discretion of the treating physician. The multifunctional polypeptide or polypeptide combination can be administered one time or over a series of treatments lasting from several days to several months to maintain effective pain control. Optimal dosing schedules can be calculated from measurements of drug accumulation in the body of the patient and will vary depending on the relative potency of an individual antibody or polypeptide. The administering physician can easily determine optimum dosages, dosing methodologies and repetition rates.

Administration of a multifunctional polypeptide, e.g., a multispecific binding molecule, or polypeptide combination therapy as provided herein can provide "synergy" and prove "synergistic", i.e. the effect achieved when the active ingredients used together is greater than the sum of the effects that results from using the compounds separately. A synergistic effect can be attained when the active ingredients are: (1) administered as a single, multifunctional fusion polypeptide; (2) co-formulated and administered or delivered simultaneously in a combined, unit dosage formulation; (3) delivered by alternation or in parallel as separate formulations; or (4) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, whereas in combination therapy, effective dosages of two or more active ingredients are administered together.

Pain

In its broadest usage, "pain" refers to an experiential phenomenon that is highly subjective to the individual experiencing it, and is influenced by the individual's mental state, including environment and cultural background. "Physical" pain can usually be linked to a stimulus perceivable to a third party that is causative of actual or potential tissue damage. In this sense, pain can be regarded as a "sensory and emotional experience associated with actual or potential tissue damage, or described in terms of such damage," according to the International Association for the Study of Pain (IASP). However, some instances of pain have no perceivable cause. For example, psychogenic pain, including exacerbation of a pre-existing physical pain by psychogenic factors or syndromes of a sometimes persistent, perceived pain in persons with psychological disorders without any evidence of a perceivable cause of pain.

Types of Pain

Pain includes nociceptive pain, neuropathic/neurogenic pain, breakthrough pain, allodynia, hyperalgesia, hyperesthesia, dysesthesia, paresthesia, hyperpathia, phantom limb pain, psychogenic pain, anesthesia dolorosa, neuralgia, neuritis. Other categorizations include malignant pain, anginal pain, and/or idiopathic pain, complex regional pain syndrome I, complex regional pain syndrome II. Types and symptoms of pain need not be mutually exclusive. These terms are intended as defined by the IASP.

Nociceptive pain is initiated by specialized sensory nociceptors in the peripheral nerves in response to noxious stimuli, encoding noxious stimuli into action potentials. Nociceptors, generally on Aδ fibers and (Polymodal) C fibers, are free nerve endings that terminate just below the skin, in tendons, joints, and in body organs. The dorsal root ganglion (DRG) neurons provide a site of communication between the periphery and the spinal cord. The signal is processed through the spinal cord to the brainstem and thalamic sites and finally to the cerebral cortex, where it usually (but not always) elicits a sensation of pain. Nociceptive pain can result from a wide variety of a chemical, thermal, biological (e.g., inflammatory) or mechanical events that have the potential to irritate or damage body tissue, which are generally above a certain minimal threshold of intensity required to cause nociceptive activity in nociceptors.

Neuropathic pain is generally the result of abnormal functioning in the peripheral or central nervous system, giving rise to peripheral or central neuropathic pain, respectively. Neuropathic pain is defined by the IASP as pain initiated or caused by a primary lesion or dysfunction in the nervous system. Neuropathic pain often involves actual damage to the nervous system, especially in chronic cases. Inflammatory nociceptive pain is generally a result of tissue damage and the resulting inflammatory process. Neuropathic pain can persist well after (e.g., months or years) beyond the apparent healing of any observable damage to tissues.

In cases of neuropathic pain, sensory processing from an affected region can become abnormal and innocuous stimuli (e.g., thermal, touch/pressure) that would normally not cause pain may do so (i.e., allodynia) or noxious stimuli may elicit exaggerated perceptions of pain (i.e., hyperalgesia) in response to a normally painful stimulus. In addition, sensations similar to electric tingling or shocks or "pins and needles" (i.e., paresthesias) and/or sensations having unpleasant qualities (i.e., dysesthesias) may be elicited by normal stimuli. Breakthrough pain is an aggravation of pre-existing chronic pain. Hyperpathia is a painful syndrome resulting from an abnormally painful reaction to a stimulus. The stimulus in most of the cases is repetitive with an increased pain threshold, which can be regarded as the least experience of pain that a patient can recognize as pain.

Examples of neuropathic pain include tactile allodynia (e.g., induced after nerve injury) neuralgia (e.g., post herpetic (or post-shingles) neuralgia, trigeminal neuralgia), reflex sympathetic dystrophy/causalgia (nerve trauma), components of cancer pain (e.g., pain due to the cancer itself or associated conditions such as inflammation, or due to treatment such as chemotherapy, surgery or radiotherapy), phantom limb pain, entrapment neuropathy (e.g., carpal tunnel syndrome), and neuropathies such as peripheral neuropathy (e.g., due to diabetes, HIV, chronic alcohol use, exposure to other toxins (including many chemotherapies), vitamin deficiencies, and a large variety of other medical conditions). Neuropathic pain includes pain induced by expression of pathological operation of the nervous system following nerve injury due to various causes, for example, surgical operation, wound, shingles, diabetic neuropathy, amputation of legs or arms, cancer, and the like. Medical conditions associated with neuropathic pain include traumatic nerve injury, stroke, multiple sclerosis, syringomyelia, spinal cord injury, and cancer.

A pain-causing stimulus often evokes an inflammatory response which itself can contribute to an experience of pain. In some conditions pain appears to be caused by a complex mixture of nociceptive and neuropathic factors. For example, chronic pain often comprises inflammatory nociceptive pain or neuropathic pain, or a mixture of both. An initial nervous system dysfunction or injury may trigger the neural release of inflammatory mediators and subsequent neuropathic inflammation. For example, migraine headaches can represent a mixture of neuropathic and nociceptive pain. Also, myofascial pain is probably secondary to nociceptive input from the muscles, but the abnormal muscle activity may be the result of neuropathic conditions.

Kits Comprising TNFα and NGF Antagonists

This disclosure provides kits that comprise a TNFα and NGF antagonist multifunctional polypeptide, e.g., a multispecific binding molecule, as provided herein or a combination of a TNFα antagonist and an NGF antagonist as provided herein, that can be used to perform the methods described herein. In certain aspects, a kit comprises at least multifunctional fusion polypeptide comprising a TNFα antagonist and an NGF antagonist, e.g., a polypeptide comprising an amino acid sequence of SEQ ID NO: 14 or 17, in one or more containers, or a combination of an NGF antagonist, e.g., MEDI-578, and a TNFα antagonist, e.g., an anti-TNFα antibody such as infliximab or adalimumab, or a TNFα-binding soluble fragment of a TNF receptor, e.g., TNFR2-Fc. One skilled in the art will readily recognize that the disclosed TNFα and NGF antagonists provided herein can be readily incorporated into one of the established kit formats, which are well known in the art.

EXAMPLES

The disclosure now being generally described, it will be more readily understood by reference to the following examples, which are included merely for purposes of illustration of certain aspects and embodiments of the present disclosure, and are not intended to limit the disclosure.

Figure 1A:
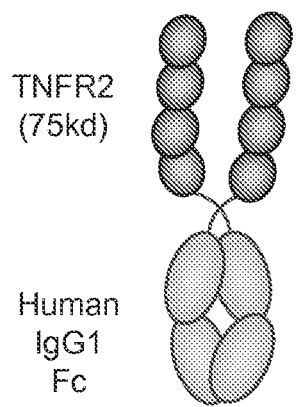
Figure 1B:
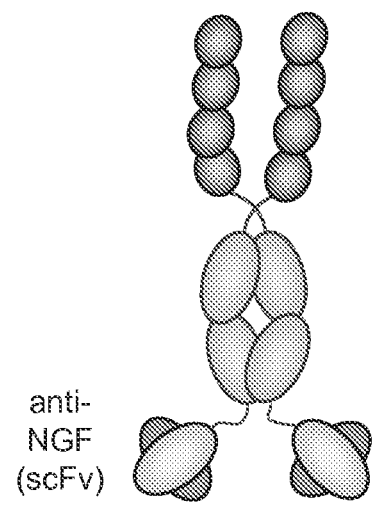

Example 1—Construction and Characterization of an Anti NGF scFv/TNFR2-Fc Multispecific Binding Molecule A multifunctional molecule, specifically, a multispecific binding molecule comprising an anti NGF antibody domain and a TNFR2-Fc domain was produced as follows. The anti-NGF antibody scFv fragment was fused to the C-terminus of a TNFR2-Fc fusion protein (SEQ ID NO: 13) via the heavy chain CH3 domain, according to the Bs3Ab format described in Dimasi, N., et al., *J Mol Biol.* 393:672-92 (2009), and in PCT Publication No. WO 2013/070565. A diagram of the structure is shown in FIG. 1. DNA constructs encoding the TNFR2-Fc polypeptide and the multispecific binding molecule were synthesized by GeneArt (Invitrogen). For the multispecific binding molecule, an anti-NGF scFv comprising the VH (SEQ ID NO: 3) and VL (SEQ ID NO: 7) domains of MEDI-578 joined together via a 15 amino acid linker sequence (GGGGS)$_3$ (SEQ ID NO: 15) was constructed. The N-terminus of the scFv was fused, via a 10-amino-acid linker sequence (GGGGS)$_2$, to the C-terminus of SEQ ID NO: 13. This multispecific binding molecule is referred to herein as TNFR2-Fc_VH#4. The DNA construct encoding the multispecific binding molecule was engineered to contain a stop codon and an EcoRI restriction site at the 3' end for cloning into the Bs3Ab expression vector. The DNA sequence encoding TNFR2-Fc_VH#4 is presented as SEQ ID NO: 16 and its amino acid sequence as SEQ ID NO: 14.

The thermostability of the TNF-NGF multispecific binding molecule was improved by the addition of an inter-chain disulphide bond between the VH and VL domains of the MEDI-578 scFv portion of the multispecific binding molecule. This was done by introducing a G→C mutation at amino acid 44 of the VH domain (SEQ ID NO: 94) and at amino acid 102 of the VL domain (SEQ ID NO: 95). This clone was designated TNFR2-Fc_varB. The amino acid sequence of TNFR2-Fc_varB is presented as SEQ ID NO: 17. A DNA sequence encoding TNFR2-Fc_varB is presented as SEQ ID NO: 18. A codon optimized DNA sequence encoding TNFR2-Fc_varB is presented in SEQ ID NO: 99. TNFR2-Fc_varB further differs from TNFR2-Fc_VH#4 in that the 15 amino acid linker sequence (GGGGS)$_3$ joining the VH and VL of the scFv portion is replaced with a 20 amino acid linker (GGGGS)$_4$ (SEQ ID NO: 19). Differential scanning fluorimetry (DSF) was used to measure the Tm of TNFR2-Fc_VH#4 and TNFR2-Fc_varB. This method measures the incorporation of a fluorescent dye, Sypro Orange (Invitrogen), which binds to hydrophobic surfaces revealed during protein domain unfolding upon exposure to elevated temperatures. In the DSF assay, the Tm of TNFR2-Fc_VH#4 was 62° C., whereas the Tm of TNFR2-Fc_varB was 66° C. Therefore, the addition of the inter-chain disulphide bond in the MEDI-578 scFv portion of the multispecific molecule improved the thermostability of the molecule by 4° C.

The TNFR2-Fc protein and TNFR2-Fc_VH#4 were transiently expressed in suspension CHO cells using Polyethylenimine (PEI) (Polysciences) as the transfection reagent. The cells were maintained in CD-CHO medium (Life Technologies). Culture harvests from small-scale transfections were purified using 1 ml HiTrap MabSelect SuRe™ affinity chromatography in accordance with the manufacturer's protocol (GE Healthcare) and were subsequently buffer exchanged in 1% sucrose, 100 mM NaCl, 25 mM L-arginine hydrochloride, and 25 mM sodium phosphate (pH 6.3). The purity of the recombinant proteins was analyzed using SDS-PAGE under reducing conditions and using analytical size-exclusion chromatography (see method below), and concentrations were determined by reading the absorbance at 280 nm using theoretically determined extinction coefficients.

Small scale transient expression and protein A column purification of the TNFR2-Fc fusion protein and the TNF-NGF multispecific construct, TNFR2-Fc_VH#4, produced yields of 36.6 and 79.9 mg L$^{-1}$ respectively.

A larger batch of TNFR2-Fc_VH#4 was produced as follows. A crude culture harvest from a large-scale transfection (up to 6 L) was filtered using depth filtration and loaded onto a 1.6×20 cm Protein A agarose column (GE Healthcare) pre-equilibrated with buffer A (phosphate buffered saline pH 7.2). The column was then washed with buffer A and the product eluted in a step gradient of buffer B (50 mM Sodium Acetate pH<4.0). The product was further purified by loading onto a 1.6×20 cm Poros HS 50 column (Applied Biosystems) pre-equilibrated in buffer C (50 mM Sodium Acetate buffer pH<5.5), washed in buffer C and then subsequently the product was eluted in a linear gradient from 0 to 1 M NaCl in 50 mM Sodium Acetate buffer pH<5.5. The resulting eluates were analysed by Size Exclusion HPLC. The protein concentration was determined by A280 spectroscopy with a Beckman DU520 spectrophotometer using a calculated extinction coefficient of 1.36.

Methods for Characterization of TNFR2-Fc_VH#4

Western blot analysis was carried out using standard protocols. Proteins were transferred onto the polyvinylidene fluoride membrane (Life Technologies) using the Xcell SureLock™ system (Invitrogen) according to the manufacturer's instructions. The membrane was blocked with 3% (w/v) skim milk powder in phosphate-buffered saline (PBS) for 1 h at room temperature. Western blots were developed using standard protocols with HRP-conjugated anti-human IgG Fc-specific antibody (Sigma).

Size exclusion HPLC was performed using a Gilson HPLC system (Isocratic pump-307, UV/Vis-151 detector, Liquid Handler-215 and Injection Module-819) with a Phenomenex BioSep-SEC-S3000 (300×7.8 mm) column with a mobile phase of D-PBS (life Technologies) at a flow rate of 1 ml/min. Twenty-five L samples were injected onto the column and separation of protein species was monitored at A280 nm Enzymatic deglycosylation of small-scale purified TNFR2-Fc_VH#4 was performed using an EDGLY kit (Sigma Aldrich) according to the manufacturer's protocols. Proteins were deglycosylated under both denatured and native conditions. For denatured proteins, 30 μg of protein was deglycosylated with PNGase F, O-glycosidase, and α-(2→3, 6, 8, 9)-neuraminidase, β-N-acetylglucosaminidase and β-(1→4)-galactosidase for 3 h at 37° C. Under native conditions, 35 μg of protein was deglycosylated with the same set of enzymes as above for 3 days at 37° C. The deglycosylated proteins were analyzed by coomassie stained SDS-PAGE and by western blot using standard assay protocols.

N-terminal amino acid sequencing of TNFR2-Fc_VH#4 was carried out as follows. Approximately 2 µg of TNFR2-Fc_VH#4 was run on an SDS-PAGE gel using standard protocols. Proteins were transferred onto the PVDF membrane using the Xcell SureLock™ system (Invitrogen) according to the manufacturer's instructions. The membrane was stained with 0.1% (w/v) amidoblack for approximately 15 min on an orbital shaking platform then washed with dH$_2$O to reduce background staining of the PVDF membrane. The membrane was air-dried prior to N-terminal sequencing. The bands of interest were cut out and sequence determination of the N-terminus of the multispecific binding molecule was performed on an Applied Biosystems 494 HT sequencer (Applied Biosystems, San Francisco, Calif., U.S.A.) with on-line phenylthiohydantoin analysis using an Applied Biosystems 140A micro HPLC.

Characterization Results

Figure 2A:
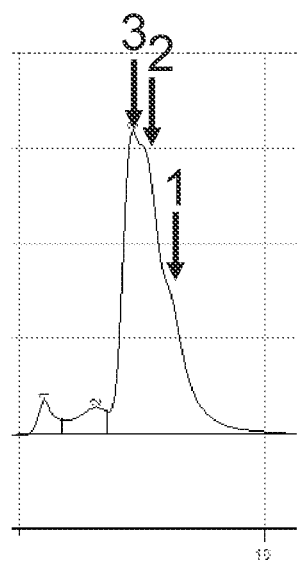
Figure 2B:
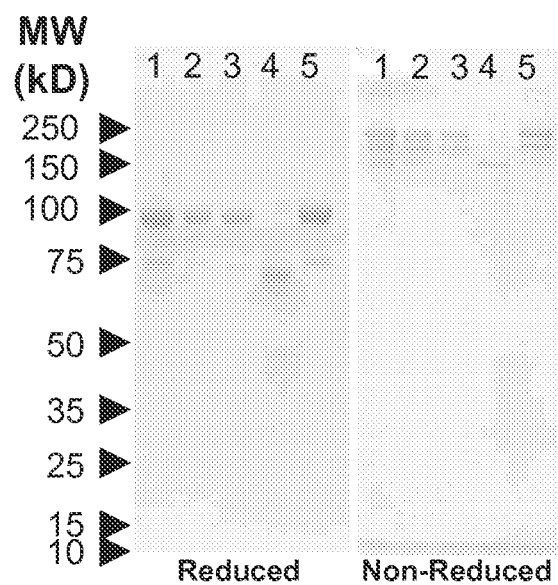

Purified TNFR2-Fc_VH#4 and TNFR2-Fc proteins were profiled by SEC-HPLC for levels of aggregate, monomer and protein fragmentation (FIGS. 2A and 2B). The main peak comprising monomer constituted approximately 90% of the total protein present with the remaining approximately 10% of the protein mass with a lower column retention time indicating the presence of higher order species or aggregates. However, the monomer peak from the SEC-HPLC had two pronounced shoulders indicating that the protein within this peak was not a single species. SDS-PAGE analysis with coomassie staining showed two distinct bands for TNFR2-Fc_VH#4 (at approx. 100 and 75 kD) and similarly two distinct bands for the TNFR2-Fc fusion protein also (at approx. 70 and 45 kD) under reducing conditions (FIG. 2B). Under non-reducing conditions, three major bands were present for TNFR2-Fc_VH#4 (between 150 and 250 kD) and one major band and one minor band for the TNFR2-Fc fusion protein at approx. 150 and 120 kD respectively. Since the molecular mass difference between the two bands under reducing conditions was approximately equivalent to the size of a scFv fragment (~26.5 kD) further analysis was performed in order to understand in what forms the multispecific binding molecule was being generated. Mass spectroscopic analysis under native conditions confirmed the SDS-PAGE data, that for two separate purified protein preparations there were three molecular masses present in the purified TNFR2-Fc_VH#4 preparation at approximately 125, 152 and 176 kD (FIG. 2C).

If the banding pattern observed by SDS-PAGE gel was due to differential glycosylation of TNFR2-Fc_VH#4, then upon deglycosylation this would be resolved back down to a single band. However, the banding pattern was maintained under both reducing and non-reducing conditions when TNFR2-Fc_VH#4 was deglycosylated either as a native protein or as denatured protein (data not shown). Western blot staining of both the glycosylated and deglycosylated TNFR2-Fc_VH#4 with a polyclonal anti-human IgG Fc specific antibody showed that both the full length expected band and the lower molecular mass band were reactive with anti-Fc specific antibodies (data not shown).

Figure 3A:
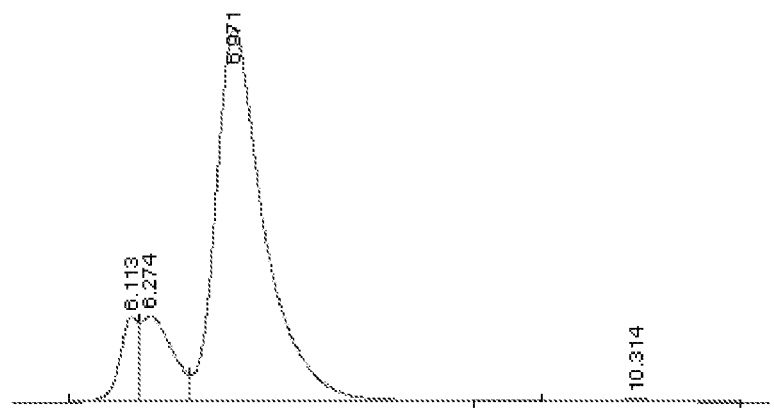
FIG. 3A shows the purity of TNFR2-Fc_VH#4 following Protein A column purification.
Figure 3B:
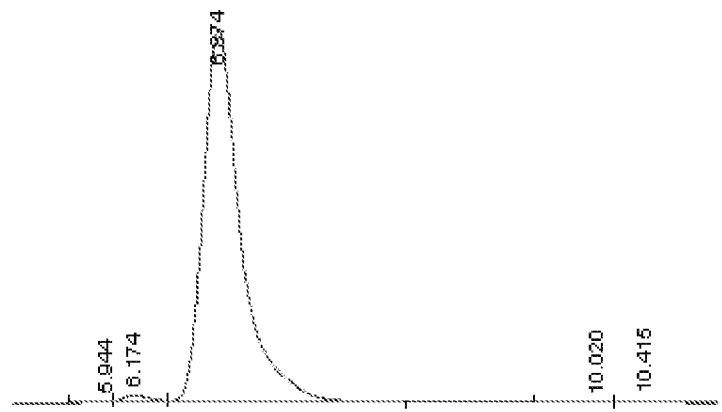
FIG. 3B shows the purity of TNFR2-Fc_VH#4 following a second purification step on an SP sepharose column.

Final identification of the truncated product was made by N-terminal amino acid sequencing of the protein. This revealed that the first 8 amino acids of the N-terminus of the truncated protein to be SMAPGAVH corresponding to amino acids 176 to 183 of the TNFR2-Fc_VH#4 sequence (SEQ ID NO: 14). This represented a 175 amino acid truncation at the N-terminus of TNFR2-Fc_VH#4, which left only 42 amino acids of the TNFR2 domain. This allows us to accurately interpret the mass data from the SDS-PAGE, mass spectroscopy and SEC-HPLC analysis. There were three possible combinations of TNFR2-Fc_VH#4 dimers and all were present in the purified protein preparations: (1) full length homodimer, (2) a heterodimer of full length and truncated species, and (3) a homodimer of truncated species. In order to accurately measure biological activity both in vitro and in vivo, a preparation of the full-length homodimer was generated by a two-step column chromatography process. In the first step, post Protein A purification, the product contained 80.5% monomer (FIG. 3A) and after the second column purification step (SP sepharose) the monomer percentage was 97.8% (FIG. 3B). The yield over the whole process was 7.3%.

Example 2—Thermal Stability Analysis by Differential Scanning Calorimetry (DSC)

An automated MicroCal VP-Capillary DSC (GE Healthcare, USA) was used for the calorimetric measurements. Protein samples were tested at 1 mg/mL in 25 mM Histidine/Histidine-HCl buffer pH 6.0. The protein samples and buffer were subjected to a linear heat ramp from 25° C. to 100° C. at a rate of 95° C. per hour. The buffer was subtracted as a reference from the protein sample using Origin 7 software and the thermal transitions were determined.

Figure 4:
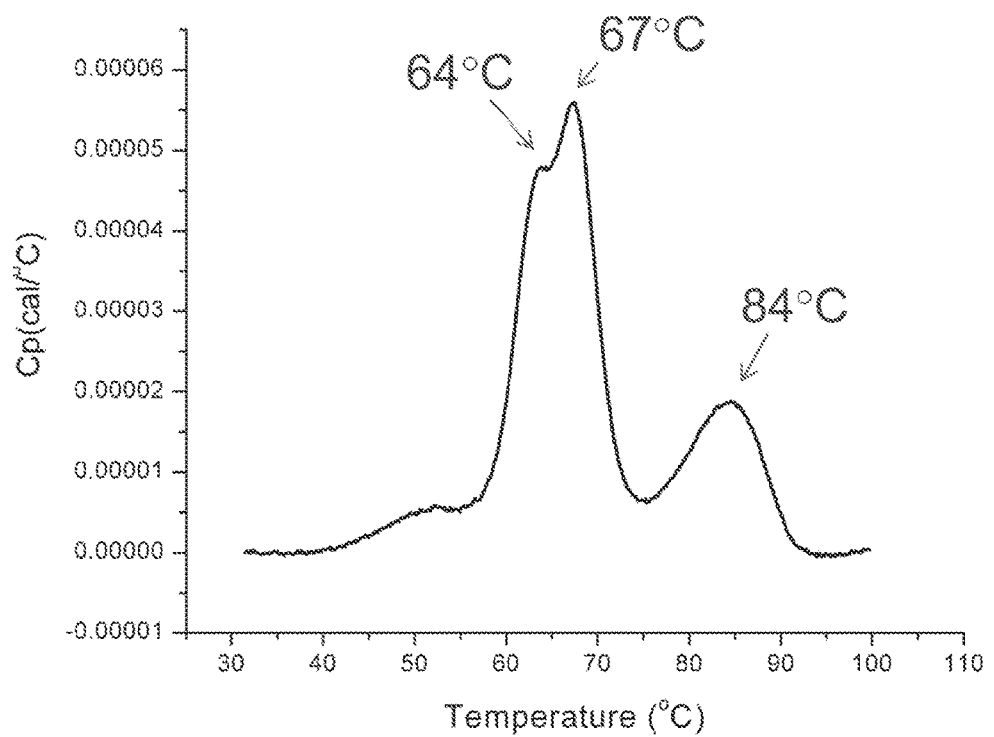
FIG. 4 shows a stability analysis of TNFR2-Fc_VH#4 using differential scanning calorimetry.

The thermogram for TNFR2-Fc_VH#4 (FIG. 4) shows three distinct unfolding transitions with denaturation temperatures (Tm) of 64, 67, and 84° C. We deduced that the Tm of 64° C. corresponded with the denaturation of both the TNFR2 domain and the anti-NGF scFv domain, with the Tms of 67° C. and 84° C. being typical of the denaturation Tms for IgG1 CH2 and CH3 domains respectively (e.g. Dimasi, N., et al., *J Mol Biol*. 393:672-92 (2009), and PCT Publication No. WO 2013/070565). While not wishing to be bound by theory, scFv generally have lower denaturation temperatures than the other antibody domains, and their unfolding is characterized by a single transition event (Roberge et al., 2006, Jung et al., 1999, Tischenko et al., 1998).

Example 3—Confirmation of Antigen Binding to TNFR2-Fc_VH#4

A. Single and Dual Antigen Binding by ELISA

Nunc Maxisorp wells were coated at 4° C. overnight with 50 µl of TNFα (R&D Systems) diluted to 5 µg ml$^{-1}$ in PBS (pH 7.4). The following day the coating solution was removed and the wells blocked with 150 µl of blocking buffer [3% skimmed milk-PBS] for 1 h at room temperature. The wells were rinsed three times in PBS, prior to the addition of 50 µl of a dilution series of TNFR2-Fc_VH#4 made in blocking buffer. After 1 h at room temperature, the wells were washed three times in PBS-Tween 20 (0.1% v/v; PBS-T). Fifty microliters of biotinylated NGF was then added to the wells and incubated for a further hour at room temperature, prior to washing as above and addition of 50 µl of streptavidin-HRP (1:100). After 1 hour at room temperature, the wells were washed with PBS-T, 50 µl of 3,3',5,5'-tetramethylbenzidine substrate added and the color allowed to develop. The reaction was stopped by the addition of 1M H$_2$SO$_4$ and the absorbance at 450 nm was measured using a microtiter plate reader. The resulting data were analyzed using Prism 5 software (GraphPad, San Diego, Calif.). For the single antigen binding ELISA, the wells were coated with either TNFα or NGF-biotin as above and antibody binding detected with anti-Human IgG Fc specific HRP conjugated antibody (1:5000), and color developed as above.

Figure 5A:
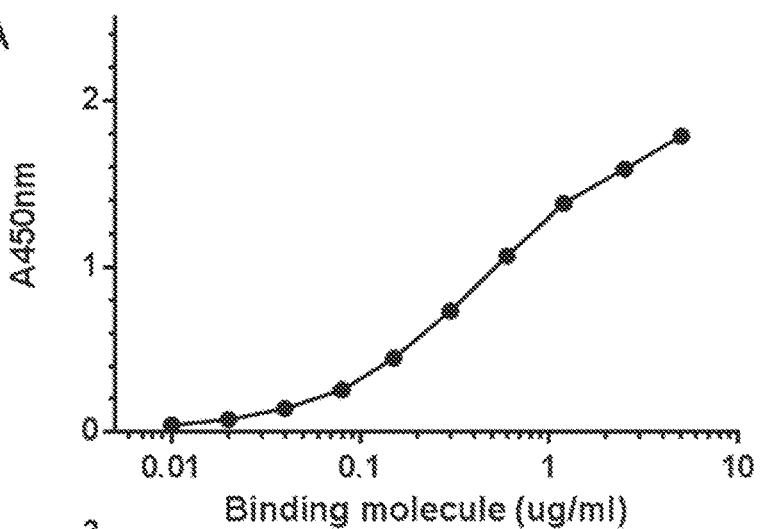
FIGS. 5A-5C show binding of TNFR2-Fc_VH#4 to TNFα and NGF, both singly and together, as determined by ELISA.
Figure 5B:
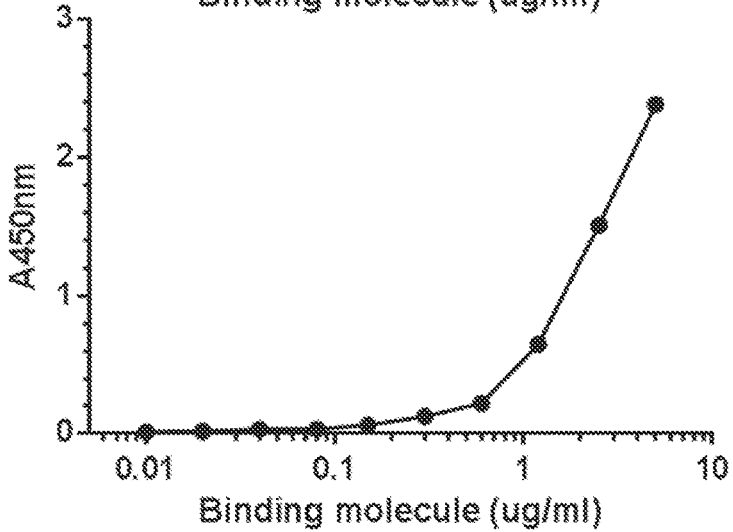
Figure 5C:
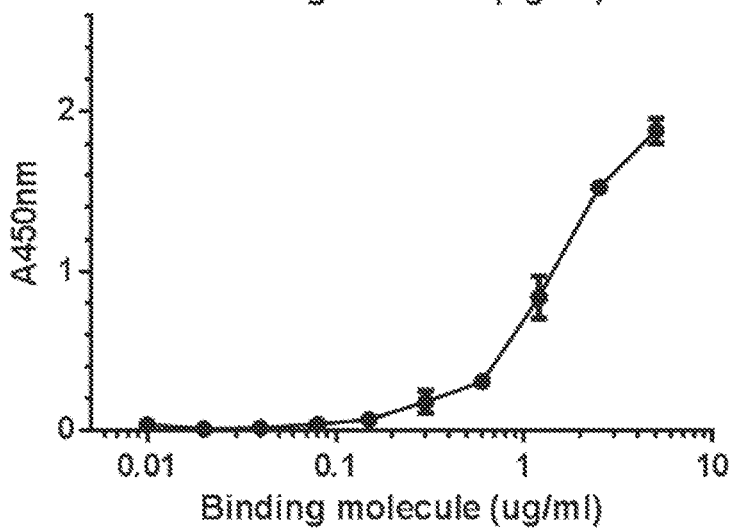

The ELISA results are shown in FIG. 5. TNFR2-Fc_VH#4 was designed to bind to both TNFα and NGF antigens. Single antigen binding was performed by first immobilizing one antigen onto a 96-well microtiter plate, followed by the addition of serial dilutions of TNFR2-Fc_VH#4. Specific binding was detected by using a horseradish peroxidase (HRP)-conjugated anti-IgG Fc specific antibody. For the dual antigen binding ELISA, the first antigen, TNFα was immobilized on the ELISA plate, and then a serial dilution of TNFR2-Fc_VH#4 was added, followed by the addition of the second biotinylated antigen, NGF at a fixed concentration. Specific binding was then detected using an HRP-conjugated streptavidin. TNFR2-Fc_VH#4 bound to TNFα and NGF in the single antigen binding ELISA (FIGS. 5A and B). In the dual antigen binding ELISA, TNFR2-Fc_VH#4 bound to both TNFα and NGF simultaneously (FIG. 5C).

B. Simultaneous Antigen Binding by Surface Plasmon Resonance

Simultaneous antigen binding experiments were carried out essentially as described in Dimasi, N., et al., *J Mol Biol.* 393:672-92 (2009) using a BIAcore 2000 instrument (GE Healthcare). Briefly, a CM5 sensor chip was used to immobilize approximately 1500 resonance units of TNFR2-Fc_VH#4 at 100 nM. The sensor chip surfaces were then used for concurrent binding for TNFα and NGF. The antigens were prepared in HBS-EP buffer [10 mM HEPES (pH 7.4), 150 mM NaCl, 3 mM ethylenediaminetetraacetic acid (EDTA), 0.005% P20]. A flow rate of 30 l/min was used for all binding measurements. For determining the simultaneous binding of the multispecific antibody to TNFα and NGF, 1 μM of TNFα (molecular mass, 17.5 kD) was injected over the sensor chip surface, and upon completion of injection, a mixture of TNFα and NGF (molecular mass, 13.5 kD), both at 1 μM, was then injected. TNFα was included in the mixture with NGF to prevent the signal loss due to TNFα dissociation during NGF binding phase. As a control, a similar binding procedure was performed, and at the last injection only TNFα was added, no further increase in resonance units for this injection indicated that the TNFα was bound at saturating levels. Similar binding and control experiments were performed in which the injection order of TNFα and NGF was reversed.

Simultaneous antigen binding of TNFR2-Fc_VH#4 was characterized by surface plasmon resonance. The binding events were analyzed qualitatively in a sequential manner. TNFR2-Fc_VH#4 was covalently immobilized on to the sensor chip surface using amine coupling chemistry. Subsequently, the first antigen was injected to give saturating levels of binding to TNFR2-Fc_VH#4, then the second antigen was injected as an equimolar admixture with antigen 1. The binding sensorgram clearly showed that TNFR2-Fc_VH#4 bound simultaneously to TNFα and NGF (FIG. 6). Simultaneous binding of the two antigens occurred regardless of the order of antigen injection.

Example 4—Inhibition of TF-1 Cell Proliferation Induced by NGF

Figure 7A:
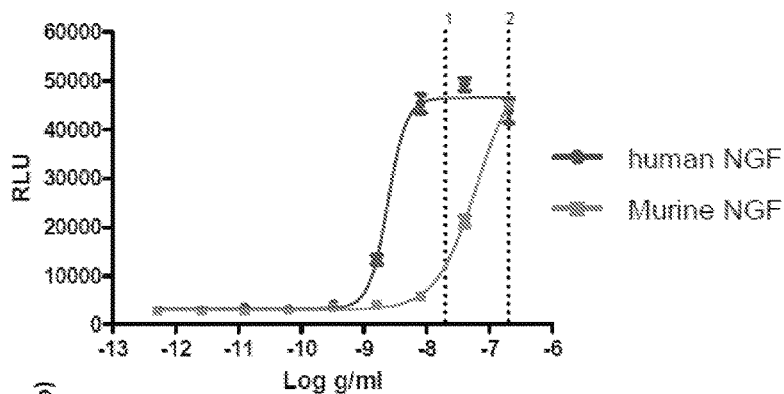

TF-1 cells (ECACC Catalog No. 93022307) were seeded at 1.5×10⁴ cells/well in 50 μl serum free culture media in 96 well tissue culture plate (Corning Costar) and incubated for 18 h at 37° C. with 5% $CO_2$. Recombinant human (Sigma) or mouse NGF (R&D Systems) were pre-incubated with dilutions of TNFR2-Fc_VH#4, MEDI-578 IgG1 TM YTE, a non-binding IgG1 TM YTE isotype control for MEDI-578, or a non-binding bispecific isotype control R347 Bs3Ab for 30 min at 37° C. in 96 well round bottomed plate (Greiner). Fifty microliters of each sample was then added to cell plate and incubated for 48 h at 37° C. Following the incubation period, 100 μl of cell TITRE GLO® assay buffer (Promega) was added and the plate was incubated for 10 min. at 37° C. with 5% $CO_2$. Luminescence was then measured using standard luminescence protocol. Standard NGF-induced TF-1 proliferation in the absence of antibody is shown in FIG. 7A.

Figure 7B:
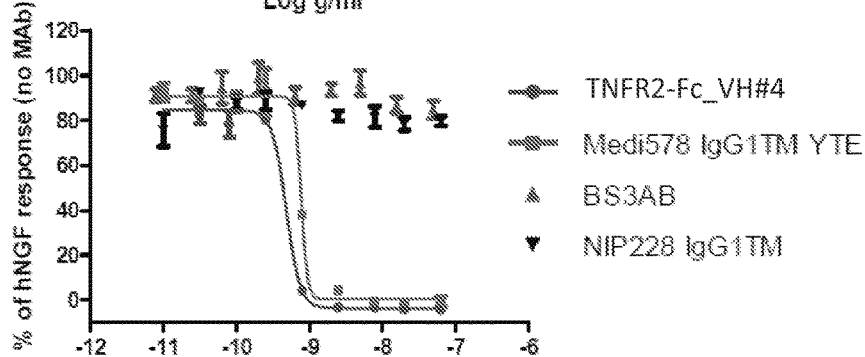

The functional activity of TNFR2-Fc_VH#4 was determined using NGF induced TF-1 proliferation. TNFR2-Fc_VH#4 was able to completely inhibit both human and murine NGF induced proliferation (FIGS. 7B and 7C, respectively). FIG. 7B: TF-1 cells were stimulated with recombinant human NGF corresponding to $EC_{80}$ concentration. Cells were incubated with ligand with a dilution series of antibody for 48 hrs, after which cell proliferation was quantified by culture for 10 mins with cell TITRE GLO® assay buffer (Promega). FIG. 7C: TF-1 cells were stimulated with recombinant murine NGF corresponding to $EC_{80}$ concentration. Cells were incubated with ligand with a dilution series of antibody for 48 hrs., after which cell proliferation was quantified by culture for 10 mins. with cell TITRE GLO® assay buffer (Promega). These data demonstrate that the NGF inhibitory portion of TNFR2-Fc_VH#4 is biologically active and inhibits NGF induced proliferation with a similar potency to MEDI-578 as an IgG1TM. Similar data was also observed for TNFR2-Fc_varB and another TNF-NGF multispecific binding molecule ndimab var B (FIGS. 7D & 7E). ndimab varB comprises a complete anti-TNFα antibody, i.e., an antibody comprising two complete heavy chains and two complete light chains in an $H_2L_2$ format, with MEDI-578 scFv fused to the C-terminus of the heavy chain of the anti-TNFα antibody. The light chain of ndimab varB is depicted in SEQ ID NO: 20 and the heavy chain of ndimab varB is depicted in SEQ ID NO: 22.

Example 5—Inhibition of U937 Cell Apoptosis Induced by TNFα

U937 cells (ECACC Cat. No. 85011440) were plated in a black walled 96 well tissue culture plate (Corning Costar) at a concentration of 8×10⁵ cells/well in 50 μl culture media. U937 cells were stimulated with recombinant human TNFα corresponding to $EC_{80}$ concentration. Cells were incubated with ligand with a dilution series of antibody for 2 hrs, after which caspase 3 activity was quantified by culture for 2 hours with Caspase 3 assay reaction buffer. TNFR2-Fc_VH#4, a non-binding bispecific isotype control, R347 Bs3Ab, and etanercept were pre-incubated with the cells for 30 min at 37° C. This was followed by the addition of 50 μl recombinant human TNFα (R&D Systems) to obtain a final assay concentration of 20 ng/ml and a subsequent 2 h incubation at 37° C. Following the incubation period, 50 μl of Caspase 3 assay reaction buffer (0.2% w/v CHAPS, 0.5% v/v Igepal CA-630, 200 mM NaCl, 50 mM HEPES, 20 μM DEVD-R110 substrate (Invitrogen)) was added and cells incubated for 2.5 h at 37° C. Fluorescence was measured by excitation at 475 nm and emission 512 nm. Caspase activity in the absence of a TNFα antagonist is shown in FIG. 8A.

The functional activity of TNFR2-Fc_VH#4 was determined using a TNFα induced Caspase 3 activity assay in U937 cells. TNFR2-Fc_VH#4 completely inhibited TNFα induced Caspase 3 activity as did etanercept (FIG. 8B). This clearly illustrates that the TNFα inhibitory portion of TNFR2-Fc_VH#4 is biologically active and has a similar potency to etanercept. Similar data was also observed for TNFR2-Fc_varB and ndimab varB (see FIG. 8C).

Example 6—In Vivo Assays

All in vivo procedures were carried out in accordance with the UK Home Office Animals (Scientific Procedures) Act (1986) and approved by a local ethics committee. Female C57Bl/6 mice (Charles River, UK) were used throughout. Mice were housed in groups of 5/6 per cage, in individually ventilated cages (IVC) with free access to food and water under a 12-hour light/dark cycle (lights on 07:00-19:00). Housing and procedure rooms were maintained at 24° C. and constant background noise was maintained by way of a conventional radio station. All mice underwent insertion of transponders under anaesthesia (3% isoflurane in oxygen) for identification purposes at least 5 days before the start of each study.

A. Seltzer Model of Neuropathic Pain

Mechanical hyperalgesia was determined using an analgysemeter (Randall L O, Selitto J J, Arch Int Pharmacodyn Ther. 111:409-19 (1957)) (Ugo Basile). An increasing force was applied to the dorsal surface of each hind paw in turn until a withdrawal response was observed. The application of force was halted at this point and the weight in grams recorded. Data was expressed as withdrawal threshold in grams for ipsilateral and contralateral paws. Following the establishment of baseline readings mice were divided into 2 groups with approximately equal ipsilateral/contralateral ratios and underwent surgery. Mice were anaesthetised with 3% isoflurane. Following this approximately 1 cm of the left sciatic nerve was exposed by blunt dissection through an incision at the level of the mid thigh. A suture (10/0 Virgin Silk: Ethicon) was then passed through the dorsal third of the nerve and tied tightly. The incision was closed using glue and the mice were allowed to recover for at least seven days prior to commencement of testing. Sham operated mice underwent the same protocol but following exposure of the nerve the wound was glued and allowed to recover. Mice were tested for hyperalgesia on day 7 and 10 post surgery. Following testing on day 10, operated mice were further sub-divided into groups which received CAT251 IgG1 isotype control (0.03 mg/kg s.c.), etanercept (0.01 mg/kg s.c.), MEDI-578 (0.03 mg/kg s.c.) or a combination of etanercept (0.01 mg/kg s.c.) and MEDI-578 (0.03 mg/kg s.c.). Sham operated mice all received CAT251 (0.03 mg/kg s.c.). Mechanical hyperalgesia was measured at 4 h, 1, 2, 3, 4 and 7 days post dose.

Co-administration of etanercept and MEDI-578 in a mechanical hyperalgesia model manifested as a significant reduction in the ipsilateral/contralateral ratio on day 10 post surgery when compared to sham operated controls (FIG. 9). Administration of a single dose of either etanercept (0.01 mg/kg s.c.) or MEDI-578 (0.03 mg/kg s.c.) failed to significantly reverse this hyperalgesia. The co-administration of etanercept (0.01 mg/kg s.c.) together with MEDI-578 (0.03 mg/kg s.c.) significantly reversed the mechanical hyperalgesia at 4 h post dose and the effect was maintained through to 7 days post dose.

In a second study the effect of TNFR2-Fc_VH#4 was assessed. Following establishment of a mechanical hyperalgesia, mice were dosed on day 13 post surgery with R347 Bs3Ab isotype control (0.03 mg/kg s.c.), etanercept (0.01 mg/kg s.c.), MEDI-578 (0.03 mg/kg s.c.) or TNFR2-Fc_VH#4 (0.01 mg/kg or 0.03 mg/kg s.c.). Sham prepared animals received R347 Bs3Ab isotype control (0.03 mg/kg s.c.). Mice were tested for mechanical hyperalgesia at 4 h post dose and on days 1, 2, 4 and 7 post dose as described above.

Administration of TNFR2-Fc_VH#4 produced a significant reduction in the ipsilateral/contralateral ratio on day 10 post surgery when compared to sham operated controls (FIG. 10A). The administration of either etanercept (0.01 mg/kg s.c.) or MEDI-578 (0.03 mg/kg s.c.) failed to significantly reverse the mechanical hyperalgesia. However, the administration of TNFR2-Fc_VH#4 (0.01 and 0.03 mg/kg s.c.) produced a significant reversal of the mechanical hyperalgesia at 4 h post dose, an effect which was maintained through to 6 days post dose. No effect was seen following administration of the R347 control Bs3Ab. Similar data was observed when TNFR2-Fc_varB was administered (see FIG. 10B). These data suggest that TNFR2-Fc_VH#4 can significantly reverse pain at very low doses where equivalent doses have been shown to be ineffective or minimally effective with either MEDI-578 or etanercept alone.

B. Chronic Joint Pain Model

Mechanical hypersensitivity was determined using a mouse incapacitance tester (Linton Instrumentation). Mice were placed in the device with their hind paws on separate sensors, and the body weight distribution calculated over a period of 4 s. Data was expressed as the ratio of ipsilateral and contralateral weight bearing in grams.

Following the establishment of baseline readings, mice were divided into 2 groups with approximately equal ipsilateral/contralateral ratios. Intra-articular injections were carried out using the following technique: animals were anesthetised using 3% isoflurane in oxygen and the left knee was shaved and cleaned. The knee joint of each mouse was injected with either 10 μl of Freund's complete adjuvant (FCA) (10 mg/ml) or vehicle (light mineral oil) using a 25-gauge needle mounted on a 100 μl Hamilton syringe. Injections were made directly into the synovial space of the knee joint. Mice were allowed to recover and were re-tested for changes in mechanical hypersensitivity on days 7 and 10 post injection as described above. Following testing on day 10, FCA treated mice were further randomised into groups and on day 13 mice were dosed with etanercept (0.01 mg/kg i.p.) or vehicle after which they received a dose of MEDI-578 (0.03 mg/kg i.v.) or CAT251 isotype control (0.03 mg/kg i.v.). Mice were tested for mechanical hypersensitivity at 4 h post dose and on days 1, 2, 4 and 7 post dose as described above.

The effect of co-administration of etanercept and MEDI-578 was assessed using the intra-articular FCA model of inflammatory pain. Intra-articular administration of FCA caused a mechanical hypersensitivity that manifested as a significant reduction in the ipsilateral/contralateral ratio on days 7 and 10 when compared to vehicle control (FIG. 11). No reduction in the ipsilateral/contralateral ratio was observed in the sham treated groups compared to pre-treatment baseline levels. The administration of etanercept (0.01 mg/kg i.p.)+CAT251 (0.03 mg/kg i.v.) or PBS (10 ml/kg i.p.)+MEDI-578 (0.03 mg/kg i.v.) caused a slight reversal of the FCA induced mechanical hypersensitivity at 4 h and days 1, 2, 4 and 7 post dose but this failed to reach statistical significance. However, the administration of etanercept (0.01 mg/kg i.p.)+MEDI-578 (0.03 mg/kg i.v.) caused a significant reversal of the FCA induced mechanical hypersensitivity at all times of testing post dose.

In a second study, the effect of TNFR2-Fc_VH#4 was assessed. Following establishment of FCA induced mechanical hypersensitivity, mice were dosed on day 13 post-FCA with: R347 Bs3Ab isotype control (0.01 mg/kg s.c.), etanercept (0.01 mg/kg s.c.), MEDI-578 (0.01 mg/kg s.c.) or TNFR2-Fc_VH#4 (0.003 mg/kg or 0.01 mg/kg s.c.). Again mice were tested for mechanical hypersensitivity at 4 h post dose and on days 1, 2, 4 and 7 post dose as described above.

The effect of TNFR2-Fc_VH#4 ("bispecific") as compared to the effects of etanercept and MEDI-578 individually is shown in FIG. 12. Neither etanercept (0.01 mg/kg s.c.) nor MEDI-578 (0.01 mg/kg s.c.) significantly reversed the FCA induced mechanical hypersensitivity at any time point post dose. However, administration of TNFR2-Fc_VH#4 caused a significant reversal of FCA induced mechanical hypersensitivity. The higher dose of TNFR2-Fc_VH#4 (0.01 mg/kg s.c) showed significant activity for the duration of the study whereas the lower dose (0.003 mg/kg s.c.) reached significance on day 1 post dose and remained at a similar level to the higher dose for the duration of the study.

C. Established FCA Induced Model of Mechanical Hypersensitivity in the Rat

Intraplantar injection of Freunds Complete adjuvant (FCA) causes an inflammatory reaction, which induces hypersensitivity and edema, and mimics some aspects of clinical inflammatory pain. These effects can be investigated using equipment to measure weight bearing. Assessment of potential anti-hyperalgesic properties of TNFR2-Fc_VH#4 FCA induced hypersensitivity using weight bearing method. Naive rats distribute their body weight equally between the two hind paws. However, when the injected (left) hind paw is inflamed and/or painful, the weight is re-distributed so that less weight is put on the affected paw (decrease in weight bearing on injured paw). Weight bearing through each hind limb is measured using a rat incapacitance tester (Linton Instruments, UK). Rats are placed in the incapacitance tester with the hind paws on separate sensors and the average force exerted by both hind limbs are recorded over 4 seconds.

For this study, naïve rats (Male, Sprague Dawley Rats (Harlan, UK), 198-258 g) were acclimatised to the procedure room in their home cages, with food and water available ad libitum. Habituation to the incapacitance tester was performed over several days. Baseline weight bearing recordings were taken prior to induction of insult. Inflammatory hypersensitivity was induced by intraplantar injection of FCA (available from Sigma, 100 µl of 1 mg/ml solution) into the left hind paw. A pre-treatment weight bearing measurement was taken to assess hypersensitivity 23 hours post-FCA.

Animals were then ranked and randomised to treatment groups according to the weight bearing FCA window in a Latin square design. At 24 hours post FCA injection, animals were treated with either TNFR2-Fc_VH#4 ("bispecific") given i.v. at 0.003, 0.01, 0.03, 0.3, & 3 mg/kg, a negative control antibody, NIP228 (an antibody raised to bind to hapten nitrophenol) given i.v. at 3 mg/kg, vehicle (1% Methylcellulose) given p.o. 2 ml/kg, or indomethacin given 10 mg/kg p.o.

Weight bearing was assessed 4 and 24 hours post antibody/drug treatment. Data were analyzed by comparing treatment groups to the vehicle control group at each time point. Statistical analysis included repeated measures ANOVA followed by Planned comparison test using InVivoStat (invivostat.co.uk), ($p<0.05$ considered significant). The results are shown in FIG. 13. A significant reversal of the hypersensitivity was observed with Indomethacin (10 mg/kg) at 4 and 24 hours. TNFR2-Fc_VH#4 dosed at 0.3 and 3 mg/kg showed significant reversal of the hypersensitivity at both 4 and 24 hours, TNFR2-Fc_VH#4 dosed at 0.003 and 0.03 mg/kg also showed a significant reversal of the hypersensitivity, but only at 24 hours. The isotype control, NIP228 had no significant effect on the FCA response at any time point.

Example 7—p38 Phosphorylation by TNFα and NGF

Literature suggests that p38 phosphorylation plays an important role in the development of neuropathic pain. For example, treatment with p38 inhibitors have been shown to prevent the development of neuropathic pain symptoms in the spared nerve injury model (Wen Y R et al., Anesthesiology 2007, 107:312-321) and in a sciatic inflammatory neuropathy model (Milligan E D et al., J Neurosci 2003, 23:1026-1040). In the present experiment, the role of TNFα, NGF, and the combination TNFα and NGF on p38 phorphorylation was investigated in a cell culture assay. Briefly, Neuroscreen-1 cells (a subclone of PC-12 rat neuroendocrine cells) were incubated with increasing amounts of TNFα, NGF, or a combination of TNFα and NGF. Following a 20 minute incubation period, phospho-p38 was quantified using a homogeneous time resolved fluorescence (HTRF) assay (Cisbio).

HTRF Assay:

Following stimulation with TNFα, NGF, or a combination of TNFα and NGF, cell supernatants were rapidly removed and cells lysed in lysis buffer. Phospho-p38 MAPK (Thr180/Tyr182) was detected in lysates in a sandwich assay format using two different specific antibodies; an anti-phospho-p38 antibody conjugated to europium cryptate (donor fluorophore) and an anti-p38 (total) antibody conjugated to d2 (acceptor fluorophore). Antibodies were incubated with cell lysates and HTRF ratios calculated from fluorescence measurements at 665 nm and 620 nm made using an EnVision Multilabel Plate Reader (Perkin Elmer).

Data are presented as HTRF ratios, which are calculated as the ratio between the emission at 665 nm and the emission at 620 nm. A heat map showing HTRF ratios from phospho-p38 reactions is shown in FIG. 14. Dose response curves showing the effect of TNFα, NGF, or a combination of TNFα and NGF are shown in FIG. 15. As can be seen from FIG. 15, the combined effect of higher concentrations of TNFα and NGF on phospho-p38 is greater than the predicted sum of the phospho-p38 signal induced by either factor alone. These data suggest that TNFα and NGF may act together to induce p38 phosphorylation, and that the two pathways may be implicated in molecular signaling leading to pain.

Example 8—ERK Phosphorylation by TNFα and NGF

Like p38, ERK is also activated during neuropathic pain development (Zhuang Z Y et al., Pain 2005, 114:149-159). In the present experiment, the role of TNFα, NGF, and the combination TNFα and NGF on ERK phorphorylation was investigated in a cell culture assay. Briefly, Neuroscreen-1 cells (a subclone of PC-12 rat neuroendocrine cells) were incubated with increasing amounts of TNFα, NGF, or a combination of TNFα and NGF. Following a 20 minute incubation period, phospho-ERK was quantified using a HTRF assay (Cisbio).

HTRF Assay:

Following stimulation, cell supernatants were rapidly removed and cells lysed in lysis buffer. Phospho-ERK MAPK (Thr202/Tyr204) was detected in lysates in a sandwich assay format using two different specific antibodies; an anti-phospho-ERK antibody conjugated to europium cryptate (donor fluorophore) and an anti-ERK (total) antibody conjugated to d2 (acceptor fluorophore). Antibodies were incubated with cell lysates and HTRF ratios calculated from fluorescence measurements at 665 nm and 620 nm made using an EnVision Multilabel Plate Reader (Perkin Elmer).

Data are presented as HTRF ratios, which are calculated as the ratio between the emission at 665 nm and the emission at 620 nm. A heat map showing HTRF ratios from phospho-ERK reactions is shown in FIG. 16. Dose response curves showing the effect of TNFα, NGF, or a combination of TNFα and NGF are shown in FIG. 17. As can be seen from FIG. 17, low amounts of TNFα alone did not induce phospho-ERK, but higher amounts, enhanced NGF-induced phospho-ERK. These data suggest that TNFα and NGF may act together to induce p38 phosphorylation, and that the two pathways may be implicated in molecular signaling leading to pain.

```
                        Sequence listing

SEQ ID NO: 1 NP_002497.2| beta-nerve growth factor precursor [Homo sapiens]
    1 MSMLFYTLIT AFLIGIQAEP HSESNVPAGH TIPQAHWTKL QHSLDTALRR ARSAPAAAIA
   61 ARVAGQTRNI TVDPRLFKKR RLRSPRVLFS TQPPREAADT QDLDFEVGGA APFNRTHRSK
  121 RSSSHPIFHR GEFSVCDSVS VWVGDKTTAT DIKGKEVMVL GEVNINNSVF KQYFFETKCR
  181 DPNPVDSGCR GIDSKHWNSY CTTTHTFVKA LTMDGKQAAW RFIRIDTACV CVLSRKAVRR
  241 A SEQ ID NO: 2 NP_000585.2| tumor necrosis factor [Homo sapiens]
    1 MSTESMIRDV ELAEEALPKK TGGPQGSRRC LFLSLFSFLI VAGATTLFCL LHFGVIGPQR
   61 EEFPRDLSLI SPLAQAVRSS SRTPSDKPVA HVVANPQAEG QLQWLNRRAN ALLANGVELR
  121 DNQLVVPSEG LYLIYSQVLF KGQGCPSTHV LLTHTISRIA VSYQTKVNLL SAIKSPCQRE
  181 TPEGAEAKPW YEPIYLGGVF QLEKGDRLSA EINRPDYLDF AESGQVYFGI IAL SEQ ID NO: 3 MEDI-578 VH (1256A5 VH)
    1 QVQLVQSGAE VKKPGSSVKV SCKASGGTFS TYGISWVRQA PGQGLEWMGG IIPIFDTGNS
   61 AQSFQGRVTI TADESTSTAY MELSSLRSED TAVYYCARSS RIYDLNPSLT AYYDMDVWGQ
  121 GTMVTVSS

SEQ ID NO: 4 MEDI-578 VHCDR1
    1 TYGIS

SEQ ID NO: 5 MEDI-578 VHCDR2
    1 GIIPIFDTGN SAQSFQG

SEQ ID NO: 6 MEDI-578 VHCDR3
    1 SSRIYDLNPS LTAYYDMDV

SEQ ID NO: 7 MEDI-578 VL (1256A5 VL)
    1 QSVLTQPPSV SAAPGQKVTI SCSGSSSNIG NNYVSWYQQL PGTAPKLLIY DNNKRPSGIP
   61 DRFSGSKSGT SATLGITGLQ TGDEADYYCG TWDSSLSAWV FGGGTKLTVL

SEQ ID NO: 8 MEDI-578 VLCDR1
    1 SGSSSNIGNN YVS

SEQ ID NO: 9 MEDI-578 VLCDR2
    1 DNNKRPS

SEQ ID NO: 10 MEDI-578 VLCDR3
    1 GTWDSSLSAW V

SEQ ID NO: 11
    1 SSRIYDFNSA LISYYDMDV

SEQ ID NO: 12
    1 SSRIYDMISS LQPYYDMDV

SEQ ID NO: 13 soluble TNFR2 amino acid sequence
    1 LPAQVAFTPY APEPGSTCRL REYYDQTAQM CCSKCSPGQH AKVFCTKTSD TVCDSCEDST
   61 YTQLWNWVPE CLSCGSRCSS DQVETQACTR EQNRICTCRP GWYCALSKQE GCRLCAPLRK
  121 CRPGFGVARP GTETSDVVCK PCAPGTFSNT TSSTDICRPH QICNVVAIPG NASMDAVCTS
  181 TSPTRSMAPG AVHLPQPVST RSQHTQPTPE PSTAPSTSFL LPMGPSPPAE GSTGDEPKSC
  241 DKTHTCPPCP APELLGGPSV FLFPPKPKDT LMISRTPEVT CVVVDVSHED PEVKFNWYVD
  301 GVEVHNAKTK PREEQYNSTY RVVSVLTVLH QDWLNGKEYK CKVSNKALPA PIEKTISKAK
  361 GQPREPQVYT LPPSREEMTK NQVSLTCLVK GFYPSDIAVE WESNGQPENN YKTTPPVLDS
  421 DGSFFLYSKL TVDKSRWQQG NVFSCSVMHE ALHNHYTQKS LSLSPGK SEQ ID NO: 14 TNFR2-Fc_VH#4 - amino acid sequence
    1 LPAQVAFTPY APEPGSTCRL REYYDQTAQM CCSKCSPGQH AKVFCTKTSD TVCDSCEDST
   61 YTQLWNWVPE CLSCGSRCSS DQVETQACTR EQNRICTCRP GWYCALSKQE GCRLCAPLRK
  121 CRPGFGVARP GTETSDVVCK PCAPGTFSNT TSSTDICRPH QICNVVAIPG NASMDAVCTS
  181 TSPTRSMAPG AVHLPQPVST RSQHTQPTPE PSTAPSTSFL LPMGPSPPAE GSTGDEPKSC
  241 DKTHTCPPCP APELLGGPSV FLFPPKPKDT LMISRTPEVT CVVVDVSHED PEVKFNWYVD
  301 GVEVHNAKTK PREEQYNSTY RVVSVLTVLH QDWLNGKEYK CKVSNKALPA PIEKTISKAK
  361 GQPREPQVYT LPPSREEMTK NQVSLTCLVK GFYPSDIAVE WESNGQPENN YKTTPPVLDS
  421 DGSFFLYSKL TVDKSRWQQG NVFSCSVMHE ALHNHYTQKS LSLSPGKGGG GSGGGGSQVQ
```

-continued

```
Sequence listing
```

```
481 LVQSGAEVKK PGSSVKVSCK ASGGTFSTYG ISWVRQAPGQ GLEWMGGIIP IFDTGNSAQS
541 FQGRVTITAD ESTSTAYMEL SSLRSEDTAV YYCARSSRIY DLNPSLTAYY DMDVWGQGTM
601 VTVSSGGGGS GGGGSGGGGS AQSVLTQPPS VSAAPGQKVT ISCSGSSSNI GNNYVSWYQQ
661 LPGTAPKLLI YDNNKRPSGI PDRFSGSKSG TSATLGITGL QTGDEADYYC GTWDSSLSAW
721 VFGGGTKLTV L

SEQ ID NO: 15 (Gly₄Ser)₃ 15 aa linker sequence
  1 GGGGSGGGGS GGGGS

SEQ ID NO: 16 TNFR2-Fc_VH#4 - nucleotide sequence
   1 CTGCCCGCCC AGGTGGCCTT TACCCCTTAT GCCCCCGAGC CCGGCAGCAC CTGTCGGCTG
  61 AGAGAGTACT ACGACCAGAC CGCCCAGATG TGCTGCAGCA AGTGCTCTCC TGGCCAGCAT
 121 GCCAAGGTGT TCTGCACCAA GACCAGCGAC ACCGTGTGCG ACAGCTGCGA GGACAGCACC
 181 TACACCCAGC TGTGGAACTG GGTGCCCGAG TGCCTGAGCT GCGGCAGCAG ATGCAGCAGC
 241 GACCAGGTGG AAACCCAGGC CTGCACCAGA GAGCAGAACC GGATCTGCAC CTGTAGACCC
 301 GGCTGGTACT GCGCCCTGAG CAAGCAGGAA GGCTGCAGAC TCTGCGCCCC TCTGCGGAAG
 361 TGCAGACCCG GCTTTGGCGT GGCCAGACCC GGCACCGAGA CAAGCGACGT GGTCTGTAAG
 421 CCCTGCGCTC CTGGCACCTT CAGCAACACC ACCAGCAGCA CCGACATCTG CAGACCCCAC
 481 CAGATCTGCA ACGTGGTGGC CATCCCCGGC AACGCCAGCA TGGATGCCGT CTGCACCAGC
 541 ACTAGCCCCA CCAGAAGTAT GGCCCCTGGC GCCGTGCATC TGCCCCAGCC TGTGTCCACC
 601 AGAAGCCAGC ACACCCAGCC CACCCCTGAG CCTAGCACCG CCCCCTCCAC CAGCTTTCTG
 661 CTGCCTATGG GCCCTAGCCC TCCAGCCGAG GGAAGCACAG GCGACGAGCC AAGAGCTGC
 721 GACAAGACCC ACACCTGTCC CCCTGCCCT GCCCCTGAAC TGCTGGGCGG ACCCAGCGTG
 781 TTCCTGTTCC CCCCAAAGCC CAAGGACACC CTGATGATCA GCCGGACCCC CGAAGTGACC
 841 TGCGTGGTGG TGGACGTGTC CCACGAGGAC CCTGAAGTGA AGTTCAATTG GTACGTGGAC
 901 GGCGTGGAAG TGCACAACGC CAAGACCAAG CCCAGAGAGG AACAGTACAA CTCCACCTAC
 961 CGGGTGGTGT CCGTGCTGAC CGTGCTGCAC CAGGACTGGC TGAACGGCAA AGAGTACAAG
1021 TGCAAGGTCT CCAACAAGGC CCTGCCTGCC CCCATCGAGA AAACCATCAG CAAGGCCAAG
1081 GGCCAGCCCC GCGAGCCTCA GGTGTACACA CTGCCCCCCA GCCGGGAAGA GATGACCAAG
1141 AACCAGGTGT CCCTGACCTG CCTGGTCAAA GGCTTCTACC CCAGCGATAT CGCCGTGGAA
1201 TGGGAGAGCA ATGGCCAGCC CGAGAACAAC TACAAGACCA CCCCCCCTGT GCTGGACAGC
1261 GACGGCTCAT TCTTCCTGTA CAGCAAGCTG ACCGTGGACA AGTCCCGGTG GCAGCAGGGC
1321 AACGTGTTCA GCTGCAGCGT GATGCACGAG GCCCTGCACA ACCACTACAC CCAGAAGTCC
1381 CTGAGCCTGA GCCCCGGAAA GGGCGGTGGC GGATCCGGAG GTGGGGGATC TCAGGTGCAG
1441 CTGGTGCAGT CTGGCGCCGA AGTGAAGAAA CCCGGCTCTA GCGTGAAGGT GTCCTGCAAG
1501 GCCAGCGGCG GCACCTTCTC CACCTACGGC ATCAGCTGGG TCCGCCAGGC CCCTGGACAG
1561 GGCCTGGAAT GGATGGGCGG CATCATCCCC ATCTTCGACA CCGGCAACAG CGCCCAGAGC
1621 TTCCAGGGCA GAGTGACCAT CACCGCCGAC GAGAGCACCT CCACCGCCTA CATGGAACTG
1681 AGCAGCCTGC GGAGCGAGGA CACCGCCGTG TACTACTGCG CCAGAAGCAG CCGGATCTAC
1741 GACCTGAACC CCAGCCTGAC CGCCTACTAC GACATGGACG TGTGGGGCCA GGGCACCATG
1801 GTCACAGTGT CTAGCGGAGG CGGCGGATCT GGCGGCGGAG GAAGTGGCGG GGGAGGATCT
1861 GCCCAGAGCG TGCTGACCCA GCCCCCTTCT GTGTCTGCCG CCCCTGGCCA GAAAGTGACC
1921 ATCTCCTGCA GCGGCAGCAG CAGCAACATC GGCAACAACT ACGTGTCCTG GTATCAGCAG
1981 CTGCCCGGCA CCGCCCCTAA GCTGCTGATC TACGACAACA ACAAGCGGCC CAGCGGCATC
2041 CCCGACCGGT TTAGCGGCAG CAAGAGCGGG ACTTCTGCTA CACTGGGCAT CACAGGCCTG
2101 CAGACCGGCG ACGAGGCCGA CTACTACTGC GGCACCTGGG ACAGCAGCCT GAGCGCTTGG
2161 GTGTTCGGCG GAGGCACCAA GCTGACAGTG CTG SEQ ID NO: 17 - TNFR2-Fc_varB - amino acid sequence
  1 LPAQVAFTPY APEPGSTCRL REYYDQTAQM CCSKCSPGQH AKVFCTKTSD TVCDSCEDST
 61 YTQLWNWVPE CLSCGSRCSS DQVETQACTR EQNRICTCRP GWYCALSKQE GCRLCAPLRK
121 CRPGFGVARP GTETSDVVCK PCAPGTFSNT TSSTDICRPH QICNVVAIPG NASMDAVCTS
181 TSPTRSMAPG AVHLPQPVST RSQHTQPTPE PSTAPSTSFL LPMGPSPPAE GSTGDEPKSC
241 DKTHTCPPCP APELLGGPSV FLFPPKPKDT LMISRTPEVT CVVVDVSHED PEVKFNWYVD
301 GVEVHNAKTK PREEQYNSTY RVVSVLTVLH QDWLNGKEYK CKVSNKALPA PIEKTISKAK
361 GQPREPQVYT LPPSREEMTK NQVSLTCLVK GFYPSDIAVE WESNGQPENN YKTTPPVLDS
421 DGSFFLYSKL TVDKSRWQQG NVFSCSVMHE ALHNHYTQKS LSLSPGKGGG GSGGGGSQVQ
481 LVQSGAEVKK PGSSVKVSCK ASGGTFSTYG ISWVRQAPGQ GLEWMGGIIP IFDTGNSAQS
541 FQGRVTITAD ESTSTAYMEL SSLRSEDTAV YYCARSSRIY DLNPSLTAYY DMDVWGQGTM
601 VTVSSGGGGS GGGGSGGGGS GGGGSQSVLT QPPSVSAAPG QKVTISCSGS SSNIGNNYVS
661 WYQQLPGTAP KLLIYDNNKR PSGIPDRFSG SKSGTSATLG ITGLQTGDEA DYYCGTWDSS
721 LSAWVFGCGT KLTVL SEQ ID NO: 18 - TNFR2-Fc_varB - nucleotide sequence
   1 CTGCCCGCCC AGGTGGCCTT TACCCCTTAT GCCCCCGAGC CCGGCAGCAC CTGTCGGCTG
  61 AGAGAGTACT ACGACCAGAC CGCCCAGATG TGCTGCAGCA AGTGCTCTCC TGGCCAGCAT
 121 GCCAAGGTGT TCTGCACCAA GACCAGCGAC ACCGTGTGCG ACAGCTGCGA GGACAGCACC
 181 TACACCCAGC TGTGGAACTG GGTGCCCGAG TGCCTGAGCT GCGGCAGCAG ATGCAGCAGC
 241 GACCAGGTGG AAACCCAGGC CTGCACCAGA GAGCAGAACC GGATCTGCAC CTGTAGACCC
 301 GGCTGGTACT GCGCCCTGAG CAAGCAGGAA GGCTGCAGAC TCTGCGCCCC TCTGCGGAAG
 361 TGCAGACCCG GCTTTGGCGT GGCCAGACCC GGCACCGAGA CAAGCGACGT GGTCTGCAAG
 421 CCCTGCGCTC CTGGCACCTT CAGCAACACC ACCAGCAGCA CCGACATCTG CAGACCCCAC
 481 CAGATCTGCA ACGTGGTGGC CATCCCCGGC AACGCCAGCA TGGATGCCGT GTGCACCAGC
 541 ACCAGCCCCA CCAGAAGTAT GGCCCCTGGC GCCGTGCATC TGCCCCAGCC TGTGTCCACC
 601 AGAAGCCAGC ACACCCAGCC CACCCCTGAG CCTAGCACCG CCCCCTCCAC CAGCTTTCTG
 661 CTGCCTATGG GCCCTAGCCC TCCAGCCGAG GGAAGCACAG GCGACGAGCC AAGAGCTGC
 721 GACAAGACCC ACACCTGTCC CCCTGCCCCT GCCCCTGAAC TGCTGGGCGG ACCCAGCGTG
```

| Sequence listing |
|---|
| 781 TTCCTGTTCC CCCCAAAGCC CAAGGACACC CTGATGATCA GCCGGACCCC CGAAGTGACC
841 TGCGTGGTGG TGGACGTGTC CCACGAGGAC CCTGAAGTGA AGTTCAATTG GTACGTGGAC
901 GGCGTGGAAG TGCACAACGC CAAGACCAAG CCCAGAGAGG AACAGTACAA CTCCACCTAC
961 CGGGTGGTGT CCGTGCTGAC CGTGCTGCAC CAGGACTGGC TGAACGGCAA AGAGTACAAG
1021 TGCAAAGTCT CCAACAAGGC CCTGCCTGCC CCCATCGAGA AAACCATCAG CAAGGCCAAG
1081 GGCCAGCCCC GCGAGCCTCA gGTGTACACA CTGCCCCCCA GCCGGGAAGA GATGACCAAG
1141 AACCAGGTGT CCCTGACCTG CCTGGTCAAA GGCTTCTACC CCAGCGATAT CGCCGTGGAA
1201 TGGGAGAGCA ACGGCCAGCC CGAGAACAAC TACAAGACCA CCCCCCCTGT GCTGGACAGC
1261 GACGGCTCAT TCTTCCTGTA CAGCAAGCTG ACCGTGGACA AGAGCCGGTG GCAGCAGGGC
1321 AATGTCTTCA GCTGTAGCGT GATGCACGAG GCCCTGCACA ACCACTACAC CCAGAAGTCC
1381 CTGAGCCTGA GCCCCGGAAA GGGCGGAGGC GGATCCGGAG GTGGGGGATC TCAGGTGCAG
1441 CTGGTGCAGT CTGGCGCCGA AGTGAAGAAA CCCGGCTCTA GCGTGAAGGT GTCCTGCAAG
1501 GCCAGCGGCG GCACCTTCTC CACCTACGGC ATCAGCTGGG TCCGCCAGGC CCCTGGACAG
1561 TGTCTGGAAT GGATGGGCGG CATCATCCCC ATCTTCGACA CCGGCAACAG CGCCCAGAGC
1621 TTCCAGGGCA GAGTGACCAT CACCGCCGAC GAGAGCACCT CCACCGCCTA CATGGAACTG
1681 AGCAGCCTGC GGAGCGAGGA CACCGCCGTG TACTACTGCG CCAGAAGCAG CCGGATCTAC
1741 GACCTGAACC CCAGCCTGAC CGCCTACTAC GACATGGACG TGTGGGGCCA GGGCACCATG
1801 GTCACAGTGT CTAGCGGAGG CGGAGGCAGC GGAGGTGGTG GATCTGGTGG CGGAGGAAGT
1861 GGCGGCGGAG GCTCTCAGAG CGTGCTGACC CAGCCCCCTT CTGTGTCTGC CGCCCCTGGC
1921 CAGAAAGTGA CCATCTCCTG CAGCGGCAGC AGCAACATCG GCAACAACTA CGTGTCCTGG
1981 TGGTATCAGC AGCTGCCCGG CACCGCCCCT AAGCTGCTGA TCTACGACAA CAACAAGCGG
2041 CCCAGCGGCA TCCCCGACCG GTTTAGCGGC AGCAAGAGCG GGACTTCTGC TACACTGGGC
2101 ATCACAGGCC TGCAGACCGG CGACGAGGCC GACTACTACT GCGGCACCTG GACAGCAGC
2161 CTGAGCGCTT GGGTGTTCGG CTGCGGCACC AAGCTGACAG TGCTG |

SEQ ID NO: 19 - (Gly₄Ser)₄ 20 aa linker sequence
    1 GGGGSGGGGS GGGGSGGGGS

SEQ ID NO: 20 - ndimab varB - L chain amino acid sequence
    1 EIVLTQSPAT LSLSPGERAT LSCRASQSVY SYLAWYQQKP GQAPRLLIYD ASNRAIGIPA
   61 RFSGSGSGTD FTLTISSLEP EDFAVYYCQQ RSNWPPFTFG PGTKVDIKRT VAAPSVFIFP
  121 PSDEQLKSGT ASVVCLLNNF YPREAKVQWK VDNALQSGNS QESVTEQDSK DSTYSLSSTL
  181 TLSKADYEKH KVYACEVTHQ GLSSPVTKSF NRGEC SEQ ID NO: 21 - ndimab varB - L chain nucleotide sequence
    1 GAAATCGTGC TGACCCAGAG CCCCGCCACC CTGTCTCTGA GCCCTGGCGA GAGAGCCACC
   61 CTGAGCTGCA GAGCCAGCCA GAGCGTGTAC TCCTACCTGG CTTGGTATCA GCAGAAGCCC
  121 GGCCAGGCCC CCAGACTGCT GATCTACGAC GCCAGCAACA GGGCCATCGG CATCCCTGCC
  181 AGATTTTCTG GCAGCGGCAG CGGCACCGAC TTCACCCTGA CCATCAGCAG CCTGGAACCC
  241 GAGGACTTCG CCGTGTACTA CTGCCAGCAG CGGAGCAACT GGCCCCCCTT CACCTTCGGC
  301 CCTGGCACCA AGGTGGACAT CAAGCGTACG GTGGCTGCAC CATCTGTCTT CATCTTCCCG
  361 CCATCTGATG AGCAGTTGAA ATCTGGAACT GCCTCTGTTG TGTGCCTGCT GAATAACTTC
  421 TATCCCAGAG AGGCCAAAGT ACAGTGGAAG GTGGATAACG CCCTCCAATC GGGTAACTCC
  481 CAGGAGAGTG TCACAGAGCA GGACAGCAAG GACAGCACCT ACAGCCTCAG CAGCACCCTG
  541 ACGCTGAGCA AAGCAGACTA CGAGAAACAC AAAGTCTACG CCTGCGAAGT CACCCATCAG
  601 GGCCTGAGCT CGCCCGTCAC AAAGAGCTTC AACAGGGGAG AGTGT SEQ ID NO: 22 - ndimab varB - H chain amino acid sequence
    1 QVQLVESGGG VVQPGRSLRL SCAASGFIFS SYAMHWVRQA PGNGLEWVAF MSYDGSNKKY
   61 ADSVKGRFTI SRDNSKNTLY LQMNSLRAED TAVYYCARDR GISAGGNYYY YGMDVWGQGT
  121 TVTVSSASTK GPSVFPLAPS SKSTSGGTAA LGCLVKDYFP EPVTVSWNSG ALTSGVHTFP
  181 AVLQSSGLYS LSSVVTVPSS SLGTQTYICN VNHKPSNTKV DKRVEPKSCD KTHTCPPCPA
  241 PELLGGPSVF LFPPKPKDTL MISRTPEVTC VVVDVSHEDP EVKFNWYVDG VEVHNAKTKP
  301 REEQYNSTYR VVSVLTVLHQ DWLNGKEYKC KVSNKALPAP IEKTISKAKG QPREPQVYTL
  361 PPSREEMTKN QVSLTCLVKG FYPSDIAVEW ESNGQPENNY KTTPPVLDSD GSFFLYSKLT
  421 VDKSRWQQGN VFSCSVMHEA LHNHYTQKSL SLSPGKGGGG SGGGGSQVQL VQSGAEVKKP
  481 GSSVKVSCKA SGGTFSTYGI SWVRQAPGQC LEWMGGIIPI FDTGNSAQSF QGRVTITADE
  541 STSTAYMELS SLRSEDTAVY YCARSSRIYD LNPSLTAYYD MDVWGQGTMV TVSSGGGGSG
  601 GGGSGGGGSG GGGSQSVLTQ PPSVSAAPGQ KVTISCSGSS SNIGNNYVSW YQQLPGTAPK
  661 LLIYDNNKRP SGIPDRFSGS KSGTSATLGI TGLQTGDEAD YYCGTWDSSL SAWVFGCGTK
  721 LTVL SEQ ID NO: 23 - ndimab varB - H chain nucleotide sequence
    1 CAGGTGCAGC TGGTGGAAAG CGGCGGAGGC GTGGTGCAGC CCGGCAGAAG CCTGAGACTG
   61 AGCTGCGCTG CCAGCGGCTT CATCTTCAGC AGCTACGCCA TGCACTGGGT CCGCCAGGCC
  121 CCTGGCAACG GACTGGAATG GGTGGCCTTC ATGAGCTACG ACGGCAGCAA CAAGAAGTAC
  181 GCCGACAGCG TGAAGGGCCG GTTCACCATC AGCCGGGACA ACAGCAAGAA CACCCTGTAC
  241 CTGCAGATGA ACAGCCTGCG GGCTGAGGAC ACCGCCGTGT ACTACTGCGC CAGAGACCGA
  301 GGCATCAGTG CTGGCGGCAA CTACTACTAC TACGGCATGG ACGTGTGGGG CCAGGGCACC
  361 ACCGTGACCG TGTCTAGCGC GTCGACCAAG GGCCCATCCG TCTTCCCCCT GGCACCCTCC
  421 TCCAAGAGCA CCTCTGGGGG CACAGCGGCC CTGGGCTGCC TGGTCAAGGA CTACTTCCCG
  481 GAACCGGTGA CGGTGTCCTG GAACTCAGGC GCTCTGACCA GCGGCGTGCA CACCTTCCCG
  541 GCTGTCCTAC AGTCCTCAGG ACTCTACTCC CTCAGCAGCG TGGTGACCGT GCCCTCCAGC
  601 AGCTTGGGCA CCCAGACCTA CATCTGCAAC GTGAATCACA AGCCCAGCAA CACCAAGGTG
  661 GACAAGAGAG TTGAGCCCAA ATCTTGTGAC AAAACTCACA CATGCCCACC GTGCCCAGCA
  721 CCTGAACTCC TGGGGGGACC GTCAGTCTTC CTCTTCCCCC CAAAACCCAA GGACACCCTC
  781 ATGATCTCCC GGACCCCTGA GGTCACATGC GTGGTGGTGG ACGTGAGCCA CGAAGACCCT

```
 841 GAGGTCAAGT TCAACTGGTA CGTGGACGGC GTGGAGGTGC ATAATGCCAA GACAAAGCCG
 901 CGGGAGGAGC AGTACAACAG CACGTACCGT GTGGTCAGCG TCCTCACCGT CCTGCACCAG
 961 GACTGGCTGA ATGGCAAGGA GTACAAGTGC AAGGTCTCCA ACAAAGCCCT CCCAGCCCCC
1021 ATCGAGAAAA CCATCTCCAA AGCCAAAGGG CAGCCCCGAG AACCACAGGT CTACACCCTG
1081 CCCCCATCCC GGGAGGAGAT GACCAAGAAC CAGGTCAGCC TGACCTGCCT GGTCAAAGGC
1141 TTCTATCCCA GCGACATCGC CGTGGAGTGG GAGAGCAATG GGCAGCCGGA GAACAACTAC
1201 AAGACCACGC CTCCCGTGCT GGACTCCGAC GGCTCCTTCT TCCTCTATAG CAAGCTCACC
1261 GTGGACAAGA GCAGGTGGCA GCAGGGGAAC GTCTTCTCAT GCTCCGTGAT GCATGAGGCT
1321 CTGCACAACC ACTACACGCA GAAGAGCCTC TCCCTGTCTC CGGGTAAAGG CGGAGGGGGA
1381 TCCGGCGGAG GGGGCTCTCA GGTGCAGCTG GTGCAGTCTG GCGCCGAAGT GAAGAAACCC
1441 GGCTCTAGCG TGAAGGTGTC CTGCAAGGCC AGCGGCGGCA CCTTCTCCAC CTACGGCATC
1501 AGCTGGGTCC GCCAGGCCCC TGGACAGTGT CTGGAATGGA TGGGCGGCAT CATCCCCATC
1561 TTCGACACCG GCAACAGCGC CCAGAGCTTC CAGGGCAGAG TGACCATCAC CGCCGACGAG
1621 AGCACCTCCA CCGCCTACAT GGAACTGAGC AGCCTGCGGA GCGAGGACAC CGCCGTGTAC
1681 TACTGCGCCA GAAGCAGCCG GATCTACGAC CTGAACCCCA GCCTGACCGC CTACTACGAC
1741 ATGGACGTGT GGGGCCAGGG CACCATGGTC ACAGTGTCTA GCGGAGGCGG AGGCAGCGGA
1801 GGTGGTGGAT CTGGTGGCGG AGGAAGTGGC GGCGGAGGCT CTCAGAGCGT GCTGACCCAG
1861 CCCCCTTCTG TGTCTGCCGC CCCTGGCCAG AAAGTGACCA TCTCCTGCAG CGGCAGCAGC
1921 AGCAACATCG GCAACAACTA CGTGTCCTGG TATCAGCAGC TGCCCGGCAC CGCCCCTAAG
1981 CTGCTGATCT ACGACAACAA CAAGCGGCCC AGCGGCATCC CCGACCGGTT TAGCGGCAGC
2041 AAGAGCGGGA CTTCTGCTAC ACTGGGCATC ACAGGCCTGC AGACCGGCGA CGAGGCCGAC
2101 TACTACTGCG GCACCTGGGA CAGCAGCCTG AGCGCTTGGG TGTTCGGCTG CGGCACCAAG
2161 CTGACAGTGC TG

SEQ ID NO: 24 - NGF-NG VH amino acid sequence
QVQLVQSGAEVKKPGSSVKVSCKASGGTFWFGAFTWVRQAPGQGLEWMGGIIPIFGLTNLAQNFQGRVTITADESTSTVY
MELSSLRSEDTAVYYCARSSRIYDLNPSLTAYYDMDVWGQGTMVTVSS SEQ ID NO: 25 - NGF-NG VH nucleotide sequence
caggtgcagc tggtgcagtc tggggctgag gtgaagaagc ctgggtcctc ggtgaaggtc   60
tcctgcaagg cctctggagg caccttctgg ttcggcgcgt tcacctgggt gcgacaggcc  120
cctggacaag gacttgagtg gatgggaggg attattccta tcttcgggtt gacgaacttg  180
gcacagaact tccagggcag agtcacgatt accgcggacg aatccacgag cacagtctac  240
atggagctga gcagcttgag atctgaagac acggccgtat attattgtgc acgttcaagt  300
cgtatctacg atctgaaccc gtccctgacc gcctactacg atatggatgt ctggggccag  360
gggacaatgg tcaccgtctc gagt                                         384

SEQ ID NO: 26 - NGF-NG VL amino acid sequence
QSVLTQPPSVSAAPGQKVTISCSGSSSDIGNNYVSWYQQLPGTAPKLLIYDNNKRPSGIPDRFSGSKSGTSATLGITGLQ
TGDEADYYCGTWDSSLSAWVFGGGTKLTVL SEQ ID NO: 27 - NGF-NG VL nucleotide sequence
cagtctgtgc tgactcagcc gccatcagtg tctgcggccc caggacagaa ggtcaccatc   60
tcctgctctg gaagcagctc cgacattggg aataattatg tatcgtggta ccagcagctc  120
ccaggaacag ccccccaaact cctcatttat gacaataata agcgaccctc agggattcct  180
gaccgattct ctggctccaa gtctggcacg tcagccaccc tgggcatcac cggactccag  240
actggggacg aggccgatta ttactgcgga acatgggata gcagcctgag tgcttgggtg  300
ttcggcggag ggaccaagct gaccgtccta                                   330

SEQ ID NO: 28 - ndimab VH amino acid sequence
   1 QVQLVESGGG VVQPGRSLRL SCAASGFIFS SYAMHWVRQA PGNGLEWVAF MSYDGSNKKY
  61 ADSVKGRFTI SRDNSKNTLY LQMNSLRAED TAVYYCARDR GISAGGNYYY YGMDVWGQGT
 121 TVTVSS SEQ ID NO: 29 - ndimab VL amino acid sequence
   1 EIVLTQSPAT LSLSPGERAT LSCRASQSVY SYLAWYQQKP GQAPRLLIYD ASNRAIGIPA
  61 RFSGSGSGTD FTLTISSLEP EDFAVYYCQQ RSNWPPFTFG PGTKVDIK SEQ ID NO: 30 - 1126F1 VH amino acid sequence
EVQLVQTGAEVKKPGSSVKVSCKASGGTFSTYGISWVRQAPGQGLEWIGGIIPIFDTGNSAQSFQGRVTITADESTSTAY
MEVSSLRSDDTAVYYCASSSRIYDANRQAVPYYDMDVWGQGTMVTVSS SEQ ID NO: 31 - 1126F1 VL amino acid sequence
QAVLTQPSSVSTPPGQMVTISCSGSSSDIGNNYVSWYQQLPGTAPKLLIYDNNKRPSGIPDRFSGSKSGTSATLGITGLQ
TGDEADYYCGTWDSSLSAWVFGGGTKLTVL SEQ ID NO: 32 - 1126G5 VH amino acid sequence
EVQLVQSGAEVKKPGSSVKVSCKASGGTFSTYGISWVRQAPGQGLEWIGGIIPIFDTGNSAQSFQGRVTITADESTSTAY
MEVSSLRSDDTAVYYCASSSRIYDFTSGLAPYYDMDVWGQGTMVTVSS SEQ ID NO: 33 - 1126G5 VL amino acid sequence
QAVLTQPSSVSTPPGQKVTISCSGSSSNIGNNYVSWYQQLPGTAPKLLIYDNNKRPPGIPDRFSGSKSGTSATLGITGLQ
TGDEADYYCGTWDSSLSTWVFGGGTKLTVL SEQ ID NO: 34 - 1126H5 VH amino acid sequence
EVQLVQSGAEVKKPGSSVKVSCKASGGTESTYGISWVRQAPGQGLEWIGGIIPIFDAGNSAQSFQGRVTITADESTSTAH
MEVSSLRSEDTAVYYCASSSRIYDHHIQKGGYYDMDVWGQGTMVTVSS
```

-continued

Sequence listing

SEQ ID NO: 35 - 1126H5 VL amino acid sequence
QAVLTQPSSVSTPPGQKVTISCSGSSSNIGNNYVSWYQQLPGTAPKLLIYDNNKRPSGIPDRFSGSKSGTSATLGITGLQ
TGDEADYYCGTWDSSLSAWVFGGGTKLTVL SEQ ID NO: 36 - 1127D9 VH amino acid sequence
EVQLVQSGAEVKKPGSSVKVSCKASGGTFSTYGISWVRQAPGQGLEWIGGIIPIFDTGNSAQSFQGRVTITADESTSTAY
MEVSSLRSDDTAVYYCASSSRIYDYHTIAYYD SEQ ID NO: 37 - 1127D9 VL amino acid sequence
QAVLTQPSSVSTPPGQKVTISCSGSSSNIGNNYVSWYQQLPGTAPKLLIYDNNKRPSGIPDRFSGSKSGTSATLGITGLQ
TGDEADYYCGTWDSSLSAWVFGGGTKLTVL SEQ ID NO: 38 - 1127E9 VH amino acid sequence
EVQLVQSGAEVKKPGSSVKVSCKASGGTFSTYGISWVRQAPGQGLEWIGGIIPIFDTGNSAQSFQGRVTITADESTSTAY
MKVSSLRSDDTAVYYCASSSRIYDYIPGMRPYYDMDVWGQGTMVTVSS SEQ ID NO: 39 - 1127E9 VL amino acid sequence
QAVLTQPSSVSTPPGQKVTISCSGNSSNIGNNYVSWYQQLPGTAPKLLIYDNNKRPSGIPDRFSGSRSGTLATLGITGLQ
TGDEADYYCGTWDSSLSAWVFGGGTKLTVL SEQ ID NO: 40 - 1131D7 VH amino acid sequence
EVQLVQSGAEVKKPGSSVKVSCKASGGTFSTYGISWVRQAPGQGLEWIGGIIPIFDTGNSAQSFQGRVTITADESTSTAY
MEVSSLRSDDTAVYYCASSSRIYDFNSSLIAYYDMDVWGQGTMVTVSS SEQ ID NO: 41 - 1131D7 VL amino acid sequence
QAVLTQPSSVSTPPGQKVTISCSGSSSNIGNNYVSWYQQLPGTAPKLLIYDNNKRPSGIPDRFSGSKSGTSATLGITGLQ
TGDETDYYCGTWDSSLSAWVFSGGTKLTVL SEQ ID NO: 42 - 1131H2 VH amino acid sequence
EVQLVQSGAEVKKPGSTVKVSCKASGGTFSTYGISWVRQAPGQGLEWIGGIIPIFDTGNSAQSFQGRVTITADESTSTAY
MEVSSLRSDDTAVYYCASSSRIYDLNPSLTAYYDMDVWGQGTMVTVSS SEQ ID NO: 43 - 1131H2 VL amino acid sequence
QAVLTQPSSVSTPPGQKVTISCSGTSSNIGNNYVSWYQQLPGTAPKLLIYDNNKRPSGIPDRFSGSKSGTSATLGITGLQ
TGDEADYYCGTWDSSLSAWVFGGGTKLTVL SEQ ID NO: 44 - 132A9 VH amino acid sequence
EVQLVQSGAEVKKPGSSVKVSCKASGGTFSTYGISWVRQAPGQGLEWIGGIIPIFGTGNSAQSFQGRVTITADESTSTAY
MEVSSLRSDDTAVYYCASSSRIYDFEPSLIYYYDMDVWGQGTMVTVSS SEQ ID NO: 45 - 132A9 VL amino acid sequence
QAVLTQPSSVSTPPGQKVTISCSGSSSNIGNNYVSWYQQLPGTAPKLLIYDNNKRPSGIPDRFSGSKSGTSATLGITGLQ
TGDEADYYCGTWDSSLSAWVFGGGTKLTVL SEQ ID NO: 46 - 1132H9 VH amino acid sequence
EVQLVQSGAEVKKPGSSVKVSCKASGGTFSTYGISWVRQAPGQGLEWIGGIIPIFDTGNSAQSFQGRVTITADESTSTAY
MEVSSLRSDDTAVYYCASSSRIYDLNPSLTAYYDMDVWGQGTMVTVSS SEQ ID NO: 47 - 1132H9 VL amino acid sequence
QAVLTQPSSVSTPPGQKVTISCSGSSSDIGNNYVSWYQQLPGTAPKLLIYDNNKRPTGIPDRFSGSKSGTSATLGITGLQ
TGDEADYYCGTWDSSLSAWVFGGGTKLTVL SEQ ID NO: 48 - 1133C11 VH amino acid sequence
EVQLVQSGAEVKKPGSSVKVSCKASGGTFSTYGISWVRQAPGQGLEWIGGIIPIFDTGNSAQSFQGRVTITADESTSTAY
MEVSSLRSDDTAVYYCASSSRIYDLNPSLTAYYDMDVWGQGTMVTVSS SEQ ID NO: 49 - 1133C11 VL amino acid sequence
QAVLTQPSSVSTPPGQKVTISCSGSSSNIGNNYVSWYQQLPGTAPKLLIYDNNKRPSGIPDRFSGSKSGTSATLGITGLQ
TGDEADYYCGTWDSSLSAWVFGGGTKLTVL SEQ ID NO: 50 - 1134D9 VH amino acid sequence
EVQLVQSGAEVKKPGSSVKVSCKASGGTFSTYGISWVRQAPGQGLEWIGGIIPIFDTGNSAQSFQGRVAITADESTSTAY
MEVSSLRSDDTAVYYCASSSRIYDLNPSLTAYYDMDVWGQGTMVTVSS SEQ ID NO: 51 - 1134D9 VL amino acid sequence
QAVLTQPSSVSTPPGQKVTISCSGSSSNIGNNYVSWYQQLPGTAPKLLIYDNNKRPSGIPDRFSGSKSGTSATLGITGLQ
TGDEADYYCGTWDSGLSAWVFGGGTKLTVL SEQ ID NO: 52 - 1145D1 VH amino acid sequence
EVQLVQSGAEVKKPGSSVKVSCKASGGTFSTYGISWVRQAPGQGLEWIGGIIPIFDTSNSAQSFQGRVTITADESTSTAY
MEVSSLRSDDTAVYYCASSSRIYDFRTLYSTYYDMDVWGQGTMVTVSS SEQ ID NO: 53 - 1145D1 VL amino acid sequence
QAVLTQPSSVSTPPGQKVTISCSGSSSNIGNNYVSWYQQLPGTAPKLLIYDNNKRPSISDRFSGSKSGTSATLGIAGLQ
TGDEADYYCGTWDSSLSAWVFGGGTKLTVL

| Sequence listing |
| --- |

SEQ ID NO: 54 - 1146D7 VH amino acid sequence
EVQLVQSGAEVKKPGSSVKVSCKASGGTFSTYGISWVRQAPGQGLEWIGGIIPIFDTGNSAQSFQGRVTITADESTSTAY
MEVSSLRSDDTAVYYCASSSRIYDLNPSLTAYYDMDVWGQGTMVTVSS SEQ ID NO: 55 - 1146D7 VL amino acid sequence
QAVLTQPSSVSTPPGQEVTISCSGSSTNIGNNYVSWYQQLPGTAPKLLIYDNNKRPSGIPDRFSGSKSGTSATLGITGLQ
TGDEADYYCGTWDSSLSAWVFGGGTKLTVL SEQ ID NO: 56 - 1147D2 VH amino acid sequence
EVQLVQSGAEVKKPGSSVRISCKASGGTFSTYGISWVRQAPGQGLEWIGGIIPIFDTGNSAQSFQGRVTITADESTSTAY
MEVSSLRSDDTAVYYCASSSRIYDLNPSLTAYYDMDVWGQGTMVTVSS SEQ ID NO: 57 - 1147D2 VL amino acid sequence
QAVLTQPSSVSTPPGQKVTISCSGSSSNIGNNYVSWYQQLPGTAPKLLIYDNNKRPSGVPDRFSGSKSGTSATLGITGLQ
TGDEADYYCGTWDSSLSAWVFGGGTKLTVL SEQ ID NO: 58 - 1147G9 VH amino acid sequence
EVQLVQSGAEVKKPGSSVKVSCKASGGTFSAYGISWVRQAPGQGLEWIGGIIPIENTGNSAQSFQGRVTITADESTSTAY
MEVSSLRSDDTAVYYCASSSRIYDLNPSLTAYYDMDVWGQGTMVTV SEQ ID NO: 59 - 1147G9 VL amino acid sequence
QAVLTQPSSVSTPPGQKVTVSCSGSSSNIGNNYVSWYQQLPGTAPKLLIYDNNKRPSGIPDRFSGSKSGTSATLGITGLQ
TGDEADYYCGTWDSSLSAWVFGGGTKLTVL SEQ ID NO: 60 - 1150F1 VH amino acid sequence
EVQLVQSGAEVKKPGSSVKVSCKASGGTFSTYGISWVRQAPGQGLEWIGGIIPIFDTGNSAQSFQDRVTITADESTSTAY
MEVGSLRSDDTAVYYCASSSRIYDLNPSLTAYYDMDVWGHGTMVTVSS SEQ ID NO: 61 - 1150F1 VL amino acid sequence
QAVLTQPSSVSTPPGQKVTISCSGSSSNIGNNYVSWYQQLPGTAPKLLIYDNNKRPSGIPDRFSGSKSGTSATLGITGLQ
TGDEADYYCGTWDSSLSAWVFGGGTKLTVL SEQ ID NO: 62 - 1152H5 VH amino acid sequence
EVQLVQSGAEVKKPGSSVKVSCKASGGTFSTYGISWVRQAPGQGLVWIGGIIPIFDTGNSAQSFQGRVTITADESTSTAY
MEVSSLRSDDTAVYYCASSSRIYDMISSLQPYYDMDVWGQGTMVTVSS SEQ ID NO: 63 - 1152H5 VL amino acid sequence
QAVLTQPSSVSTPPGQKATISCSGSSSNIGNNYVSWYQQLPGTAPKLLIYDNNKRPSGIPDRFSGSKSGTSATLGITGLQ
TGDEADYYCGTWDSSLSAWVFGGGTKLTVL SEQ ID NO: 64 - 1155H1 VH amino acid sequence
EVQLVQSGAEVKKPGSSVKVSCKASGGTFSTYGISWVRQAPGQGLEWIGGIIPIFDTGNSAQSFQGRVTITADESTSTAY
MEVSSLRSDDTAVYYCASSSRIYDFHLANKGYYDMDVWGQGTMVTVSS SEQ ID NO: 65 - 1155H1 VL amino acid sequence
QAVLTQPSSVSTPPGQKATISCSGSSSNIGNNYVSWYQQLPGTAPKLLIYDNNKRPSGIPDRFSGSKSGTSATLDITGLQ
TGDEADYYCGTWDSSLSAWVFGGGTKLTVL SEQ ID NO: 66 - 1158A1 VH amino acid sequence
EVQLVQSGAEVKKPGSSVKVSCKASGGTFSTYGISWVRQAPGQGLEWIGGIIPIFGTGNSAQSFQGRVTITADESTSTAY
MEVSSLRSDDTAVYYCASSSRIYDHHNHVGGYYDMDVWGQGTMVTVSS SEQ ID NO: 67 - 1158A1 VL amino acid sequence
QAVLTQPSSVSTPPGQKVTISCSGSSSNIGNNYASWYQQLPGTAPKLLIYDNNKRPSGIPDRFSGSKSGTSATLGITGLQ
TGDEADYYCGTWDGSLSAWVFGGGTKLTVL SEQ ID NO: 68 - 1160E3 VH amino acid sequence
EVQLVQSGAEVKKPGSSAKVSCKASGGTFSTYGISWVRQAPGQGLEWIGGIIPIFDTGNSAQSFQGRVTITADESTSTAY
MEVSSLRSDDTAVYYCASSSRIYDLNPSLTAYYDMDVWGQGTMVTVSS SEQ ID NO: 69 - 1160E3 VL amino acid sequence
QAVLTQPSSVSTPPGQKVTISCSGSNSNIGNNYVSWYQQLPGTAPKLLIYDNNKRPSGIPDRFSGSKSGTSATLGITGLQ
TGDEADYYCGTWDSSLSAWVFGGGTKLTV SEQ ID NO: 70 - 1165D4 VH amino acid sequence
EVQLVQSGAEVKKPGSSVKVSCKASGGTFSTYGISWVRQAPGQGLEWIGGIIPIFDTGNSAQSFQGRVTITADESTSTAY
MEVSSLRSDDTAVYYCASSSRIYDLNPSLTAYYDMDVWGQGTMVTVSS SEQ ID NO: 71 - 1165D4 VL amino acid sequence
QAVLTQPSSVSTPPGQKVTISCSGSSSNIENNYVSWYQQLPGTAPKLLIYDNNKRPSGIPDRFSGSKSGTSATLGITGLQ
TGDEADYYCGTWDSSLSAWVFGGGTKLTVL SEQ ID NO: 72 - 1175H8 VH amino acid sequence
EVQLVQSGAEVKKPGSSVKVSCKASGGTFSTYGISWVRQAPGQRLEWIGGIIPIFDTGNSAQSFQGRVTITADESTSTAY
MEVSSLRSDDTAVYYCASSSRIYDATTGLTPYYDMDVWGQGTMVTVSS

| Sequence listing |
|---|

SEQ ID NO: 73 - 1175H8 VL amino acid sequence
QAVLTQPSSVSTPPGQKVTISCSGSSSNIGNNYVSWYQQLPGTAPKLLIYDNNKRPSGIPDRFSGSKSGTSATLGITGLR
TGDEADYYCGTWDSSLSAWVFGGGTKLTVL SEQ ID NO: 74 - 1211G10 VH amino acid sequence
EVQLVQSGAEVRKPGSSVKVSCKAYGGTFSTYGISWVRQAPGQGLEWVGGIIPIFDTRNSAQSFQGRVTITADESTSTAY
MEVSSLRSDDTAVYYCASSSRIYDMVSTLIPYYDMDVWGQGTMVTVSS SEQ ID NO: 75 - 1211G10 VL amino acid sequence
QAVLTQPSSVSTPPGQKVTISCSGSSSNIGNNYVSWYQQLPGTAPKLLIYDNNKRPSGIPDRFSGSKSGTSATLGITGLQ
TGDEADYYCGTWDSSLSAWVFGGGTKLTVL SEQ ID NO: 76 - 1214A1 VH amino acid sequence
EVQLVQSGAEVKKPGSSVRVSCKASGGTFSTYGISWVRQAPGQGLEWIGGIIPIFDTGNSAQSFQGRVTITADESTSTAY
MEVSSLRSDDTAVYYCASSSRIYDAHLQAYYDMDVWGQGTMVTVSS SEQ ID NO: 77 - 1214A1 VL amino acid sequence
QAVLTQPSSVSTPPGQKVTISCSGSSSNIGNNYVSWYQQLPGTAPKLLIYDNNKRPPGIPDRFSGSKSGTSATLGITGLQ
TGDEADYYCGTRDSSLSAWVFGGGTKLTVL SEQ ID NO: 78 - 1214D10 VH amino acid sequence
EVQLVQSGAEAKKPGSSVKVSCKASGGTFSTYGISWVRQAPGRGLEWIGGIIPIFDTGNSAQSFQGRVAITADESTSTAY
MEVSSLRSDDTAVYYCASSSRIYDAHLNHHGYYDMDVWGQGTMVTVSS SEQ ID NO: 79 - 1214D10 VL amino acid sequence
QAVLTQPSSVSTPPGQKVTISCSGSSSNIGNNYVSWYQQLPGTAPKLLIYDNNKRPSGIPDRFSGSKSGTSATLGITGLQ
AGDEADYYCGTWDSSLSAWVFGGGTKLTVL SEQ ID NO: 80 - 1218H5 VH amino acid sequence
EVQLVQSGAVVKKPGSSVKVSCKASGGTFSTYGISWVRQAPGQGLEWIGGIIPIFDTGSSAQSFQGRVTITADESTSTAY
MEVSSLRSDDTAVYYCASSSRIYDLNPSLTAYYDMDVWGQGTMVTVSS SEQ ID NO: 81 - 1218H5 VL amino acid sequence
QAVLTQPSSVSTPPGQKVTISCSGSSSNTGNNYVSWYQQLSGTAPKLLIYDNNKRPSGIPDRFSGSKSGTSATLGITGLQ
TGDEADYYCGTWDSSLSAWVFGGGTKLTVL SEQ ID NO: 82 - 1230H7 VH amino acid sequence
EMQLVQSGAEVKKPGSSVKVSCKASGGTFSTYGISWVRQAPGQGLEWIGGIIPIFDTGNSAQSFQGRVTITADESTSTAY
MEVSSLRSDDTAVYYCASSSRIYDFNSALISYYDMDVWGQGTMVTVSS SEQ ID NO: 83 - 1230H7 VL amino acid sequence
QAVLTQPSSVSTPPGQKVTISCSGSSSNIGNNYVSWYQQLPGTAPKLLIYDNNKRPSGIPDRFSGSKSGTSATLGITGLQ
TGDEADYYCGTWDSSLSAWVFGGGTKLTV SEQ ID NO: 84 - 1083H4 VH amino acid sequence
QMQLVQSGAEVKKTGSSVKVSCKASGYTFAYHYLHWVRQAPGQGLEWMGGIIPIEGTTNYAQRFQDRVTITADESTSTAY
MELSSLRSEDTAVYYCASADYVWGSYRPDWYFDLWGRGTMVTVSS SEQ ID NO: 85 - 1083H4 VL amino acid sequence
QSVLTQPPSASGTPGQRVTISCSGSSSNIGSNTVNWYQRLPGAAPQLLIYNNDQRPSGIPDRFSGSKSGTSGSLVISGLQ
SEDEADYYCASWDDSLNGRVFGGGTKLTVL SEQ ID NO: 86 - 1227H8 VH amino acid sequence
QMQLVQSGAEVKKTGSSVKVSCKASGHTFAYHYLHWVRQAPGQGLEWMGGIIPIEGTTNYAQRFQDRVTITADESTSTAY
MELSSLRSEDTAVYYCASADYAWESYQPPQINGVWGRGTMVTVSS SEQ ID NO: 87 - 1227H8 VL amino acid sequence
QSVLTQPPSVSAAPGQKVTITCSGSTSNIGNNYVSWYQQHPGKAPKLMIYDVSKRPSGVPDRFSGSKSGNSASLDISGLQ
SEDEADYYCAAWDDSLSEFFFGTGTKLTVL

SEQ ID NO: 88 - NGF-NG HCDR1
FGAFT

SEQ ID NO: 89 - NGF-NG HCDR2
GIIPIFGLTNLAQNFQG

SEQ ID NO: 90 - NGF-NG HCDR3
SSRIYDLNPSLTAYYDMDV

SEQ ID NO: 91 - NGF-NG LCDR1
SGSSSDIGNNYVS

SEQ ID NO: 92 - NGF-NG LCDR2
DNNKRPS

Sequence listing

SEQ ID NO: 93 - NGF-NG LCDR3
GTWDSSLSAWV

SEQ ID NO: 94 - MEDI-578 VH amino acid sequence with G→C
QVQLVQSGAE VKKPGSSVKV SCKASGGTFS TYGISWVRQA PGQCLEWMGG IIPIFDTGNS
AQSFQGRVTI TADESTSTAY MELSSLRSED TAVYYCARSS RIYDLNPSLT AYYDMDVWGQ
GTMVTVSS SEQ ID NO: 95 - MEDI-578 VL amino acid sequence with G→C
QSVLTQPPSV SAAPGQKVTI SCSGSSSNIG NNYVSWYQQL PGTAPKLLIY DNNKRPSGIP
DRFSGSKSGT SATLGITGLQ TGDEADYYCG TWDSSLSAWV FGCGTKLTVL SEQ ID NO: 96 - 1230D8 VH amino acid sequence
QMQLVQSGAEVKKTGSSVKVSCKASGYTFPYHYLHWVRQAPGQGLEWMGGIIPIEGTTNYAQRFQDRVTITADESTSTAY
MEFSSLRSEDTAVYYCASADYVWESYHPATSLSLWGRGTMVTVSS SEQ ID NO: 97 - 1230D8 VL amino acid sequence
QSVLTQPPSVSAAPGQKVTISCPGSTSNIGNNYVSWYQQRPGKAPKLMIYDVSKRPSGVPDRFSGSKSGNSASLDISELQ
SEDEADYYCAAWDDSLSEFLFGTGTKLTVL

SEQ ID NO: 98
GGGGSGGGGS

SEQ ID NO: 99 - TNFR2-Fc_varB - codon optimized nucleotide sequence
```
   1 CTGCCCGCCC AGGTGGCCTT TACCCCTTAT GCTCCTGAGC CCGGCTCTAC CTGCCGGCTG
  61 AGAGAGTACT ACGACCAGAC CGCCCAGATG TGCTGCTCCA AGTGCTCTCC TGGCCAGCAC
 121 GCCAAGGTGT TCTGCACCAA GACCTCCGAT ACCGTGTGCG ACTCCTGCGA GGACTCCACC
 181 TACACCCAGC TGTGGAACTG GGTGCCCGAG TGCCTGTCCT GCGGCTCCAG ATGTTCCTCC
 241 GACCAGGTGG AAACCCAGGC CTGCACCAGA GAGCAGAACC GGATCTGCAC CTGTCGGCCT
 301 GGCTGGTACT GCGCCCTGTC TAAGCAGGAA GGCTGCAGAC TGTGCGCCCC TCTGCGGAAG
 361 TGTAGACCTG GCTTTGGCGT GGCCAGACCC GGCACCGAGA CATCTGATGT CGTGTGCAAG
 421 CCTTGCGCCC CTGGCACCTT CTCCAACACC ACCTCCTCCA CCGACATCTG CCGGCCTCAC
 481 CAGATCTGCA ACGTGGTGGC CATCCCTGGC AACGCCTCTA TGGACGCCGT GTGCACCTCT
 541 ACCTCCCCCA CCAGAAGTAT GGCCCCTGGC GCTGTGCATC TGCCCCAGCC TGTGTCTACC
 601 AGATCCCAGC ACACCCAGCC CACCCCTGAG CCTTCTACCG CCCCTTCTAC CAGCTTCCTG
 661 CTGCCTATGG GCCCTAGCCC TCCTGCTGAG GGATCTACAG GCGACGAGCC CAAGTCCTGC
 721 GACAAGACCC ACACCTGTCC CCCTTGTCCT GCCCCTGAAC TGCTGGGCGG ACCTTCCGTG
 781 TTCCTGTTCC CCCCAAAGCC CAAGGACACC CTGATGATCA GCCGGACCCC TGAAGTGACC
 841 TGCGTGGTGG TGGATGTGTC CCACGAGGAT CCCGAAGTGA AGTTCAATTG GTACGTGGAC
 901 GGCGTGGAAG TGCACAACGC CAAGACCAAG CCCAGAGAGG AACAGTACAA CTCCACCTAC
 961 CGGGTGGTGT CCGTGCTGAC CGTGCTGCAC CAGGATTGGC TGAACGGCAA AGAGTACAAG
1021 TGCAAGGTGT CCAACAAGGC CCTGCCTGCC CCCATCGAAA AGACCATCTC CAAGGCCAAG
1081 GGCCAGCCCC GGGAACCCCA GGTGTACACA CTGCCCCCTA GCCGGGAAGA GATGACCAAG
1141 AACCAGGTGT CCCTGACCTG TCTCGTGAAG GGCTTCTACC CCTCCGATAT CGCCGTGGAA
1201 TGGGAGTCCA ACGGCCAGCC TGAGAACAAC TACAAGACCA CCCCCCCTGT GCTGGACTCC
1261 GACGGCTCAT TCTTCCTGTA CTCCAAGCTG ACAGTGGACA AGTCCCGGTG GCAGCAGGGC
1321 AACGTGTTCT CCTGCTCCGT GATGCACGAG GCCCTGCACA ACCACTACAC CCAGAAGTCC
1381 CTGTCCCTGA GCCCTGGAAA AGGCGGCGGA GGATCTGGCG GAGGCGGATC TCAGGTGCAG
1441 CTGGTGCAGT CTGGCGCTGA AGTGAAGAAA CCCGGCTCCT CCGTGAAGGT GTCCTGCAAG
1501 GCTTCTGGCG GCACCTTCTC TACCTACGGC ATCTCCTGGG TGCGACAGGC CCCTGGCCAG
1561 TGCCTGGAAT GGATGGGCGG CATCATCCCC ATCTTCGACA CCGGCAACTC CGCCCAGAGC
1621 TTCCAGGGCA GAGTGACCAT CACCGCCGAC GAGTCTACCT CCACCGCCTA CATGGAACTG
1681 TCCTCCCTGC GGAGCGAGGA CACCGCCGTG TACTACTGCG CCCGGTCCTC TCGGATCTAC
1741 GACCTGAACC CTTCCCTGAC CGCCTACTAC GACATGGACG TGTGGGGCCA GGGCACAATG
1801 GTCACCGTGT CATCTGGTGG TGGCGGCTCT GGTGGCGGAG GAAGTGGGGG AGGGGGTTCT
1861 GGGGGGGGAG GATCTCAGTC TGTGCTGACC CAGCCTCCTT CCGTGTCTGC TGCCCCAGGC
1921 CAGAAAGTGA CAATCTCCTG CAGCGGCTCC AGCTCCAACA TCGGCAACAA CTACGTGTCC
1981 TGGTATCAGC AGCTGCCCGG CACCGCTCCC AAACTGCTGA TCTACGATAA CAACAAGCGG
2041 CCCTCCGGCA TCCCCGACAG ATTCTCCGGC TCTAAGTCCG GCACCTCTGC CACCCTGGGC
2101 ATCACCGGAC TGCAGACAGG CGACGAGGCC GACTACTACT GTGGCACCTG GGACTCCTCC
2161 CTGTCCGCTT GGGTGTTCGG CTGCGGCACC AAACTGACTG TGCTG
```

The disclosure is not to be limited in scope by the specific aspects described which are intended as single illustrations of individual aspects of the disclosure, and any compositions or methods that are functionally equivalent are within the scope of this disclosure. Indeed, various modifications of the disclosure in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. A binding molecule comprising an NGF antagonist domain and a TNFα antagonist domain, wherein the NGF antagonist domain comprises an anti-NGF antibody or fragment thereof; wherein the TNFα antagonist domain comprises a soluble, TNFα-binding fragment of TNFR-2; wherein the anti-NGF antibody or fragment thereof comprises a VH domain comprising a set of CDRs HCDR1, HCDR2, HCDR3 and a VL domain comprising a set of CDRs LCDR1, LCDR2 and LCDR3, wherein the HCDR1 has the amino acid sequence of SEQ ID NO: 4, the HCDR2 has the amino acid sequence of SEQ ID NO: 5, the HCDR3 has the amino acid sequence of any one of SEQ ID NOs: 6, 11 or 12, the LCDR1 has the amino acid sequence of SEQ ID NO: 8, the LCDR2 has the amino acid sequence of SEQ ID NO: 9, and the LCDR3 has the amino acid sequence of SEQ ID NO: 10; wherein a cysteine is present in the VH domain at the amino acid corresponding to amino acid position 44 of SEQ ID NO: 94; and wherein a cysteine is present in the VL domain at the amino acid corresponding to amino acid position 103 of SEQ ID NO: 95.

2. The binding molecule of claim 1, wherein the anti-NGF antibody or fragment thereof is an scFv, and wherein the scFv is SS-stabilized.

3. The binding molecule of claim 1, wherein the TNFα antagonist inhibits binding of TNFα to a TNF receptor (TNFR) on the surface of cells, thereby blocking TNFα activity.

4. The binding molecule of claim 1, wherein the TNFα antagonist comprises a soluble, TNFα-binding fragment of TNFR-2 fused to an immunoglobulin Fc domain.

5. The binding molecule of claim 4, wherein the immunoglobulin Fc domain is a human IgG1 Fc domain.

6. The binding molecule of claim 1, wherein the TNFα antagonist comprises an amino acid sequence that is at least 90% identical to SEQ ID NO: 13, or a functional fragment thereof.

7. The binding molecule of claim 1, wherein the TNFα antagonist comprises an amino acid sequence that is at least 95% identical to SEQ ID NO: 13, or a functional fragment thereof.

8. The binding molecule of claim 1, wherein the TNFα antagonist comprises an amino acid sequence identical to a sequence corresponding to amino acids 1-235 of SEQ ID NO: 13.

9. The binding molecule of claim 8, wherein the VH domain comprises a VH amino acid sequence that is at least 95% identical to the amino acid sequence of SEQ ID NO: 94; and wherein the VL domain comprises a VL amino acid sequence that is at least 95% identical to the amino acid sequence of SEQ ID NO: 95.

10. The binding molecule of claim 9, wherein the binding molecule comprises a fusion protein comprising the NGF antagonist fused to the TNFα antagonist through a linker.

11. The binding molecule of claim 10, wherein the binding molecule comprises a homodimer of the fusion protein.

12. The binding molecule of claim 11, wherein the TNFα antagonist is a soluble, TNFα-binding fragment of TNFR-2 fused at its carboxy-terminus to an immunoglobulin Fc domain via a linker.

13. The binding molecule of claim 1, wherein the VH domain comprises a VH amino acid sequence that is at least 90% identical to the amino acid sequence of SEQ ID NO: 94; and wherein the VL domain comprises a VL amino acid sequence that is at least 90% identical to the amino acid sequence of SEQ ID NO: 95.

14. The binding molecule of claim 1, wherein the VH domain comprises a VH amino acid sequence that is at least 95% identical to the amino acid sequence of SEQ ID NO: 94; and wherein the VL domain comprises a VL amino acid sequence that is at least 95% identical to the amino acid sequence of SEQ ID NO: 95.

15. The binding molecule of claim 1, wherein the binding molecule comprises a homodimer of a fusion polypeptide comprising an amino acid sequence that is at least 95% identical to the amino acid sequence of SEQ ID NO: 17.

16. A pharmaceutical composition comprising the binding molecule of claim 1, and a pharmaceutically acceptable excipient.

17. A lyophilized composition comprising the binding molecule of claim 1.

18. A reconstituted lyophilized composition comprising the binding molecule of claim 1.

19. A kit comprising the binding molecule of claim 1.

\* \* \* \* \*